US006087323A

United States Patent [19]
Gwynne et al.

[11] Patent Number: 6,087,323
[45] Date of Patent: *Jul. 11, 2000

[54] USE OF NEUREGULINS AS MODULATORS OF CELLULAR COMMUNICATION

[75] Inventors: David I. Gwynne, Beverly; Nagesh K. Mahanthappa, Cambridge; Mark A. Marchionni, Arlington; Olivia Bermingham-McDonogh, Watertown; Stanley M. Goldin, Lexington; Robert N. McBurney, Newton, all of Mass.

[73] Assignee: Cambridge Neuroscience, Inc., Cambridge, Mass.

[*] Notice: This patent is subject to a terminal disclaimer.

[21] Appl. No.: 08/341,018

[22] Filed: Nov. 17, 1994

Related U.S. Application Data

[63] Continuation-in-part of application No. 08/036,555, Mar. 24, 1993, Pat. No. 5,530,109, which is a continuation-in-part of application No. 07/965,173, Oct. 23, 1992, abandoned, application No. 07/940,389, Sep. 3, 1992, abandoned, application No. 07/907,138, Jun. 30, 1992, abandoned, application No. 07/863,703, Apr. 3, 1992, abandoned.

[51] Int. Cl.$^7$ ..................................................... A61K 38/00

[52] U.S. Cl. .................................. 514/2; 514/12

[58] Field of Search ............................ 514/12, 2

[56] References Cited

U.S. PATENT DOCUMENTS

| | | | |
|---|---|---|---|
| 5,082,670 | 1/1992 | Gage et al. | 424/520 |
| 5,237,056 | 8/1993 | Fischbach | 536/23.5 |
| 5,367,060 | 11/1994 | Vandlen et al. | 530/399 |
| 5,399,346 | 3/1995 | Anderson et al. | 530/399 |
| 5,602,096 | 2/1997 | Goodearl et al. | 514/12 |

FOREIGN PATENT DOCUMENTS

| | | |
|---|---|---|
| WO 94/00140 | 1/1994 | WIPO . |
| WO 94/04560 | 3/1994 | WIPO . |
| WO 94/08007 | 4/1994 | WIPO . |

OTHER PUBLICATIONS

Peles et al. (1993) Bioessays 15, 815–824.
Danilenko et al. (1994) FASEB Journal 8 (4–5), A535.
Brockes, J.P. et al., Development in the Nervous System, 309–327, 1980, The neuron as a Source of Mitogen: Its Influence on the Proliferation of Glial and Non–neural Cells.
Danilenko et al., FASEB Journal, vol. 8 Numbers 4–5, A535, 1994, Neu Differentiation Factor (NDEF) Accelerates Epidermal Migration and Differentiation in Excisional Wounds.
Marshall, Special News Report, vol. 269, 1050–1055, Aug. 25, 1995, Gene Therapy's Growing Pains.
Verdi, et al, Neuron, vol. 16, 515–527, Mar. 1996, A Reciprocal Cell–Cell Interation Mediated by NT–3 and Neuregulins Controls the Early Survival and Development of Sympathetic Neuroblasts.
Yao et al, Proc. Natl. Acad. Sci. USA, vol. 89, 3357–3361, Apr. 1992, Expression of Human Factor IX in Mice after Injection of Genetically Modified Myoblasts.
Cheema, et al, Journal of Neuroscience Research, vol. 37, 213–218, 1994, Leukemia Inhibitory Factor Prevents the Death of Axotomised Sensory Neurons in the Dorsal Root Ganglia of the Neonatal Rat.
Curtis, et al, Neuron, vol. 12, 191–204, 1994, Retrograde Axonal Transport of LIF is Increased by Peripheral Nerve Injury: Correlation with Increased LIF Expression in Distal Nerve.
Fann, et al, Journal of Neurochemistry, vol. 61, 1349–1355, 1993, A Novel Approach to Screen for Cytokine Effects on Neuronal Gene Expression.
Grinspan, et al, The Journal of Neuroscience, vol. 16, 6107–6118, Axonal Interactions Regulate Schwann Cell Apoptosis in Developing Peripheral Nerve: Neuregulin Receptors and the Role of Neuregulins.
Hefti, Journal of Neurobiology, vol. 25, No. 11, 1418–1435, 1994, Neurotrophic Factor Therapy for Nervous System Degenerative Diseases.
Henderson, et al, Science, vol. 266, 1062–1064, 1994, GDNF: A Potent Survival Factor for Motoneurons Present in Peripheral Nerve and Muscle.
Hughes, et al, Journal of Neuroscience Research, vol. 36, 663–671, 1993, Members of Several Gene Families Influence Survival of Rat Motoneurons in Vitro and In Vivo.
Kotzbauer, et al, Neuron, vol. 12, 763–773, 1994, Postnatal Development of Survival Responsiveness in Rat Sympathetic Neurons to Leukemia Inhibitory Factor and Ciliary Neurotrophic Factor.
Lin, et al, Science, vol. 260, 1130–1132, 1993, GDNF: A Glial Cell Line–Derived Neurotrophic Factor for Midbrain Dpaminergic Neurons.
Mahanthappa, et al, The Journal of Neuroscience, vol. 16, 4673–4683, 1996, Glial Growth Factor 2, a Soluble Neuregulin, Directly Increases Schwann Cell Motility and Indirectly Promotes Neurite Outgrowth.
Martinou, et al, Neuron, vol. 8, 737–744, 1992, Cholinergic Differentiation Factor (CDF/LIF) Promotes Survival of Isolated Rat Embryonic Motoneurons in Vitro.
Oppenheim, et al., Nature, vol. 373, 344–346, 1995, Developing motor neurons rescued from programmed and axotomy–induced cell death by GDNF.

(List continued on next page.)

*Primary Examiner*—Elizabeth Kemmerer
*Assistant Examiner*—Nirmal S. Basi
*Attorney, Agent, or Firm*—Clark & Elbing LLP; Kristina Bieker-Brady

[57] ABSTRACT

The present invention relates to methods of affecting cellular communication in a vertebrate. The communication is affected by the administration of a neuregulin to a vertebrate, where the neuregulin interacts with a first cell type which results in the production of a product (i.e., Product A). This product, in turn, affects the function of a second cell type. Methods are disclosed in which the affect in function of the second cell type, described above, results in the production of a second product (i.e., Product B) which, in turn, can affect the function of the first cell type or a third cell type. Additional methods are included for treatment of disorders involving an altered or inadequate level of production of a product involved in cellular communication.

20 Claims, 54 Drawing Sheets

OTHER PUBLICATIONS

Pinkas–Kramarski, Proc. Natl. Acad. Sci. USA, vol. 91, 9387–9391, 1994, Brain neurons and glial cells express Neu differentiation factor/heregulin: A survival factor for astrocytes.

Qin–Wei, et al, The Journal of Neuroscience, vol. 14, 7629–7640, 1994, Cell Death of Spinal Motoneurons in the Chick Embryo following Deafferentation: Rescue Effects of Tissue Extracts, Soluble Proteins, and Neurotrophic Agents.

Syroid, et al, Proc. Natl. Acad. Sci. USA, vol. 93, 9229–9234, 1996, Cell Death in the Schwann Cell Lineage and its Regulation by Neuregulin.

Trachtenberg, et al, Nature, vol. 379, 174–176, 1996, Schwann Cell Apoptosis at Developing Neuromuscular Junctions is Regulated by Glial Growth Factor.

Xie, et al, Biotechniques, vol. 11, No. 3, 325–327, 1991, Rapid, Small–Scale RNA Isolation from Tissue Culture Cells.

Yamamori, et al, Science, vol. 246, 1412–1416, 1989, The Cholinergic Neuronal Differentiation Factor from Heart Cells is Identical to Leukemia Inhibitory Factor.

Yan, et al, Nature, vol. 373, 341–344, 1995, In Vivo Neurotrophic Effects of GDNF on Neonatal and Adult Facial Motor Neurons.

Yuen, et al., Annals of Neurology, vol. 40, No. 3, 340–354, 1996, Therapeutic Potential of Neurotrophic Factors for Neurological Disorders.

```
(SEQ ID NO: 1)CCTGCAG CAT CAA GTG TGG GCG GCG AAA GCC GGG GGC TTG AAG AAG GAC TCG CTG   55
     (SEQ ID NO: 2)His Gln Val Trp Ala Ala Lys Ala Gly Gly Leu Lys Lys Asp Ser Leu

CTC ACC GTG CGC CTG GGC GCC TGG GCC CAC CCC GCC TTC CCC TCC TGC          103
              Leu Thr Val Arg Leu Gly Ala Trp Gly His Pro Ala Phe Pro Ser Cys

GGG CGC CTC AAG GAG GAC AGC AGG TAC ATC TTC ATG GAG CCC GAG              151
              Gly Arg Leu Lys Glu Asp Ser Arg Tyr Ile Phe Met Glu Pro Glu

GCC AAC AGC AGC GGG CCC GGC CTT CCG AGC CTC CTT CCC CCC                  199
              Ala Asn Ser Ser Gly Pro Gly Leu Pro Ser Leu Leu Pro Pro

TCT CGA GAC GGG CCG GAA CCT CAA GGA GGT CAG CCG GCT GTG                  247
              Ser Arg Asp Gly Pro Glu Pro Gln Glu Gly Gln Pro Ala Val

CAA CGG TGC GCC TTG CCT CCC CGC TTG AAA GAG ATG AAG AGT CAG GAG          295
              Gln Arg Cys Ala Leu Pro Pro Arg Leu Lys Glu Met Lys Ser Gln Glu

TCT GTG GCA GGT TCC AAA CTA GTG CTT CGG TGC GAG ACC AGT TCT GAA          343
              Ser Val Ala Gly Ser Lys Leu Val Leu Arg Cys Glu Thr Ser Ser Glu

TAC TCC TCT CTC AAG TTC AAG TGG TTC AAT GGG AGT GAA TTA AGC              391
              Tyr Ser Ser Leu Lys Phe Lys Trp Phe Asn Gly Ser Glu Leu Ser

CGA AAG AAC AAA CCA GAA AAC ATC AAG ATA CAG ATT AAA AGG CCG GGG AAG      439
              Arg Lys Asn Lys Pro Glu Asn Ile Lys Ile Gln Ile Lys Arg Pro Gly Lys

TCA GAA CTT CGC ATT AGC AAA GCG TCA CTG GCT GAT TCT GGA GAA TAT          487
              Ser Glu Leu Arg Ile Ser Lys Ala Ser Leu Ala Asp Ser Gly Glu Tyr

ATG TGC AAA GTG ATC AGC AAA CTA GGA AAT GAC AGT GCC TCT GCC AAC          535
              Met Cys Lys Val Ile Ser Lys Lue Gly Asn Asp Ser Ala Ser Ala Asn
```

Fig. 11A

```
ATC ACC ATT GTG GAG TCA AAC GGT AAG AGA TGC CTA CTG CGT GCT ATT    583
Ile Thr Ile Val Glu Ser Asn Gly Lys Arg Cys Leu Leu Arg Ala Ile

TCT CAG TCT CTA AGA GGA GTG ATC AAG GTA TGT GGT CAC ACT    625
Ser Gln Ser Leu Arg Gly Val Ile Lys Val Cys Gly His Thr

TGAATCACGC AGGTGTGTGA AATCTCATTG TGAACAAATA AAAATCATGA AAGGAAAAAA    685

AAAAAAAAA AATCGATGTC GACTCGAGAT GTGGCTGCAG GTCGACTCTA GAGGATCCC    744
```

Fig. 11A
Continued (SEQ ID NO: 3) CCTGCAG CAT CAA GTG TGG GCG GCG AAA GCC GGG GGC TTG AAG AAG GAC TCG CTG 55
(SEQ ID NO: 4) His Gln Val Trp Ala Ala Lys Ala Gly Gly Leu Lys Lys Asp Ser Leu CTC ACC GTG CGC CTG GGC GCC CTG GGC CAC CCC GCC TTC CCC TCC TGC 103
Leu Thr Val Arg Leu Gly Ala Leu Gly His Pro Ala Phe Pro Ser Cys GGG CGC CTC AAG GAG GAC AGC AGG TAC ATC TTC TTC ATG GAG CCC GAG 151
Gly Arg Leu Lys Glu Asp Ser Arg Tyr Ile Phe Phe Met Glu Pro Glu GCC AAC AGC AGC GGC GGG CCC CTT CCG AGC CTC CTT CCC CCC 199
Ala Lys Ser Ser Gly Gly Pro Arg Leu Pro Ser Leu Leu Pro Pro TCT CGA GAC GGG CCG GAA CCT CAA GGA GGT CAG CCG GGT GCT GTG 247
Ser Arg Asp Gly Pro Glu Pro Gln Gly Gly Gln Pro Gly Ala Val CAA CGG TGC GCC TTG CCT CCC CGC TTG AAA GAG ATG AAG AGT CAG GAG 295
Gln Arg Cys Ala Leu Pro Pro Arg Leu Lys Glu Met Lys Ser Gln Glu TCT GTG GCA GGT TCC AAA CTA GTG CTT CTT CGG TGC GAG ACC AGT TCT GAA 343
Ser Val Ala Gly Ser Lys Leu Val Leu Leu Arg Cys Glu Thr Ser Glu TAC TCC TCT CTC AAG TTC TGG TTC AAG ATA CAG AAT GGG AGT TTA AGC 391
Tyr Ser Ser Leu Lys Phe Trp Phe Lys Ile Gln Asn Gly Leu Ser CGA AAG AAC AAA CCA GAA AAC ATC AAG ATA ATC CAG AAA AGG CCG GGG AAG 439
Arg Lys Asn Lys Pro Glu Asn Ile Lys Ile Ile Gln Lys Arg Pro Gly Lys TCA GAA CTT CGC ATT AGC AAA GCG TCA CTG GCT GAT TCT GGA GAA TAT 487
Ser Glu Leu Arg Ile Ser Lys Ala Ser Leu Ala Asp Ser Gly Glu Tyr ATG TGC AAA GTG ATC AGC AAA CTA GGA AAT GAC AGT GCC TCT GCC AAC 535
Met Cys Lys Val Ile Ser Lys Leu Gly Asn Asp Ser Ala Ser Ala Asn

Fig. 11B

```
(SEQ ID NO: 3) ATC ACC ATT GTG GAG TCA AAC GCC ACA TCC ACA TCT ACA GCT GGG ACA   583
(SEQ ID NO: 4)    Ile Thr Ile Val Glu Ser Asn Ala Thr Ser Thr Ser Thr Ala Gly Thr

AGC CAT CTT GTC AAG TGT GCA GAG AAG GAG AAA ACT TTC TGT GTG AAT   631
              Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC   679
              Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   727
              Leu Cys Lys Cys Gln Pro Gly Phe Thr Gly Ala Arg Cys Thr Glu Asn

GTG CCC ATG AAA GTC CAA ACC CAA GAA AGT GCC CAA ATG AGT TTA CTG   775
              Val Pro Met Lys Val Gln Thr Gln Glu Ser Ala Gln Met Ser Leu Leu

GTG ATC GCT GCC AAA ACT ACG TAATGGCCAG CTTCTACAGT ACGTCCACTC      826
              Val Ile Ala Ala Lys Thr Thr

CCTTTCTGTC TCTGCCCTGAA TAGCGCATCT CAGTCGGTGC CGCTTTCTTG TTGCCGCATC 886

TCCCCTCAGA TTCCTCCTAG AGCTAGATGC GTTTTACCAG GTCTAACATT GACTGCCTCT  946

GCCTGTCGCA TGAGAACATT AACACAAGCG ATTGTATGAC TTCCTCTGTC CGTGACTAGT 1006

GGGCTCTGAG CTACTCGTAG GTGCGTAAGG CTCCAGTGTT TCTGAAATTG ATCTTGAATT 1066

ACTGTGATAC GACATGATAG TCCCTCTCAC CCAGTGCAAT GACAATAAAG GCCTTGAAAA 1126

GTCAAAAAAA AAAAAAAAAA AAAAAATCGA TGTCGACTCG AGATGTGGCT GCAGGTCGAC 1186

TCTAGAG                                                          1193
```

Fig. 11C

```
(SEQ ID NO: 5) CCTGCAG CAT CAA GTG TGG GCG GCG AAA GCC GGG GGC TTG AAG AAG GAC TCG CTG    55
(SEQ ID NO: 6)          His Gln Val Trp Ala Ala Lys Ala Gly Gly Leu Lys Lys Asp Ser Leu

CTC ACC GTG CGC CTG GGC GCC TGG GGC CAC CCC GCC TTC TCC CCC TCC TGC         103
              Leu Thr Val Arg Leu Gly Ala Trp Gly His Pro Ala Phe Ser Pro Ser Cys

GGG CGC CTC AAG GAG GAC AGC AGG TAC ATC TTC TTC ATG GAG CCC GAG             151
              Gly Arg Leu Lys Glu Asp Ser Arg Tyr Ile Phe Phe Met Glu Pro Glu

GCC AAC AGC AGC GGC GGG CCC CGC CTT CCG AGC CTC CTT CCC CCC                 199
              Ala Asn Ser Ser Gly Gly Pro Arg Leu Pro Ser Leu Leu Pro Pro

TCT CGA GAC GGG CCG GAA CCT CAA GGA GGT CAG CCG GGT GCT GTG                 247
              Ser Arg Asp Gly Pro Glu Pro Gln Glu Gly Gln Pro Gly Ala Val

CAA CGG TGC GCC TTG CCT CCC CGC TTG AAA GAG ATG AAG AGT CAG GAG             295
              Gln Arg Cys Ala Leu Pro Pro Arg Leu Lys Glu Met Lys Ser Gln Glu

TCT GTG GCA GGT TCC AAA CTA GTG CTT CGG CTT CTG GAG ACC AGT TCT GAA         343
              Ser Val Ala Gly Ser Lys Leu Val Leu Arg Leu Leu Glu Thr Ser Ser Glu

TAC TCC TCT CTC AAG TTC AAG TGG TTC AAG AAT GGG AGT GAA TTA AGC             391
              Tyr Ser Ser Leu Lys Phe Lys Trp Phe Lys Asn Gly Ser Glu Leu Ser

CGA AAG AAC AAA CCA GAA AAC ATC AAG ATA CAG AAA AGG CCG GGG AAG             439
              Arg Lys Asn Lys Pro Glu Asn Ile Lys Ile Gln Lys Arg Pro Gly Lys

TCA GAA CTT CGC ATT AGC AAA GCG TCA CTG GCT GAT TCT GGA GAA TAT             487
              Ser Glu Leu Arg Ile Ser Lys Ala Ser Leu Ala Asp Ser Gly Glu Tyr
```

Fig. 11D

```
(SEQ ID NO: 5) ATG TGC AAA GTG ATC AGC AAA CTA GGA AAT GAC AGT GCC TCT GCC AAC      535
(SEQ ID NO: 6) Met Cys Lys Val Ile Ser Lys Leu Gly Asn Asp Ser Ala Ser Ala Asn

ATC ACC ATT GTG GAG TCA AAC GCC ACA TCC ACA TCT ACA GCT GGG ACA                    583
Ile Arg Ile Val Glu Ser Asn Ala Thr Ser Thr Ser Thr Ala Gly Thr

AGC CAT GTC GTC AAG TGT GCA GAG AAG GAG CTT TCA GAC ACT TTC TGT GTG AAT            631
Ser His Leu Val Lys Cys Ala Glu Lys Glu Leu Ser Asp Thr Phe Cys Val Asn

GGA GGC GAG TGC TTC ATG GTG AAA GAC CTT TCA AAT CCC TCA AGA TAC                    679
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC                    727
Leu Cys Lys Cys Pro Asn Glu Phe Thr Gly Asp Arg Cys Gln Asn Tyr

GTA ATG GCC AGC TTC TAC AGT ACG TCC ACT CCC TTT CTG TCT CTG CCT                    775
Val Met Ala Ser Phe Tyr Ser Thr Ser Thr Pro Phe Leu Ser Leu Pro

GAA TAGGCGCATCT CAGTCGGTGC CGCTTTCTTG TTGCCGCATC TCCCCCTCAGA TTCCGCCTAG            838
Glu

AGCTAGATGC GTTTTACCAG GTCTAACATT GACTGCCTCT GCCTGTCGCA TGAGAACATT                  898

AACACAAGCG ATTGTATGAC TTCCTCTGTC CGTGACTAGT GGGCTCTGAG CTACTCGTAG                  958

GTGCGTAAGG CTCCAGTGTT TCTGAAATTG ATCTTGAATT ACTGTGATAC GACATGATAG                  1018

TCCCTCTCAC CCAGTGCAAT GACAATAAAG GCCTTGAAAA GTCAAAAAAA AAAAAAAAA                   1078

AAAAATCGAT GTCGACTCGA GATGTGGCTG                                                   1108
```

CODING SEGMENT F: (bovine,top,human,bottom)

```
1AGTTTCCCCC CCCAACTTGT CGGAACTCTG GGCTCGCGCG CAGGGCAGGA GCGGAGCGGC    60
GGCGGCTGCC CAGGCGATGC GAGCGCGGGC CGGACGGTAA TCGCCTCTCC CTCCTCGGGC   120
TGCCGAGCGCG CCGGACCGAG GCAGCGACAG GAGCGGACCG CGGCGGGAAC CGAGGACTCC  180
CCAGCGGGCGC GCCAGCAGGA GCCACCCCGC GAGNCGTGCG ACCGGGACGG AGCGCCCGCC  240
AGTCCCAGGT GGCCCCGGACC GCACGTTGCG TCCCCGCGCT CCCCGCCGGC GACAGGAGAC  300
GCTCCCCCCC ACGCCGGCGCG CGCCTCGGCC CGGTCGCTGG CCCGCCTCCA CTCCGGGGAC  360
            CGGGAG CGCCTCAGCG CGGACGCTCG CTCTC..CCC CTCGAGGGAC

2
AAACTTTTCC CGAAGCCGAT CCCAGCCCTC GGACCCAAAC TTGTCGCGCG TCGCCTTCGC   420
AAACTTTTCC CAAACCCCGAT CCGAGCCCTT GGACCAAA.. ..........C TCGCCTGCGC

Met Ser Glu Arg Arg
3
CGGGAGCCGT CCGCGCAGAG CGTGCACTTC TCGGGCGAG ATG TCG GAG CGC AGA      474
CGAGAGCCGT CCGCGTAGAG CGCTC.CGTC TCCGGCGAG ATG TCC GAG CGA AAA
4                                                         K

Glu Gly Lys Gly Lys Gly Gly Lys Lys Asp Arg Gly Ser Gly
GAA GGC AAA GGC AAA GGG GGC AAG AAG GAC CGA GGC TCC GGG            522
GAA GGC AGA GGC AAA GGC AGA GGC AAG AAG GAG CGA GGC TCC GGC
         R                                  E

Lys Lys Pro Val Pro Ala Ala Gly Gly Pro Ser Pro Ala
AAG AAG CCC GTG CCC GCT GGC GGC CCG AGC CCA G                      559
AAG AAG CCG GAG TCC GCG GGC AGC CAG AGC CCA G
         E        S
```

1. (SEQ ID NO: 7)
2. (SEQ ID NO: 8)
3. (SEQ ID NO: 9)
4. (SEQ ID NO: 10)

CODING SEGMENT E: Bovine

```
(SEQ ID NO: 11) CC CAT CAN GTG TGG GCG GCG AAA GCC GGG GGC TTG AAG AAG GAC TCG      47
(SEQ ID NO: 12)     His Gln Val Trp Ala Ala Lys Ala Gly Gly Leu Lys Lys Asp Ser

CTG CTC ACC GTG CGC CTG GGC GCC TGG GGC CAC CCC GCC TTC CCC TCC      95
                Leu Leu Thr Val Arg Leu Gly Ala Trp Gly His Pro Ala Phe Pro Ser

TGC GGG CGC CTC AAG GAG GAC AGC AGG TAC ATC TTC TTC ATG GAG CCC     143
                Cys Gly Arg Leu Lys Glu Asp Ser Arg Tyr Ile Phe Phe Met Glu Pro

GAG GCC AAC AGC AGC GGC GGG CCC CGC CTT,CCG AGC CTC CTT CCC         191
                Glu Ala Asn Ser Ser Gly Gly Pro Arg Leu Pro Ser Leu Leu Pro

CCC TCT CGA GAC GGG CCT CAA GAA CCT CAG GGT GGG CAG CCG GGT GCT     239
                Pro Ser Arg Asp Gly Pro Gln Glu Pro Gln Gly Gly Gln Pro Gly Ala

GTG CAA CGG TGC G                                                   252
                Val Gln Arg Cys
```

Fig. 13B

CODING SEGMENT B: (bovine, top; human, bottom)

```
          Leu Pro Pro Arg Leu Lys Glu His Lys Ser Gln Glu Ser Val Ala Gly
       2                                                                                48
       1  CCT TGC CTC CCC GCT AAG GAA AGA AGA TGA AGG AGT CTG TGG CAG
                                                                    ─── ───
       3  CCT TGC CTC CCC GAT AAG AAG AGA TGA AGG AAT CGG CTG CAG
       4                         Q                              A

Ser Lys Leu Val Leu Arg Cys Glu Thr Ser Ser Glu Tyr Ser Ser Leu
                                                                                96
          GTT CCA AAC TAG TGC TTC GGT GCG AGA CCA GTT AAT CTG ACT CCT CTC
                                                                    ─── ───
          GTT CCA AAC TAG TGC TCC GGT GTG AAA CCA GTT AAT CTG ACT CCT CTC

Lys Phe Lys Trp Phe Lys Asn Gly Ser Glu Leu Ser Arg Lys Asn Lys
                                                                                144
          TCA AGT TCA AGT GGT AGA ATG GGA ATG AAT TAA GCC GAA AGA ACA
                                                                    ─── ───
          TCA GAT TCA AGT GGT AGA ATG GGA ATG AAT TGA ATC GAA AAA ACA
          R                                              N   N

Pro Gly Asn Ile Lys Ile Gln Lys Arg Pro Gly
                                                                                178
          AAC CAC AAA ACA TCA AGA TAC AGA AAA GGC CGG G
                                                          ─── ───
          AAC CAC AAA ATA TCA AGA TAC AAA AAA AGC CAG G
                            K
```

1. (SEQ ID NO: 13)
2. (SEQ ID NO: 14)
3. (SEQ ID NO: 15)
4. (SEQ ID NO: 16)

Fig. 13C

CODING SEGMENT A: (bovine,top;human,bottom)

```
     2   Lys Ser Glu Leu Arg Ile Ser Lys Ala Ser Leu Ala Asp Ser Gly                          46
   1 G   AAG TCA GAA CTT CGC ATT AGC AAA GCG TCA CTG GCT GAT TCT GGA
         ||| ||| ||| ||| ||| ||| ||| ||| ||| ||| ||| ||| ||| ||| |||
   3 G   AAG TCA GAA CTT CGC ATT AAC AAA GCA TCA CTG GCT GAT TCT GGA
     4                               N

Glu Tyr Met Cys Lys Val Ile Ser Lys Leu Gly Asn Asp Ser Ala Ser                      94
         GAA TAT ATG TGC AAA GTG ATC AGC AAA CTA GGA AAT GAC AGT GCC TCT
         ||| ||| ||| ||| ||| ||| ||| ||| ||| ||| ||| ||| ||| ||| ||| |||
         GAG TAT ATG TGC AAA GTG ATC AGC AAA TTA GGA AAT GAC AGT GCC TCT

Ala Asn Ile Thr Ile Val Glu Ser Asn Ala                                              122
         GCC AAC ATC ACC ATT GTG GAG TCA AAC G
         ||| ||| ||| ||| ||| ||| ||| ||| ||| |
         GCC AAT ATC ACC ATC GTG GAA TCA AAC G
```

1. (SEQ ID NO: 17)
2. (SEQ ID NO: 18)
3. (SEQ ID NO: 19)
4. (SEQ ID NO: 20)

Fig. 13D

CODING SEGMENT A': Bovine (SEQ ID NO: 21) TCTAAAACTA CAGAGACTGT ATTTTCATGA TCATCATAGT TCTGTGAAAT ATACTTAAAC    60

CGCTTTGGTC CTGATCTTGT AGG AAG TCA GAA CTT CGC ATT AGC AAA GCG    110
(SEQ ID NO: 22) Lys Ser Glu Leu Arg Ile Ser Lys Ala

TCA CTG GCT GAT TCT GGA GAA TAT ATG TGC AAA GTG ATC AGC AAA CTA    158
Ser Leu Ala Asp Ser Gly Glu Tyr Met Cys Lys Val Ile Ser Lys Leu

GGA AAT GAC AGT GCC TCT GCC AAC ATC ACC ATT GTG GAG TCA AAC GGT    206
Gly Asn Asp Ser Ala Ser Ala Asn Ile Thr Ile Val Glu Ser Asn Gly

AAG AGA TGC CTA CTG CGT GCT ATT TCT CAG TCT CTA AGA GGA GTG ATC    254
Lys Arg Cys Leu Leu Arg Ala Ile Ser Gln Ser Leu Arg Gly Val Ile

AAG GTA TGT GGT CAC ACT TGAATCACGC AGGTGTGTGA AATCTCATTG    302
Lys Val Cys Gly His Thr

TGAACAAATA AAAATCATGA AAGGAAAACT CTATGTTTGA AATATCTTAT GGGTCCTCCT    362

GTAAAGCTCT TCACTCCATA AGGTGAAATA GACCTGAAAT ATATATAGAT TATTT    417

Fig. 13E 1. (SEQ ID NO: 23)
2. (SEQ ID NO: 24)
3. (SEQ ID NO: 25)
4. (SEQ ID NO: 26)

CODING SEGMENT G: (bovine, top; human, bottom)

```
 2Glu Ile Thr Thr Gly Met Pro Ala Ser Thr Glu Thr Ala Tyr Val Ser
 1 AG  ATC ACC ACT GGC ATG CCA GCC TCA ACT GAG ACA GCG TAT GTG TCT    47
    ||  |||  |  ||| ||  ||| ||| ||| ||| || |  || ||| ||| |||
 3AG  ATC ATC ACT GGT ATG CCA GCC TCA ACT GAA GGA GCA TAT GTG TCT
 4         I                                    G

Ser Glu Ser Pro Ile Arg Ile Ser Val Ser Thr Glu Gly Thr Asn Thr
   TCA GAG TCT CCC ATT AGA ATA TCA GTA TCA ACA GAA GGA ACA AAT ACT    95
   ||| ||| ||| ||| ||| ||| ||| ||| ||| || ||| ||| |||  | ||| |||
   TCA GAG TCT CCC ATT AGA ATA TCA GTA TCC ACA GAA GGA GCA AAT ACT
                                                      A

Ser Ser Ser
   TCT TCA T                                                         102
   ||| ||| |
   TCT TCA T
```

Fig. 13F 1. (Seq ID NO: 27)
2. (SEQ ID NO: 28)
3. (SEQ ID NO: 29)
4. (SEQ ID NO: 30)

CODING SEGMENT C: (bovine,top;human,bottom)

```
2    Thr Ser Thr Ser Thr Ala Gly Thr Ser His Leu Val Lys Cys Ala
1CC  ACA TCC ACA TCT ACA GCT GGG ACA AGC CAT CTT GTC AAG TGT GCA    47
 |   ||| ||  ||| ||  ||  ||  ||| ||| ||| ||| ||| ||  ||  ||| ||
3CT  ACA TCT ACA TCC ACC ACT GGG ACA AGC CAT CTT GTA AAA TGT GCG
4                         T

Glu Lys Glu Lys Thr Phe Cys Val Asn Gly Gly Glu Cys Phe Met Val
     GAG AAG GAG AAA ACT TTC TGT GTG AAT GGA GGC GAG TGC TTC ATG GTG   95
     ||| ||| ||| ||| ||| ||| ||| ||| ||| ||| ||  ||| ||| ||| ||| |||
     GAG AAG GAG AAA ACT TTC TGT GTG AAT GGA GGG GAG TGC TTC ATG GTG

Lys Asp Leu Ser Asn Pro Ser Arg Tyr Leu Cys
     AAA GAC CTT TCA AAT CCC TCA AGA TAC TTG TGC                       128
     ||| ||| ||| ||| ||  ||| ||  ||| ||| ||| |||
     AAA GAC CTT TCA AAC CCC TCG AGA TAC TTG TGC
```

Fig. 13G 1. (SEQ ID NO: 31)
2. (SEQ ID NO: 32)
3. (SEQ ID NO: 33)
4. (SEQ ID NO: 34)

CODING SEGMENT C/D:

```
²Lys Cys Gln Pro Gly Phe Thr Gly Ala Arg Cys Thr Glu Asn Val Pro
¹AAG TGC CAA CCT GGA TTC ACT GGA GCG AGA TGT ACT GAG AAT GTG CCC    48
  ||| ||| ||| ||| ||| ||| ||| ||  ||| ||| ||| ||| ||| ||| ||| |||
³AAG TGC CAA CCT GGA TTC ACT GGA GCA AGA TGT ACT GAG AAT GTG CCC

Met Lys Val Gln Thr Gln Glu
ATG AAA GTC CAA ACC CAA GAA                                         69
||| ||| ||| ||| | | ||| |||
ATG AAA GTC CAA AAC CAA GAA
⁴                 N
```

Fig. 13H

CODING SEGMENT C/D': (bovine,top;human,bottom)

```
(SEQ ID NO: 36)Lys Cys Pro Asn Glu Phe Thr Gly Asp Arg Cys Gln Asn Tyr Val Met     48
(SEQ ID NO: 35)AAG TGC CCA AAT GAG TTT ACT GGT GAT CGC TGC CAA AAC TAC GTA ATG
               ---  ---  ---  ---  ---  ---  ---  ---  ---  ---  ---  ---  ---  ---  ---  ---
               AAG TGC CCA AAT GAG TTT ACT GGT GAT CGC TGC CAA AAC TAC GTA ATG

Ala Ser Phe Tyr                                                       60
               GCC AGC TTC TAC
               ---  ---  ---  ---
               GCC AGC TTC TAC
```

Fig. 13I

CODING SEGMENT D: (bovine,top;human,bottom)

```
(SEQ ID NO: 38)Ser Thr Ser Thr Pro Phe Leu Ser Leu Pro Glu  *                       36
(SEQ ID NO: 37)AGT ACG TCC ACT CCC TTT CTG TCT CTG CCT GAA TAG
               ---  ---  ---  ---  ---  ---  ---  ---  ---  ---  ---  ---
               AGT ACG TCC ACT CCC TTT CTG TCT CTG CCT GAA TAG
```

Fig. 13J

CODING SEGMENT D': human

```
(SEQ ID NO: 40)Lys His Leu Gly Ile Glu Phe Met Glu                                   27
(SEQ ID NO: 39)AAG CAT CTT GGG ATT GAA TTT ATG GAG
```

Fig. 13K 1. (SEQ ID NO: 41)
2. (SEQ ID NO: 42)
3. (SEQ ID NO: 43)
4. (SEQ ID NO: 44)

CODING SEGMENT H: (bovine, top; human, bottom)

```
2Lys Ala Glu Glu Leu Tyr Gln Lys Arg Val Leu Thr Ile Thr Gly Ile
1AAA GCG GAG GAG CTC TAC CAG AAG AGA GTG CTC ACC ATT ACC GGC ATT     48
  ||  |||  |||  |||  ||  |||  |||  |||  |||  |||  ||  |||  ||  |||  |||  ||
3AAG GCG GAG GAG CTG TAC CAG AAG AGA GTG CTG ACC ATA ACC GGC ATC

Cys Ile Ala Leu Leu Val Val Gly Ile Met Cys Val Val Val Tyr Cys
 TGC ATC GCG CTG CTC GTG GTT GGC ATC ATG TGT GTG GTG GTC TAC TGC    96
 |||  |||  ||  ||  ||  |||  ||  |||  |||  |||  |||  |||  |||  | |  |||  |||
 TGC ATC GCC CTC CTT GTG GTC GGC ATC ATG TGT GTG GTG GCC TAC TGC
4                                                      A

Lys Thr Lys Lys Gln Arg Lys Lys Leu His Asp Arg Leu Arg Gln Ser
 AAA ACC AAG AAA CAA CGG AAA AAG CTT CAT GAC CGG CTT CGG CAG AGC   144
 |||  |||  |||  |||  ||  |||  |||  |||  ||  |||  |||  ||  |||  |||  |||  |||
 AAA ACC AAG AAA CAG CGG AAA AAG CTG CAT GAC CGT CTT CGG CAG AGC

Leu Arg Ser Glu Arg Asn Thr Met Met Asn Val Ala Asn Gly Pro His
 CTT CGG TCT GAA AGA AAC ACC ATG ATG AAC GTA GCC AAC GGG CCC CAC   192
 |||  |||  |||  |||   ||  |||   |   |||  |||  |||   |   |||  ||  |||  ||  |||
 CTT CGG TCT GAA CGA AAC AAT ATG ATG AAC ATT GCC AAT GGG CCT CAC
                              N                    I

His Pro Asn Pro Pro Glu Asn Val Gln Leu Val Asn Gln Tyr Val
 CAC CCC AAT CCG CCC CCC GAG AAC GTG CAG CTG GTG AAT CAA TAC GTA   240
 ||  ||  ||  ||  |||  |||  |||  ||  |||  |||  |||  |||  |||  |||  |||  |||
 CAT CCT AAC CCA CCC CCC GAG AAT GTC CAG CTG GTG AAT CAA TAC GTA

Ser Lys Asn Val Ile Ser Ser Glu His Ile Val Glu Arg Glu Ala Glu
 TCT AAA AAT GTC ATC TCT AGC GAG CAT ATT GTT GAG AGA GAG GCG GAG   288
 |||  |||  ||  |||  |||  ||  ||  |||  |||  |||  |||  |||  ||  ||  |||
 TCT AAA AAC GTC ATC TCC AGT GAG CAT ATT GTT GAC AGA GAA GCA GAG
```

Fig. 13L 1. (SEQ ID NO: 41)
2. (SEQ ID NO: 42)
3. (SEQ ID NO: 43)
4. (SEQ ID NO: 44)

```
²Ser Ser Phe Ser Thr Ser His Tyr Thr Ser Thr Ala His His Ser Thr
¹AGC TCT TTT TCC ACC AGT CAC TAC ACT TCG ACA GCT CAT CAT TCC ACT    336
    ||  ||| ||| ||| ||| ||| ||  ||| ||  ||| ||  ||| ||  ||| |||
³ACA TCC TTT TCC ACC AGT CAC TAT ACT TCC ACA GCC CAT CAC TCC ACT
⁴T

Thr Val Thr Gln Thr Pro Ser His Ser Trp Ser Asn Gly His Thr Glu
ACT GTC ACT CAG ACT CCC AGT CAC AGC TGG AGC AAT GGA CAC ACT GAA    384
||| ||| ||  ||| ||| ||  ||  ||| ||| ||| ||| ||  ||| ||| ||| |||
ACT GTC ACC CAG ACT CCT AGC CAC AGC TGG AGC AAC GGA CAC ACT GAA

Ser Ile Ile Ser Glu Ser His Ser Val Ile Val Met Ser Ser Val Glu
AGC ATC ATT TCG GAA AGC CAC TCT GTC ATC GTG ATG TCA TCC GTA GAA    432
||| |||  || ||  ||| ||| ||| ||| ||  ||| ||| ||| ||| ||| ||| |||
AGC ATC CTT TCC GAA AGC CAC TCT GTA ATC GTG ATG TCA TCC GTA GAA
        L

Asn Ser Arg His Ser Ser Pro Thr Gly Gly Pro Arg Gly Arg Leu Asn
AAC AGT AGG CAC AGC AGC CCG ACT GGG GGC CCG AGA GGA CGT CTC AAT    480
||| ||| ||| ||| ||| ||| ||  ||| ||| ||| ||  ||| ||| ||| ||  |||
AAC AGT AGG CAC AGC AGC CCA ACT GGG GGC CCA AGA GGA CGT CTT AAT

Gly Leu Gly Gly Pro Arg Glu Cys Asn Ser Phe Leu Arg His Ala Arg
GGC TTG GGA GGC CCT CGT GAA TGT AAC AGC TTC CTC AGG CAT GCC AGA    528
|||     ||| ||| ||| ||| ||| ||| ||| ||| ||| ||| ||| ||| ||| |||
GGC ACA GGA GGC CCT CGT GAA TGT AAC AGC TTC CTC AGG CAT GCC AGA
    T

Glu Thr Pro Asp Ser Tyr Arg Asp Ser Pro His ser Glu Arg
GAA ACC CCT GAC TCC TAC CGA GAC TCT CCT CAT AGT GAA AG             569
||| ||| ||| ||  ||| ||| ||| ||| ||| ||| ||| ||| ||| ||
GAA ACC CCT GAT TCC TAC CGA GAC TCT CCT CAT AGT GAA AG
```

Fig. 13M

CODING SEGMENT K: Bovine

```
(SEQ ID NO: 45) A CAT AAC CTT ATA GCT GAG CTA AGG AGA AAC AAG GCC CAC AGA TCC   46
(SEQ ID NO: 46)   His Asn Leu Ile Ala Glu Leu Arg Arg Asn Lys Ala His Arg Ser

AAA TGC ATG CAG ATC CAG CTT TCC GCA ACT CAT CTT AGA GCT TCT TCC   94
              Lys Cys Met Gln Ile Gln Leu Ser Ala Thr His Leu Arg Ala Ser Ser

ATT CCC CAT TGG GCT TCA TTC TCT AAG ACC CCT TGG CCT TTA GGA AG   141
              Ile Pro His Trp Ala Ser Phe Ser Lys Thr Pro Trp Pro Leu Gly Arg
```

Fig. 13N 1. (SEQ ID NO: 47)
2. (SEQ ID NO: 48)
3. (SEQ ID NO: 49)
4. (SEQ ID NO: 50)

CODING SEGMENT L: (bovine, top; human/bottom)

```
 2Tyr Val Ser Ala Met Thr Thr Pro Ala Arg Met Ser Pro Val Asp
1G  TAT GTA TCA GCA ATG ACC ACC CCG GCT CGT ATG TCA CCT GTA GAT    46
 |  ||| ||  ||| ||  ||| ||| ||| ||| ||| ||| ||| ||| ||| ||| |||
3G  TAT GTG TCA GCC ATG ACC ACC CCG GCT CGT ATG TCA CCT GTA GAT
4

Phe His Thr Pro Ser Ser Pro Lys Ser Pro Pro Ser Glu Met Ser Pro
   TTC CAC ACG CCA AGC TCC CCC AAG TCA CCC CCT TCG GAA ATG TCC CCG   94
   ||| ||| ||| ||| ||| ||| ||| ||  ||  ||| ||| ||| ||| ||| ||  ||
   TTC CAC ACG CCA AGC TCC CCC AAA TCG CCC CCT TCG GAA ATG TCT CCA

Pro Val Ser Ser Thr Thr Val Ser Met Pro Ser Met Ala Val Ser Pro
   CCC GTG TCC AGC ACG ACG GTC TCC ATG CCC TCC ATG GCG GTC AGT CCC  142
   ||| ||| ||| ||| ||  ||| ||  ||| ||| ||  ||| ||| ||| ||| ||  |||
   CCC GTG TCC AGC ATG ACG GTG TCC ATG CCT TCC ATG GCG GTC AGC CCC
                       M

Phe Val Glu Glu Glu Arg Pro Leu Leu Leu Val Thr Pro Pro Arg Leu
   TTC GTG GAA GAG GAG AGA CCC CTG CTC CTT GTG ACG CCA CCA CGG CTG  190
   |||  || ||| ||  ||| ||| ||  ||  ||  ||| ||| || ||| ||| ||  |||
   TTC ATG GAA GAA GAG AGA CCT CTA CTT CTC GTG ACA CCA CCA AGG CTG
        N

Arg Glu Lys  -  Tyr Asp His His Ala Gln Gln Phe Asn Ser Phe His
   CGG GAG AAG ... TAT GAC CAC CAC GCC CAG CAA TTC AAC TCG TTC CAC  238
   ||| ||| |||     | | ||| ||| |   ||| ||  ||| || | || ||| |||
   CGG GAG AAG AAG TTT GAC CAT CAC CCT CAG CAG TTC AGC TCC TTC CAC
                   K   F           P

Cys Asn Pro Ala His Glu Ser Asn Ser Leu Pro Pro Ser Pro Leu Arg
   TGC AAC CCC GCG CAT GAG AGC AAC AGC CTG CCC CCC AGC CCC TTG AGG  286
    |  ||| ||| ||| |||  || || ||| ||| ||  ||   | ||| ||| ||| |||
   CAC AAC CCC GCG CAT GAC AGT AAC AGC CTC CCT GCT AGC CCC TTG AGG
   N                   D                   A
```

Fig. 13O

```
Ile Val Glu Asp Glu Glu Tyr Glu Thr Thr Gln Glu Tyr Glu Pro Ala
ATA GTG GAG GAT GAG GAA TAT GAA ACG ACC CAG GAG TAC GAA CCA GCT   334
 |   |   |   |   |  ||   |   |   |   |  ||   |   |  ||   |  ||
ATA GTG GAG GAT GAG GAG TAT GAA ACG ACC CAA GAG TAC GAG CCA GCC

Gln Glu Pro Val Lys Lys Leu Thr Asn Ser Ser Arg Arg Ala Lys Arg
CAA GAG CCG GTT AAG AAA CTC ACC AAC AGC AGC CGG CGG GCC AAA AGA   382
 |   |  ||   |   |   |   |   |  ||        |   |   |   |   |   |
CAA GAG CCT GTT AAG AAA CTC GCC AA. ..T AGC CGG CGG GCC AAA AGA
                             A

Thr Lys Pro Asn Gly His Ile Ala His Arg Leu Glu Met Asp Asn Asn
ACC AAG CCC AAT GGT CAC ATT GCC CAC AGG TTG GAA ATG GAC AAC AAC   430
 |   |   |   |  ||   |   |  ||   ||  ||   |   |  ||   |  ||   |
ACC AAG CCC AAT GGC CAC ATT GCT AAC AGA TTG GAA GTG GAC AGC AAC
                             N           V           S

Thr Gly Ala Asp Ser Ser Asn Ser Glu Ser Glu Thr Glu Asp Glu Arg
ACA GGC GCT GAC AGC AGT AAC TCA GAG AGC GAA ACA GAG GAT GAA AGA   478
 |   ||  |   |   |   |   |   |  ||   |   |  ||   |   |   |   |
ACA AGC TCC CAG AGC AGT AAC TCA GAG AGT GAA ACA GAA GAT GAA AGA
     S   S   Q
```

Fig.13P

```
Val Gly Glu Asp Thr Pro Phe Leu Ala Ile Gln Asn Pro Leu Ala Ala
GTA GGA GAA GAT ACG CCT TTC CTG GCC ATA CAG AAC CCC CTG GCA GCC    526
 |||  ||  |||  |||  |||  |||  |||  |||  | |  |||  |||  |||  |||  |||  |||  |||
GTA GGT GAA GAT ACG CCT TTC CTG GGC ATA CAG AAC CCC CTG GCA GCC
                                    G

Ser Leu Glu Ala Ala Pro Ala Phe Arg Leu Val Asp Ser Arg Thr Asn
AGT CTC GAG GCG GCC CCT GCC TTC CGC CTG GTC GAC AGC AGG ACT AAC    574
 |||  ||  |||  ||   |   |||  |||  |||  |||  |||  |    |||  |||  |||  |||  |||
AGT CTT GAG GCA ACA CCT GCC TTC CGC CTG GCT GAC AGC AGG ACT AAC
         T                                  A

Pro Thr Gly Gly Phe Ser Pro Gln Glu Glu Leu Gln Ala Arg Leu Ser
CCA ACA GGC GGC TTC TCT CCG CAG GAA GAA TTG CAG GCC AGG CTC TCC    622
 |||  ||  |||  |||  |||  ||   |   |||  |||  |||  |    |||  |||  |||  ||   ||
CCA GCA GGC CGC TTC TCG ACA CAG GAA GAA ATC CAG GCC AGG CTG TCT
     A       R               T                I

Gly Val Ile Ala Asn Gln Asp Pro Ile Ala Val *
GGT GTA ATC GCT AAC CAA GAC CCT ATC GCT GTC TAA AAC CGA AAT ACA    672
 ||  |||  ||   |||  |||  |||  |||  |||  ||   |||  |||  |||  |||  ||   |||  | |
AGT GTA ATT GCT AAC CAA GAC CCT ATT GCT GTA TAA AAC CTA AAT AAA
 S

CCC ATA GAT TCA CCT GTA AAA CTT TAT TTT ATA TAA TAA AGT ATT CCA    718
 |   |||  |||  |||  |||  |||  |||  |||  |||  |||  |||  |||  |||  |||  |||  |||
CAC ATA GAT TCA CCT GTA AAA CTT TAT TTT ATA TAA TAA AGT ATT CCA

CCT TAA ATT AAA CAA                                                733
 |||  |||  |||  |||  |||
CCT TAA ATT AAA CAA
```

Fig. 13Q

```
(SEQ ID NO: 51) ATG AGA TGG CGA CGC GCC CCG CGC TCC GGG CGT CCC GGC CCC CGG     48
(SEQ ID NO: 52) Met Arg Trp Arg Arg Ala Pro Arg Ser Gly Arg Pro Gly Pro Arg

HUMAN CODING SEGMENT E:
                GCC CAG CGC CCC GGC TCC GCC CGC TCG CCG CTG CCG CTG        96
                Ala Gln Arg Pro Gly Ser Ala Arg Ser Pro Leu Pro Leu

CTG CCA CTA CTG CTG CTG CTG GGG ACC GCG CTG GCG CCG GGG GCG    144
                Leu Pro Leu Leu Leu Leu Leu Gly Thr Ala Leu Ala Pro Gly Ala

GCG GCC AAC GAG GCG GCT CCC GCG GGG GCC TCG GTG TGC TAC TCG    192
                Ala Ala Gly Asn Glu Ala Ala Pro Ala Gly Ala Ser Val Cys Tyr Ser

TCC CCC AGC GTG GGA TCG CAG GTG CAG CTA GCT CAG CGC GCC GCG    240
                Ser Pro Ser Val Gly Ser Val Gln Leu Ala Gln Arg Ala Ala

GTG ATC GAG GGA AAG GCG GTG CAC CCG CAG CGG CAG CAG GGG GCA    288
                Val Ile Glu Gly Lys Ala Val His Pro Gln Arg Arg Gln Gln Gly Ala

CTC GAC AGG AAG GCG GCG GCA GGC GAG GCA GGG GCG CTG TGG GGC    336
                Leu Asp Arg Lys Ala Ala Ala Gly Glu Ala Gly Ala Leu Trp Gly

GGC GAT CGC GAG CCG GAG CTC CCA GCC GGC CCA CGG GCG CCC CCC    384
                Gly Asp Arg Glu Pro Glu Leu Pro Pro Ala Gly Pro Arg Ala Leu Gly Pro Pro

GCC GAG GAG CCG CTC CTC GCC GCC AAC GGG ACC GTG CCC TCT TGG CCC    432
                Ala Glu Glu Pro Leu Leu Ala Ala Asn Gly Thr Val Pro Ser Trp Pro

ACC GCC CCG GTG CCC AGC GCC GGC GAG GAG CCC GGG GAG GAG GCG CCC TAT    480
                Thr Ala Pro Val Pro Ser Ala Gly Glu Glu Pro Gly Glu Glu Ala Pro Tyr
```

Fig. 13R

```
CTG GTG AAG GTG CAC CAG GTG TGG GCG GTG AAA GCC GGG GGC TTG AAG    528
Leu Val Lys Val His Gln Val Trp Ala Val Lys Ala Gly Gly Leu Lys

AAG GAC TCG CTG CTC ACC GTG CGC CTG GGG ACC TGG GGC CAC CCC GCC    576
Lys Asp Ser Leu Leu Thr Val Arg Leu Gly Thr Trp Gly His Pro Ala

TTC CCC TCC TGC GGG AGG CTC AAG GAG GAC AGC AGG TAC ATC TTC TTC    624
Phe Pro Ser Cys Gly Arg Leu Lys Glu Asp Ser Arg Tyr Ile Phe Phe

ATG GAG CCC GAC GCC AAC AGC ACC AGC CGC GCG CCG GCC TTC CGA        672
Met Glu Pro Asp Ala Asn Ser Thr Ser Arg Ala Pro Ala Phe Arg

GCC TCT TTC CCC CCT CTG GAG ACG GGC AAC CTC AAG AAG GAG GTC        720
Ala Ser Phe Pro Pro Leu Glu Thr Gly Arg Asn Leu Lys Lys Glu Val

AGC CGG GTG CTG TGC AAG CGG TGC G                                  745
```

Fig. 13R
Continued (SEQ ID NO: 53)
```
AGTTTCCCCC CCCAACTTGT CGGAACTCTG GGCTCGCGCG CAGGGCAGGA GCGGAGCGGC    60

GGCGGCTGCC CAGGCGATGC GAGCGCGGGC CGGACGGTAA TCGCCTCTCC CTCCTCGGGC   120

TGCGAGCGCG CCGGACCGAG GCAGCGACAG GAGCGGACCG CGGCGGGAAC CGAGGACTCC   180

CCAGCGGCGC GCCAGCAGGA GCCACCCCGC GAGCGTGCGA CCGGGACGGA GCGCCCGCCA   240

GTCCCAGGTG GCCCGGACCG CACGTTGCGT CCCCGCGCTC CCCGCCGGCG ACAGGAGACG   300

CTCCCCCCCA CGCCGCGCGC GCCTCGGCCC GGTCGCTGGC CCGCCTCCAC TCCGGGGACA   360

AACTTTTCCC GAAGCCGATC CCAGCCCTCG GACCCAAACT TGTCGCGCGT CGCCTTCGCC   420

GGGAGCCGTC CGCGCAGAGC GTGCACTTCT CGGGCGAG ATG TCG GAG CGC AGA       475
                                         (SEQ ID NO: 54) Met Ser Glu Arg Arg
```

```
GAA GGC AAA GGC AAG GGG AAG GGC GGC AAG AAG GAC CGA GGC TCC GGG    523
Glu Gly Lys Gly Lys Gly Lys Gly Gly Lys Lys Asp Arg Gly Ser Gly

AAG AAG CCC GTG CCC GCG GCT GGC GGC CCG AGC CCA GCC TTG CCT CCC    571
Lys Lys Pro Val Pro Ala Ala Gly Gly Pro Ser Pro Ala Leu Pro Pro

CGC TTG AAA GAG ATG AAG ATG CAG GAG TCT GTG GCA GGT TCC AAA CTA    619
Arg Leu Lys Glu Met Lys Met Gln Glu Ser Val Ala Gly Ser Lys Leu

GTG CTT CGG TGC GAG ACC AGT TCT GAA TAC TCC TCT CTC AAG TTC AAG    667
Val Leu Arg Cys Glu Thr Ser Ser Glu Tyr Ser Ser Leu Lys Phe Lys

TGG TTC AAG AAT GGG AGT GAA TTA AGC CGA AAG AAC AAA CCA CAA AAC    715
Trp Phe Lys Asn Gly Ser Glu Leu Ser Arg Lys Asn Lys Pro Gln Asn

ATC AAG ATA CAG AAA AGG CCG GGG AAG TCA GAA CTT CGC ATT AGC AAA    763
Ile Lys Ile Gln Lys Arg Pro Gly Lys Ser Glu Leu Arg Ile Ser Lys

GCG TCA CTG GCT GAT TCT GGA GAA TAT ATG TGC AAA GTG ATC AGC AAA    811
Ala Ser Leu Ala Asp Ser Gly Glu Tyr Met Cys Lys Val Ile Ser Lys
```

Fig. 14A

```
CTA GGA AAT GAC AGT GCC TCT GCC AAC ATC ACC ATT GTG GAG TCA AAC      859
Leu Gly Asn Asp Ser Ala Ser Ala Asn Ile Thr Ile Val Glu Ser Asn

GAG ATC ACC ACT GGC ATG CCA GCC TCA ACT GAG ACA GCG TAT GTG TCT      907
Glu Ile Thr Thr Gly Met Pro Ala Ser Thr Glu Thr Ala Tyr Val Ser

TCA GAG TCT CCC ATT AGA ATA TCA GTA TCA ACA GAA GGA ACA AAT ACT      955
Ser Glu Ser Pro Ile Arg Ile Ser Val Ser Thr Glu Gly Thr Asn Thr

TCT TCA TCC ACA TCC ACA TCT ACA GCT GGG ACA AGC CAT CTT GTC AAG     1003
Ser Ser Ser Thr Ser Thr Ser Thr Ala Gly Thr Ser His Leu Val Lys

TGT GCA GAG AAG GAG AAA ACT TTC TGT GTG AAT GGA GGC GAG TGC TTC     1051
Cys Ala Glu Lys Glu Lys Thr Phe Cys Val Asn Gly Gly Glu Cys Phe

ATG GTG AAA GAC CTT TCA AAT CCC TCA AGA TAC TTG TGC AAG TGC CCA     1099
Met Val Lys Asp Leu Ser Asn Pro Ser Arg Tyr Leu Cys Lys Cys Pro

AAT GAG TTT ACT GGT GAT CGC TGC CAA AAC TAC GTA ATG GCC AGC TTC     1147
Asn Glu Phe Thr Gly Asp Arg Cys Gln Asn Tyr Val Met Ala Ser Phe

TAC AGT ACG TCC ACT CCC TTT CTG TCT CTG CCT GAA TAGGCGCATG          1193
Tyr Ser Thr Ser Thr Pro Phe Leu Ser Leu Pro Glu

CTCAGTCGGT GCCGCTTTCT TGTTGCCGCA TCTCCCCTCA GATTCAACCT AGAGCTAGAT   1253

GCGTTTTACC AGGTCTAACA TTGACTGCCT CTGCCTGTCG CATGAGAACA TTAACACAAG   1313

CGATTGTATG ACTTCCTCTG TCCGTGACTA GTGGGCTCTG AGCTACTCGT AGGTGCGTAA   1373

GGCTCCAGTG TTTCTGAAAT TGATCTTGAA TTACTGTGAT ACGACATGAT AGTCCCTCTC   1433

ACCCAGTGCA ATGACAATAA AGGCCTTGAA AAGTCTCACT TTTATTGAGA AAATAAAAAT   1493

CGTTCCACGG ACAGTCCCT CTTCTTTATA AAATGACCCT ATCCTTGAAA AGGAGGTGTG    1553

TTAAGTTGTA ACCAGTACAC ACTTGAAATG ATGGTAAGTT CGCTTCGGTT CAGAATGTGT   1613

TCTTTCTGAC AAATAAACAC AATAAAAAAA AAAAAAAAA A                       1654
```

Fig. 14B

```
(SEQ ID NO: 55) CAT CAN GTG TGG GCG GCG AAA GCC GGG GGC TTG AAG AAG GAC TCG CTG     48
(SEQ ID NO: 56) His Gln Val Trp Ala Ala Lys Ala Gly Gly Leu Lys Lys Asp Ser Leu

CTC ACC GTG CGC CTG GGC GCC TGG GGC CAC CCC GCC TTC CCC TCC TGC     96
                Leu Thr Val Arg Leu Gly Ala Trp Gly His Pro Ala Phe Pro Ser Cys

GGG CGC CTC AAG GAG GAC TAC AGC AGG TAC ATC TTC TTC ATG GAG CCC GAG    144
                Gly Arg Leu Lys Glu Asp Tyr Ser Arg Tyr Ile Phe Phe Met Glu Pro Glu

GCC AAC AGC AGC GGC GGG CCC CGC CTT CCG AGC CTC CTT CCC CCC            192
                Ala Asn Ser Ser Gly Gly Pro Arg Leu Pro Ser Leu Leu Pro Pro

TCT CGA GAC GGG CCG GAA CCT CAA GGA GGT CAG CCG GGT GCT GTG            240
                Ser Arg Asp Gly Pro Glu Pro Gln Glu Gly Gln Pro Gly Ala Val

CAA CGG TGC GCC TTG CCT CCC CGC TTG AAA GAG ATG AAG AGT CAG GAG        288
                Gln Arg Cys Ala Leu Pro Pro Arg Leu Lys Glu Met Lys Ser Gln Glu

TCT GTG GCA GGT TCC AAA CTA GTG CTT CGG CTT CTC ACC AGT TCT GAA        336
                Ser Val Ala Gly Ser Lys Leu Val Leu Arg Leu Leu Thr Ser Ser Glu

TAC TCC TCT CTC AAG TTC TGG TTC AAT GGG AGT GAA TTA AGC                384
                Tyr Ser Ser Leu Lys Phe Trp Phe Asn Gly Ser Glu Leu Ser

CGA AAG AAC AAA CCA GAA AAC ATC AAG ATA CAG AAA AGG CCG GGG AAG        432
                Arg Lys Asn Lys Pro Glu Asn Ile Lys Ile Gln Lys Arg Pro Gly Lys

TCA GAA CTT CGC ATT AGC AAA GCG TCA CTG GCT GAT TCT GGA GAA TAT        480
                Ser Glu Leu Arg Ile Ser Lys Ala Ser Leu Ala Asp Ser Gly Glu Tyr

ATG TGC AAA GTG ATC AGC AAA CTA GGA AAT GAC AGT GCC TCT GCC AAC        528
                Met Cys Lys Val Ile Ser Lys Leu Gly Asn Asp Ser Ala Ser Ala Asn
```

Fig. 15A

```
ATC ACC ATT GTG GAG TCA AAC GCC ACA TCC ACA TCT ACA GCT GGG ACA      576
Ile Thr Ile Val Glu Ser Asn Ala Thr Ser Thr Ser Thr Ala Gly Thr

AGC CAT CTT GTC AAG TGT GCA GAG AAG GAG AAA ACT TTC TGT GTG AAT      624
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC      672
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT      720
Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT      768
Val Pro Met Lys Val Gln Thr Gln Glu Lys Cys Pro Asn Glu Phe Thr

GGT GAT CGC TGC CAA AAC TAC GTA ATG GCC AGC TTC TAC AGT ACG TCC      816
Gly Asp Arg Cys Gln Asn Tyr Val Met Ala Ser Phe Tyr Ser Thr Ser

ACT CCC TTT CTG TCT CTG CCT GAA TAGCGCATCT CAGTCGGTGC CGCTTTCTTG     870
Thr Pro Phe Leu Ser Leu Pro Glu

TTGCCGCATC TCCCCTCAGA TTCCNCCTAG AGCTAGATGC GTTTTACCAG GTCTAACATT    930

GACTGCCTCT GCCTGTCGCA TGAGAACATT AACACAAGCG ATTGTATGAC TTCCTCTGTC    990

CGTGACTAGT GGGCTCTGAG CTACTCGTAG GTGCGTAAGG CTCCAGTGTT TCTGAAATTG   1050

ATCTTGAATT ACTGTGATAC GACATGATAG TCCCTCTCAC CCAGTGCAAT GACAATAAAG   1110

GCCTTGAAAA GTCAAAAAAA AAAAAAAAAA                                    1140
```

```
(SEQ ID NO: 57) G AAG TCA GAA CTT CGC ATT AGC AAA GCG TCA CTG GCT GAT TCT GGA GAA    49
(SEQ ID NO: 58)   Lys Ser Glu Leu Arg Ile Ser Lys Ala Ser Leu Ala Asp Ser Gly Glu

TAT ATG TGC AAA GTG ATC AGC AAA CTA GGA AAT GAC AGT GCC TCT GCC                    97
Tyr Met Cys Lys Val Ile Ser Lys Leu Gly Asn Asp Ser Ala Ser Ala

AAC ATC ACC ATT GTG GAG TCA AAC GCC ACA TCC ACA TCT ACA GCT GGG                   145
Asn Ile Thr Ile Val Glu Ser Asn Ala Thr Ser Thr Ser Thr Ala Gly

ACA AGC CAT CTT GTC AAG TGT GCA GAG AAG GAG AAA ACT TTC TGT GTG                   193
Thr Ser His Leu Val Lys Cys Ala Glu Lys Glu Lys Thr Phe Cys Val

AAT GGA GGC GAC TGC TTC ATG GTG AAA GAC CTT TCA AAT CCC TCA AGA                   241
Asn Gly Gly Asp Cys Phe Met Val Lys Asp Leu Ser Asn Pro Ser Arg

TAC TTG TGC AAG TGC CAA CCT GGA TTC ACT GGA GCG AGA TGT GAG                       289
Tyr Leu Cys Lys Cys Gln Pro Gly Phe Thr Gly Ala Arg Cys Thr Glu

AAT GTC CCC ATG AAA GTC CAA ACC ATT ACC GGC ATT TGC TAC GAG GAG CTC TAC           337
Asn Val Pro Met Lys Val Gln Thr Ile Thr Gly Ile Cys Tyr Glu Glu Leu Tyr

CAG AAG AGA GTG CTC ACC ATT GTG GTG GTC CAG AGC CTT CGG AAA ACC AAG CAA CGG       385
Gln Lys Arg Val Leu Thr Ile Val Val Val Gln Ser Leu Arg Lys Thr Lys Gln Arg

GTT GGC ATC ATG TGT TAC TGC CAG AGC CTT CGG CTT GAA AGA AAC                       433
Val Gly Ile Met Cys Tyr Cys Gln Ser Leu Arg Leu Glu Arg Asn

AAA AAG CTT CAT GAC AAC GTA GCC AAC GGG CCC CAC CAC CCC AAT CCG CCC CCC           481
Lys Lys Leu His Asp Asn Val Ala Asn Gly Pro His His Pro Asn Pro Pro Pro

ACC ATG ATG AAC GTA ATG CAA TAC GTA TCT AAA AAT GTC ATC TCT                       529
Thr Met Met Asn Val Met Gln Tyr Val Ser Lys Asn Val Ile Ser

GAG AAC GTG CAG CTG GTG AAT CAA CTG CTG AAT GTG CTG CTC ATC TCT                   577
Glu Asn Val Gln Leu Val Asn Gln Leu Leu Asn Val Leu Leu Ile Ser
```

```
AGC GAG CAT ATT GTT GAG AGA GAG GCG GAG AGC TCT TTT TCC ACC AGT    625
Ser Glu His Ile Val Glu Arg Glu Ala Glu Ser Ser Phe Ser Thr Ser

CAC TAC ACT TCG ACA GCT CAT CAT TCC ACT ACT GTC ACT CAG ACT CCC    673
His Tyr Thr Ser Thr Ala His His Ser Thr Thr Val Thr Gln Thr Pro

AGT CAC AGC TGG AGC AAT GGA CAC ACT GAA AGC ATC ATT TCG GAA AGC    721
Ser His Ser Trp Ser Asn Gly His Thr Glu Ser Ile Ile Ser Glu Ser

CAC TCT GTC ATC GTG ATG TCA TCC GTA GAA AAC AGT AGG CAC AGC AGC    769
His Ser Val Ile Val Met Ser Ser Val Glu Asn Ser Arg His Ser Ser

CCG ACT GGG GGC CCG AGA GGA CGT CTC AAT GGC TTG GGA GGC CCT CGT    817
Pro Thr Gly Gly Pro Arg Gly Arg Leu Asn Gly Leu Gly Gly Pro Arg

GAA TGT AAC AGC TTC CTC AGG CAT GCC AGA GAA ACC CCT GAC TCC TAC    865
Glu Cys Asn Ser Phe Leu Arg His Ala Arg Glu Thr Pro Asp Ser Tyr

CGA GAC TCT CCT CAT AGT GAA AGA CAT AAC CTT ATA GCT GAG CTA AGG    913
Arg Asp Ser Pro His Ser Glu Arg His Asn Leu Ile Ala Glu Leu Arg

AGA AAC AAG GCC CAC AGA TCC AAA TGC ATG CAG ATC CAG CTT TCC GCA    961
Arg Asn Lys Ala His Arg Ser Lys Cys Met Gln Ile Gln Leu Ser Ala

ACT CAT CTT AGA GCT TCT TCC ATT CCC CAT TGG GCT TCA TTC TCT AAG   1009
Thr His Leu Arg Ala Ser Ser Ile Pro His Trp Ala Ser Phe Ser Lys

ACC CCT TGG CCT TTA GGA AGG TAT GTA TCA GCA ATG ACC ACC CCG GCT   1057
Thr Pro Trp Pro Leu Gly Arg Tyr Val Ser Ala Met Thr Thr Pro Ala

CGT ATG TCA CCT GTA GAT TTC CAC ACG CCA AGC TCC CCC AAG TCA CCC   1105
Arg Met Ser Pro Val Asp Phe His Thr Pro Ser Ser Pro Lys Ser Pro

CCT TCG GAA ATG TCC CCG CCC GTG TCC AGC ACG ACG GTC TCC ATG CCC   1153
Pro Ser Glu Met Ser Pro Pro Val Ser Ser Thr Thr Val Ser Met Pro
```

Fig. 16B

```
TCC ATG GCG GTC AGT CCC TTC GTG GAA GAG GAG AGA CCC CTG CTC CTT    1201
Ser Met Ala Val Ser Pro Phe Val Glu Glu Glu Arg Pro Leu Leu Leu

GTG ACG CCA CCA CGG CTG CGG GAG AAG TAT GAC CAC CAC GCC CAG CAA    1249
Val Thr Pro Pro Arg Leu Arg Glu Lys Tyr Asp His His Ala Gln Gln

TTC AAC TCG TTC CAC TGC AAC CCC GCG CAT GAG ACC AAC AGC CTG CCC    1297
Phe Asn Ser Phe His Cys Asn Pro Ala His Glu Thr Asn Ser Leu Pro

CCC AGC CCC TTG AGG ATA GTG GAG GAT GAG GAA TAT GAA ACG ACC CAG    1345
Pro Ser Pro Leu Arg Ile Val Glu Asp Glu Glu Tyr Glu Thr Thr Gln

GAG TAC GAA CCA GCT CAA GAG CCG GTT AAG AAA CTC ACC AAC AGC AGC    1393
Glu Tyr Glu Pro Ala Gln Glu Pro Val Lys Lys Leu Thr Asn Ser Ser

CGG CGG GCC AAA AGA ACC AAG CCC AAT GGT CAC ATT GCC CAC AGG TTG    1441
Arg Arg Ala Lys Arg Thr Lys Pro Asn Gly His Ile Ala His Arg Leu

GAA ATG GAC AAC AAC ACA GGC GCT GAC AGC AGT AAC TCA GAG AGC GAA    1489
Glu Met Asp Asn Asn Thr Gly Ala Asp Ser Ser Asn Ser Glu Ser Glu

ACA GAG GAT GAA AGA GTA GGA GAA GAT ACG CCT TTC CTG GCC ATA CAG    1537
Thr Glu Asp Glu Arg Val Gly Glu Asp Thr Pro Phe Leu Ala Ile Gln

AAC CCC CTG-GCA GCC AGT CTC GAG GCG GCC CCT GCC TTC CGC CTG GTC    1585
Asn Pro Leu Ala Ala Ser Leu Glu Ala Ala Pro Ala Phe Arg Leu Val

GAC AGC AGG ACT AAC CCA ACA GGC GGC TTC TCT CCG CAG GAA GAA TTG    1633
Asp Ser Arg Thr Asn Pro Thr Gly Gly Phe Ser Pro Gln Glu Glu Leu

CAG GCC AGG CTC TCC GGT GTA ATC GCT AAC CAA GAC CCT ATC GCT GTC    1681
Gln Ala Arg Leu Ser Gly Val Ile Ala Asn Gln Asp Pro Ile Ala Val

TAAAACCGAA ATACACCCAT AGATTCACCT GTAAAACTTT ATTTTATATA ATAAAGTATT    1741

CCACCTTAAA TTAAACAAAA AAA                                            1764
```

Fig. 16C

GGF/Heregulin Splicing Variants

| | |
|---|---|
| F-B-A' | F-E-B-A' |
| F-B-A-C-C/D-D | F-E-B-A-C-C/D-D |
| F-B-A-C-C/D-H | F-E-B-A-C-C/D-H |
| F-B-A-C-C/D-H-L | F-E-B-A-C-C/D-H-L |
| F-B-A-C-C/D-H-K-L | F-E-B-A-C-C/D-H-K-L |
| F-B-A-C-C/D-D'-H | F-E-B-A-C-C/D-D'-H |
| F-B-A-C-C/D-D'-H-L | F-E-B-A-C-C/D-D'-H-L |
| F-B-A-C-C/D-D'-H-K-L | F-E-B-A-C-C/D-D'-H-K-L |
| F-B-A-C-C/D'-D | F-E-B-A-C-C/D'-D |
| F-B-A-C-C/D'-H | F-E-B-A-C-C/D'-H |
| F-B-A-C-C/D'-H-L | F-E-B-A-C-C/D'-H-L |
| F-B-A-C-C/D'-H-K-L | F-E-B-A-C-C/D'-H-K-L |
| F-B-A-C-C/D'-D'-H | F-E-B-A-C-C/D'-D'-H |
| F-B-A-C-C/D'-D'-H-L | F-E-B-A-C-C/D'-D'-H-L |
| F-B-A-C-C/D'-D'-H-K-L | F-E-B-A-C-C/D'-D'-H-K-L |
| F-B-A-C-C/D-C/D'-D | F-E-B-A-C-C/D-C/D'-D |
| F-B-A-C-C/D-C/D'-H | F-E-B-A-C-C/D-C/D'-H |
| F-B-A-C-C/D-C/D'-H-L | F-E-B-A-C-C/D-C/D'-H-L |
| F-B-A-C-C/D-C/D'-H-K-L | F-E-B-A-C-C/D-C/D'-H-K-L |
| F-B-A-C-C/D-C/D'-D'-H | F-E-B-A-C-C/D-C/D'-D'-H |
| F-B-A-C-C/D-C/D'-D'-H-L | F-E-B-A-C-C/D-C/D'-D'-H-L |
| F-B-A-C-C/D-C/D'-D'-H-K-L | F-E-B-A-C-C/D-C/D'-D'-H-K-L |
| F-B-A-G-C-C/D-D | F-E-B-A-G-C-C/D-D |
| F-B-A-G-C-C/D-H | F-E-B-A-G-C-C/D-H |
| F-B-A-G-C-C/D-H-L | F-E-B-A-G-C-C/D-H-L |
| F-B-A-G-C-C/D-H-K-L | F-E-B-A-G-C-C/D-H-K-L |
| F-B-A-G-C-C/D-D'-H | F-E-B-A-G-C-C/D-D'-H |
| F-B-A-G-C-C/D-D'-H-L | F-E-B-A-G-C-C/D-D'-H-L |
| F-B-A-G-C-C/D-D'-H-K-L | F-E-B-A-G-C-C/D-D'-H-K-L |
| F-B-A-G-C-C/D'-D | F-E-B-A-G-C-C/D'-D |
| F-B-A-G-C-C/D'-H | F-E-B-A-G-C-C/D'-H |
| F-B-A-G-C-C/D'-H-L | F-E-B-A-G-C-C/D'-H-L |
| F-B-A-G-C-C/D'-H-K-L | F-E-B-A-G-C-C/D'-H-K-L |
| F-B-A-G-C-C/D'-D'-H | F-E-B-A-G-C-C/D'-D'-H |
| F-B-A-G-C-C/D'-D'-H-L | F-E-B-A-G-C-C/D'-D'-H-L |
| F-B-A-G-C-C/D'-D'-H-K-L | F-E-B-A-G-C-C/D'-D'-H-K-L |
| F-B-A-G-C-C/D-C/D'-D | F-E-B-A-G-C-C/D-C/D'-D |
| F-B-A-G-C-C/D-C/D'-H | F-E-B-A-G-C-C/D-C/D'-H |
| F-B-A-G-C-C/D-C/D'-H-L | F-E-B-A-G-C-C/D-C/D'-H-L |
| F-B-A-G-C-C/D-C/D'-H-K-L | F-E-B-A-G-C-C/D-C/D'-H-K-L |
| F-B-A-G-C-C/D-C/D'-D'-H | F-E-B-A-G-C-C/D-C/D'-D'-H |
| F-B-A-G-C-C/D-C/D'-D'-H-L | F-E-B-A-G-C-C/D-C/D'-D'-H-L |
| F-B-A-G-C-C/D-C/D'-D'-H-K-L | F-E-B-A-G-C-C/D-C/D'-D'-H-K-L |

Fig. 17A

GGF/Heregulin
Splicing Variants

```
(SEQ ID NO: 59) AGC CAT CTT GTC AAG TGT GCA GAG AAG GAG AAA ACT TTC TGT GTG AAT   48
(SEQ ID NO: 60) Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC   96
                Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC  144
                Leu Cys Lys Cys Pro Asn Glu Phe Thr Gly Asp Arg Cys Gln Asn Tyr

GTA ATG GCC AGC TTC TAC AGT ACG TCC ACT CCC TTT CTG TCT CTG CCT  192
                Val Met Ala Ser Phe Tyr Ser Thr Ser Thr Pro Phe Leu Ser Leu Pro

GAA TAG                                                         198
                Glu
```

Fig. 18

```
(SEQ ID NO: 61) AGC CAT CTT GTC AAG TGT GCA GAG AAG GAG AAA ACT TTC TGT GTG AAT   48
(SEQ ID NO: 62) Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC   96
                Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT  144
                Leu Cys Lys Cys Gln Pro Gly Phe Thr Gly Ala Arg Cys Thr Glu Asn

GTG CCC ATG AAA GTC CAA ACC CAA GAA AAA GCG GAG GAG CTC TAC TAA  192
                Val Pro Met Lys Val Gln Thr Gln Glu Lys Ala Glu Glu Leu Tyr
```

Fig. 19

```
(SEQ ID NO: 63) AGG CAT CTT GTC AAG TGT GCA GAG AAG GAG AAA ACT TTC TGT GTG AAT    48
(SEQ ID NO: 64) Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
                Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC   144
                Leu Cys Lys Cys Pro Asn Glu Phe Thr Gly Asp Arg Cys Gln Asn Tyr

GTA ATG GCC AGC TTC TAC AAA GCG GAG GAG CTC TAC TAA               183
                Val Met Ala Ser Phe Tyr Lys Ala Glu Glu Leu Tyr
```

Fig. 20

```
(SEQ ID NO: 65) AGC CAT CTT GTC AAG TGT GCA GAG AAG GAG AAA ACT TTC TGT GTG AAT    48
(SEQ ID NO: 66) Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
                Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC   144
                Leu Cys Lys Cys Pro Asn Glu Phe Thr Gly Asp Arg Cys Gln Asn Tyr

GTA ATG GCC AGC TTC TAC AAG CAT CTT GGG ATT GAA TTT ATG GAG AAA   192
                Val Met Ala Ser Phe Tyr Lys His Leu Gly Ile Glu Phe Met Glu Lys

GCG GAG GAG CTC TAC TAA                                           210
                Ala Glu Glu Leu Tyr
```

Fig. 21

(SEQ ID NO: 67) AGC CAT CTT GTC AAG TGT GCA GAG AAG GAG AAA ACT TTC TGT GTG AAT 48
(SEQ ID NO: 68) Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC 96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT 144
Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT 192
Val Pro Met Lys Val Gln Thr Gln Glu Lys Cys Pro Asn Glu Phe Thr

GGT GAT CGC TGC CAA AAC TAC GTA ATG GCC AGC TTC TAC AGT ACG TCC 240
Gly Asp Arg Cys Gln Asn Tyr Val Met Ala Ser Phe Tyr Ser Thr Ser

ACT CCC TTT CTG TCT CTG CCT GAA TAG 267
Thr Pro Phe Leu Ser Leu Pro Glu

Fig. 22

```
(SEQ ID NO: 69) AGC CAT CTT GTC AAG TGT GCA GAG AAG GAG AAA ACT TTC TGT GTG AAT     48
(SEQ ID NO: 70) Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC     96
                Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT    144
                Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT    192
                Val Pro Met Lys Val Gln Thr Gln Glu Lys Cys Pro Asn Glu Phe Thr

GGT GAT CGC TGC CAA AAC TAC GTA ATG GCC AGC TTC TAC AAA GCG GAG    240
                Gly Asp Arg Cys Gln Asn Tyr Val Met Ala Ser Phe Tyr Lys Ala Glu

GAG CTC TAC TAA                                                    252
                Glu Leu Tyr
```

Fig. 23

```
(SEQ ID NO: 71)GGAATTCCTT TTTTTTTTT  TTTTTTTCTT NNTTTTTTT  TGCCCTTATA CCTCTTCGCC    60

TTTCTGTGGT TCCATCCACT TCTTCCCCCT CCTCCTCCCA TAAACAACTC TCCTACCCCT   120

GCACCCCCAA TAAATAAATA AAAGGAGGAG GGCAAGGGGG GAGGAGGAGG AGTGGTGCTG   180

CGAGGGGAAG GAAAAGGGAG GCAGCGCGAG AAGAGCCGGG CAGAGTCCGA ACCGACAGCC   240

AGAAGCCCGC ACGCACCTCG CACC ATG AGA TGG CGA CGC GCC CCG CGC CGC       291
                                      (SEQ ID NO: 72)Met Arg Trp Arg Arg Ala Pro Arg Arg

TCC GGG CGT CCC GGC CCC CGG GCC CAG CGC GGC CGC TCC GCC GCC CGC    339
              Ser Gly Arg Pro Gly Pro Arg Ala Gln Arg Gly Arg Ser Ala Ala Arg

TCG TCG CCG CCG CTG CCG CTG CCA CTA CTG CTG CTG CTG GGG ACC        387
              Ser Ser Pro Pro Leu Pro Leu Pro Leu Leu Leu Leu Leu Gly Thr
                                                       Val Cys Leu Thr Val
                                                       (SEQ ID NO: 83)GGF-II 09

GCG GCC CTG GCG CCG GGG GCG GCC AAC GAG GCG GCT CCC GCG            435
              Ala Ala Leu Ala Pro Gly Ala Ala Asn Glu Ala Ala Pro Ala
              Ala Ala Leu Pro Pro
                             SEQ ID NO: 82)GGF-II 08

GGG GCC TCG GTG TGC TAC TCG TCC CCC AGC GTG GGA TCG GTG CAG        483
              Gly Ala Ser Val Cys Tyr Ser Ser Pro Ser Val Gly Ser Val Gln

GAG CTA GCT CAG CGC|GCC GCG GTG GTG ATC GAG GGA AAG GTG CAC CCG    531
              Glu Leu Ala Gln Ars|Ala Ala Val Val Ile Glu Gly Lys Val His Pro
              Glu Leu Val Gln Arg|Trp Phe Val Ile Glu Gly Lys
                                  (SEQ ID NO: 81)GGF-II 04
```

Fig. 24A

```
CAG CGG CGG CAG CAG GGG GCA CTC GAC AGG AAG GCG GCG GCG GCG                           579
Gln Arg Arg Gln Gln Gly Ala Leu Asp Arg Lys Ala Ala Ala Ala

GGC GAG GGG GCA GGG GCG TGG GGC GGC GAT CGC GAG CCG GAG GGC                           627
Gly Glu Gly Ala Gly Ala Trp Gly Gly Asp Arg Glu Pro Ala Gly

CCA CGG GCG CTG GGG CCG GCC GCC GAG GAG CCG CTG CTC GCC AAC                           675
Pro Arg Ala Leu Gly Pro Ala Ala Glu Glu Pro Leu Leu Ala Asn

GGG ACC GTG CCC TCT TGG CCC ACC GCC CCG GTG CCC AGC GCC GGC GAG                       723
Gly Thr Val Pro Ser Trp Pro Thr Ala Pro Val Pro Ser Ala Gly Glu

CCC GGG GAG GAG GCG CCC TAT CTG GTG AAG GTG CAC CAG GTG TGG GCG                       771
Pro Gly Glu Glu Ala Pro Tyr Leu Val Lys Val His Gln Val Trp Ala
                            (SEQ ID NO: 84)Lys Val His Glu Val Trp Ala
                            (SEQ ID NO: 78)GGF-II 01 & GGF-II 11

GTG AAA GCC GGG GGC TTG AAG AAG GAC TCG CTG CTC ACC GTG CGC CTG                       819
Val Lys Ala Gly Gly Leu Lys Lys Asp Ser Leu Leu Thr Val Arg Leu
Ala Lys                     Asp Leu Leu Leu Xaa Val    Leu(SEQ ID NO: 80)
                                  (SEQ ID NO: 86)GGF-II 10

GGG ACC TGG GGC CAC CCC GCC TTC CCC TCC TGC GGG AGG CTC AAG GAG                       867
Gly Thr Trp Gly His Pro Ala Phe Pro Ser Cys Gly Arg Leu Lys Glu
Gly Ala Trp Gly Pro Pro Ala Phe Pro Val Xaa Tyr
                    (SEQ ID NO: 79)GGF-II 02

GAC AGC AGG TAC ATC TTC TTC ATG GAG CCC GAC GCC AAC AGC ACC AGC                       915
Asp Ser Arg Tyr Ile Phe Phe Met Glu Pro Asp Ala Asn Ser Thr Ser
Tyr Ile Phe Phe Met Glu Pro Gla Ala Xaa Ser Ser Gly
```

Fig. 24B

```
CGC GCG CCG GCC GCC TTC CGA GCC TCT TTC CCC CCT CTG GAG ACG GGC    963
Arg Ala Pro Ala Ala Phe Arg Ala Ser Phe Pro Pro Leu Glu Thr Gly

CGG AAC CTC AAG GAG AAG GTC AGC CGG CTG TGC AAG CGG TGC GCC       1011
Arg Asn Leu Lys Glu Lys Val Ser Arg Leu Cys Lys Arg Cys Ala

TTG CCT CCC CAA TTG AAA GAG ATG AAA AGC CAG GAA TCG GCT GCA GGT   1059
Leu Pro Pro Gln Leu Lys Glu Met Lys Ser Gln Glu Ser Ala Ala Gly

TCC AAA CTA GTC CTT CGG TGT GAA ACC AGT TCT GAA TAC TCC TCT CTC   1107
Ser Lys Leu Val Leu Arg Cys Glu Thr Ser Ser Glu Tyr Ser Ser Leu
                                Leu Val Leu Arg
(SEQ ID NO: 87)GGF-II 06

AGA TTC AAG TGG TTC AAG AAT GGG AAT GAA TTG AAT CGA AAA AAC AAA   1155
Arg Phe Lys Trp Phe Lys Asn Gly Asn Glu Leu Asn Arg Lys Asn Lys

CCA CAA AAT ATC AAG ATA CAA AAG CCA AAG TCA GAA CTT CGC           1203
Pro Gln Asn Ile Lys Ile Gln Lys Pro Gly Lys Ser Glu Leu Arg

ATT AAC AAA GCA TCA CTG GCT GAT TCT GGA GAG TAT ATG TGC AAA GTG   1251
Ile Asn Lys Ala Ser Leu Ala Asp Ser Gly Glu Tyr Met Cys Lys Val
                Lys Ala Ser Leu Ala Asp Ser Gly Tyr Glu Met Xaa Lyx
                        (SEQ ID NO: 85)GGF-II 12

ATC AGC AAA TTA GGA AAT GAC AGT TCT GCC AAT ATC ACC ATC GTG       1299
Ile Ser Lys Leu Gly Asn Asp Ser Ser Ala Asn Ile Thr Ile Val

GAA TCA AAC GCT ACA TCT ACA TCC ACC ACT GGG ACA AGC CAT CTT GTA   1347
Glu Ser Asn Ala Thr Ser Thr Ser Thr Thr Gly Thr Ser His Leu Val
```

Fig. 24C

```
AAA TGT GCG GAG AAG GAG AAA ACT TTC TGT GTG AAT GGA GGG GAG TGC    1395
Lys Cys Ala Glu Lys Glu Lys Thr Phe Cys Val Asn Gly Gly Glu Cys

TTC ATG GTG AAA GAC CTT TCA AAC CCC TCG AGA TAC TTG TGC AAG TGC    1443
Phe Met Val Lys Asp Leu Ser Asn Pro Ser Arg Tyr Leu Cys Lys Cys

CCA AAT GAG TTT ACT GGT GAT CGC TGC CAA AAC TAC GTA ATG GCC AGC    1491
Pro Asn Glu Phe Thr Gly Asp Arg Cys Gln Asn Tyr Val Met Ala Ser

TTC TAC AGT ACG TCC ACT CCC TTT CTG TCT CTG CCT GAA                1530
Phe Tyr Ser Thr Ser Thr Pro Phe Leu Ser Leu Pro Glu

TAGGAGCATG CTCAGTTGGT GCTGCTTTCT TGTTGCTGCA TCTCCCCTCA GATTCCACCT  1590

AGAGCTAGAT GTGTCTTACC AGATCTAATA TTGACTGCCT CTGCCTGTCG CATGAGAACA  1650

TTAACAAAAG CAATTGTATT ACTTCCTCTG TTCGCGACTA GTTGGCTCTG AGATACTAAT  1710

AGGTGTGTGA GGCTCCGGAT GTTTCTGGAA TTGATATTGA ATGATGTGAT ACAAATTGAT  1770

AGTCAATATC AAGCAGTGAA ATATGATAAT AAAGGCATTT CAAAGTCTCA CTTTTATTGA  1830

TAAAATAAAA ATCATTCTAC TGAACAGTCC ATCTTCTTTA TACAATGACC ACATCCTGAA  1890

AAGGGTGTTG CTAAGCTGTA ACCGATATGC ACTTGAAATG ATGGTAAGTT AATTTTGATT  1950

CAGAATGTGT TATTTGTCAC AAATAAACAT AATAAAGGA AAAAAAAAA AAA           2003
```

Fig. 24D

```
(SEQ ID NO: 72) GGFHBS5    1    MRMRRAPRRSGRPGPRAQRPGSAARSSPPLPLIPLLLLLGTAALAPGAAAGNEAAPAGAS
                                                 II-8        II-4
                          61    VCYSSPPSVGSVQELAQRAAVVIEGKVHPQRRQQGALDRKAAAAGEAGAWGGDREPPAA
                                 0                                                II-1        II-10
                         121    GPRALGPPAEEPLLAANGTVPSWPTAPVPSACEPGEEAPYLVKVHQVWAVKAGGLKKDSL
                                                   II-3                 II-2
                         181    LTVRLGTWGHPAFPSCGRLKEDSRYIFFMEPDANSTSRAPAAFRASFPPLETGRNLKKEV
                                                        0                2                              3
                                                                                         ▼         ALPPQLKEMKSQESAAGSK
                         241    SRVLCKRC..........OMSERKEGRGKGKGKKKERGSGKKKPESAAGSQSP             R
                GGFHBS5    1                      O                   R   K       G     D            VP  GP              V
(SEQ ID NO: 73) GGFHFB1    1                                                                                    II-11    I-7, II-12,
(SEQ ID NO: 74) GGFBPP5                                                                   II-14                          III-13
                         268    LVLRCETSSEYSSLRFKNFKNGNELNRKNKPQNIKIQKKPGKSELRINKASLADSGEYMC
                          53                                ▼
                          53    *                        K         S    S              R              S              *
                                      II-6                                             5
                         328    KVISKLGNDSASANITTVESN....EIITGMPASTEGAYVSSESPIRISVSTEGANTSSS       ATSTS
                         113          II-12                                T       T
                         113    4                            ▼                                                   ▼
                                                       6                        II-15                 8
                         354    TTGTSHLVKCAEKEKTFCVNGGECFMVKDLSNPSRYLCKCPNEFTGDRCQNYVMASFYST
                         173          *                                                  *    *    ▼          *
                         173    A                                                                       ----------
                         413    STPFLSLPE*
                         232    ----------
                         232           9
```

Fig. 25

(SEQ ID NO: 72)

```
  1  MRWRRAPRRS GRPGPRAQRP GSAARSSPPL PLLPLLLLLG TAALAPGAAA
 51  GNEAAPAGAS VCYSSPPSVG SVQELAQRAA VVIEGKVKPQ RRQQGALDRK
101  AAAAAGEAGA WGGDREPPAA GPRALGPPAE EPLLAANGTV PSWPTAPVPS
151  AGEPGEEAPY LVKVHQVWAV KAGGLKKDSL LTVRLGTWGH PAFPSCGRLK
201  EDSRYIFFME PDANSTSRAP AAFRASFPPL ETGRNLKKEV SRVLCKRCAL
251  PPQLKEMKSQ ESAAGSKLVL RCETSSEYSS LRFKWFKNGN ELNRKNKPQN
301  IKIQKKPGKS ELRINKASLA DSGEYMCKVI SKLGNDSASA NITIVESNAT
351  STSTTGTSHL VKCAEKEKTF CVNGGECFMV KDLSNPSRYL CKCPNEFTGD
401  RCQNYVMASF YSTSTPFLSL PE*
```

Fig. 26

```
(SEQ ID NO: 76) TCTAA AAC TAC AGA GAC TGT ATT TTC ATG ATC ATC ATA GTT CTG TGA AAT ATA   53
(SEQ ID NO: 77)       Asn Tyr Arg Asp Cys Ile Phe Met Ile Ile Ile Val Leu Xaa Asn Ile

CTT AAA CCG CTT TGG TCC TGA TCT TGT AGG AAG TCA GAA CTT CGC ATT                        101
Leu Lys Pro Leu Trp Ser Xaa Ser Cys Arg Lys Ser Glu Leu Arg Ile

AGC AAA GCG TCA CTG GCT GAT TCT GGA GAA TAT ATG TGC AAA GTG ATC                        149
Ser Lys Ala Ser Leu Ala Asp Ser Gly Glu Tyr Met Cys Lys Val Ile

AGC AAA CTA GGA AAT GAC AGT GCC TCT GCC AAC ATC ACC ATT GTG GAG                        197
Ser Lys Leu Gly Asn Asp Ser Ala Ser Ala Asn Ile Thr Ile Val Glu

TCA AAC GGT AAG AGA TGC CTA CTG CGT GCT ATT TCT CAG TCT CTA AGA                        245
Ser Asn Gly Lys Arg Cys Leu Leu Arg Ala Ile Ser Gln Ser Leu Arg

GGA GTG ATC AAG GTA TGT GGT CAC ACT TGA ATC ACG CAG GTG TGT GAA                        293
Gly Val Ile Lys Val Cys Gly His Thr Xaa Ile Thr Gln Val Cys Glu

ATC TCA TTG TGA ACA AAT CAT GAA AGG AAA CTC TTC ACT CTA TGT TTG                        341
Ile Ser Cys Xaa Thr Asn Lys Asn His Glu Arg Lys Thr Leu Phe Leu

AAA TAT CTT ATG GGT CCT CCT GTA AAG CTC TTC ACT CCA TAA GGT GAA                        389
Lys Tyr Leu Met Gly Pro Pro Val Lys Leu Phe Thr Pro Xaa Gly Glu

ATA GAC CTG AAA TAT ATA TAG ATT ATT T                                                  417
Ile Asp Leu Lys Tyr Ile Xaa Ile Ile
```

Fig. 27

SEQUENCE LISTING

```
<160> NUMBER OF SEQ ID NOS: 87

<210> SEQ ID NO 1
<211> LENGTH: 744
<212> TYPE: DNA
<213> ORGANISM: Bos taurus
<220> FEATURE:
<221> NAME/KEY: CDS
<222> LOCATION: (8)...(625)

<400> SEQUENCE: 1 cctgcag cat caa gtg tgg gcg gcg aaa gcc ggg ggc ttg aag aag gac        49
        His Gln Val Trp Ala Ala Lys Ala Gly Gly Leu Lys Lys Asp
          1               5                  10 tcg ctg ctc acc gtg cgc ctg ggc gcc tgg ggc cac ccc gcc ttc ccc        97
Ser Leu Leu Thr Val Arg Leu Gly Ala Trp Gly His Pro Ala Phe Pro
 15                  20                  25                  30 tcc tgc ggg cgc ctc aag gag gac agc agg tac atc ttc ttc atg gag       145
Ser Cys Gly Arg Leu Lys Glu Asp Ser Arg Tyr Ile Phe Phe Met Glu
                 35                  40                  45 ccc gag gcc aac agc agc ggc ggg ccc ggc cgc ctt ccg agc ctc ctt       193
Pro Glu Ala Asn Ser Ser Gly Gly Pro Gly Arg Leu Pro Ser Leu Leu
             50                  55                  60 ccc ccc tct cga gac ggg ccg gaa cct caa gaa gga ggt cag ccg ggt       241
Pro Pro Ser Arg Asp Gly Pro Glu Pro Gln Glu Gly Gly Gln Pro Gly
         65                  70                  75 gct gtg caa cgg tgc gcc ttg cct ccc cgc ttg aaa gag atg aag agt       289
Ala Val Gln Arg Cys Ala Leu Pro Pro Arg Leu Lys Glu Met Lys Ser
```

```
                80                  85                  90
cag gag tct gtg gca ggt tcc aaa cta gtg ctt cgg tgc gag acc agt      337
Gln Glu Ser Val Ala Gly Ser Lys Leu Val Leu Arg Cys Glu Thr Ser
 95                 100                 105                 110 tct gaa tac tcc tct ctc aag ttc aag tgg ttc aag aat ggg agt gaa      385
Ser Glu Tyr Ser Ser Leu Lys Phe Lys Trp Phe Lys Asn Gly Ser Glu
                115                 120                 125 tta agc cga aag aac aaa cca gaa aac atc aag ata cag aaa agg ccg      433
Leu Ser Arg Lys Asn Lys Pro Glu Asn Ile Lys Ile Gln Lys Arg Pro
            130                 135                 140 ggg aag tca gaa ctt cgc att agc aaa gcg tca ctg gct gat tct gga      481
Gly Lys Ser Glu Leu Arg Ile Ser Lys Ala Ser Leu Ala Asp Ser Gly
        145                 150                 155 gaa tat atg tgc aaa gtg atc agc aaa cta gga aat gac agt gcc tct      529
Glu Tyr Met Cys Lys Val Ile Ser Lys Leu Gly Asn Asp Ser Ala Ser
    160                 165                 170 gcc aac atc acc att gtg gag tca aac ggt aag aga tgc cta ctg cgt      577
Ala Asn Ile Thr Ile Val Glu Ser Asn Gly Lys Arg Cys Leu Leu Arg
175                 180                 185                 190 gct att tct cag tct cta aga gga gtg atc aag gta tgt ggt cac act      625
Ala Ile Ser Gln Ser Leu Arg Gly Val Ile Lys Val Cys Gly His Thr
                195                 200                 205 tgaatcacgc aggtgtgtga aatctcattg tcaacaaata aaaatcatga aaggaaaaaa    685
aaaaaaaaaa aatcgatgtc gactcgagat gtggctgcag gtcgactcta gaggatccc     744

<210> SEQ ID NO 2
<211> LENGTH: 206
<212> TYPE: PRT
<213> ORGANISM: Bos taurus

<400> SEQUENCE: 2

His Gln Val Trp Ala Ala Lys Ala Gly Gly Leu Lys Lys Asp Ser Leu
  1               5                  10                  15

Leu Thr Val Arg Leu Gly Ala Trp Gly His Pro Ala Phe Pro Ser Cys
                 20                  25                  30

Gly Arg Leu Lys Glu Asp Ser Arg Tyr Ile Phe Phe Met Glu Pro Glu
             35                  40                  45

Ala Asn Ser Ser Gly Gly Pro Gly Arg Leu Pro Ser Leu Leu Pro Pro
         50                  55                  60

Ser Arg Asp Gly Pro Glu Pro Gln Glu Gly Gln Pro Gly Ala Val
 65                  70                  75                  80

Gln Arg Cys Ala Leu Pro Pro Arg Leu Lys Glu Met Lys Ser Gln Glu
                 85                  90                  95

Ser Val Ala Gly Ser Lys Leu Val Leu Arg Cys Glu Thr Ser Ser Glu
                100                 105                 110

Tyr Ser Ser Leu Lys Phe Lys Trp Phe Lys Asn Gly Ser Glu Leu Ser
            115                 120                 125

Arg Lys Asn Lys Pro Glu Asn Ile Lys Ile Gln Lys Arg Pro Gly Lys
        130                 135                 140

Ser Glu Leu Arg Ile Ser Lys Ala Ser Leu Ala Asp Ser Gly Glu Tyr
145                 150                 155                 160

Met Cys Lys Val Ile Ser Lys Leu Gly Asn Asp Ser Ala Ser Ala Asn
                165                 170                 175

Ile Thr Ile Val Glu Ser Asn Gly Lys Arg Cys Leu Leu Arg Ala Ile
            180                 185                 190

Ser Gln Ser Leu Arg Gly Val Ile Lys Val Cys Gly His Thr
```

<210> SEQ ID NO 3
<211> LENGTH: 1193
<212> TYPE: DNA
<213> ORGANISM: Bos taurus

<400> SEQUENCE: 3

```
cctgcagcat caagtgtggg cggcgaaagc cggggggcttg aagaaggact cgctgctcac      60
cgtgcgcctg ggcgcctggg gccacccccgc cttcccctcc tgcgggcgcc tcaaggagga     120
cagcaggtac atcttcttca tggagcccga ggccaacagc agcggcgggc ccggccgcct     180
tccgagcctc cttccccccct ctcgagacgg gccggaacct caagaaggag gtcagccggg     240
tgctgtgcaa cggtgcgcct tgcctccccg cttgaaagag atgaagagtc aggagtctgt     300
ggcaggttcc aaactagtgc ttcggtgcga gaccagttct gaatactcct ctctcaagtt     360
caagtggttc aagaatggga gtgaattaag ccgaaagaac aaaccagaaa acatcaagat     420
acagaaaagg ccggggaagt caggacttcg cattagcaaa gcgtcactgg ctgattctgg     480
agaatatatg tgcaaagtga tcagcaaact aggaaatgac agtgcctctg ccaacatcac     540
cattgtggag tcaaacgcca catccacatc tacagctggg acaagccatc ttgtcaagtg     600
tgcagagaag gagaaaactt tctgtgtgaa tggaggcgag tgcttcatgg tgaaagacct     660
ttcaaatccc tcaagatact tgtgcaagtg ccaacctgga ttcactggag cgagatgtac     720
tgagaatgtg cccatgaaag tccaaaccca agaaagtgcc caaatgagtt tactggtgat     780
cgctgccaaa actacgtaat ggccagcttc tacagtacgt ccactccctt tctgtctctg     840
cctgaatagc gcatctcagt cggtgccgct ttcttgttgc cgcatctccc ctcagattcc     900
tcctagagct agatgcgttt taccaggtct aacattgact gcctctgcct gtcgcatgag     960
aacattaaca caagcgattg tatgacttcc tctgtccgtg actagtgggc tctgagctac    1020
tcgtaggtgc gtaaggctcc agtgtttctg aaattgatct tgaattactg tgatacgaca    1080
tgatagtccc tctcacccag tgcaatgaca ataaggcct tgaaaagtca aaaaaaaaa    1140
aaaaaaaaaa aatcgatgtc gactcgagat gtggctgcag gtcgactcta gag          1193
```

<210> SEQ ID NO 4
<211> LENGTH: 263
<212> TYPE: PRT
<213> ORGANISM: Bos taurus

<400> SEQUENCE: 4

```
His Gln Val Trp Ala Ala Lys Ala Gly Gly Leu Lys Lys Asp Ser Leu
  1               5                  10                  15
Leu Thr Val Arg Leu Gly Ala Trp Gly His Pro Ala Phe Pro Ser Cys
             20                  25                  30
Gly Arg Leu Lys Glu Asp Ser Arg Tyr Ile Phe Phe Met Glu Pro Glu
         35                  40                  45
Ala Lys Ser Ser Gly Gly Pro Gly Arg Leu Pro Ser Leu Leu Pro Pro
     50                  55                  60
Ser Arg Asp Gly Pro Glu Pro Gln Glu Gly Gln Pro Gly Ala Val
 65                  70                  75                  80
Gln Arg Cys Ala Leu Pro Pro Arg Leu Lys Glu Met Lys Ser Gln Glu
                 85                  90                  95
Ser Val Ala Gly Ser Lys Leu Val Leu Arg Cys Glu Thr Ser Ser Glu
            100                 105                 110
```

```
Tyr Ser Ser Leu Lys Phe Lys Trp Phe Lys Asn Gly Glu Leu Ser
        115                 120                 125

Arg Lys Asn Lys Gly Gly Asn Ile Lys Ile Gln Lys Arg Pro Gly Lys
130                 135                 140

Ser Gly Leu Arg Ile Ser Lys Ala Ser Leu Ala Asp Ser Gly Glu Tyr
145                 150                 155                 160

Met Cys Lys Val Ile Ser Lys Leu Gly Asn Asp Ser Ala Ser Ala Asn
                165                 170                 175

Ile Thr Ile Val Glu Ser Asn Ala Thr Ser Thr Ser Thr Ala Gly Thr
            180                 185                 190

Ser His Leu Val Lys Ser Ala Glu Lys Glu Lys Thr Phe Cys Val Asn
        195                 200                 205

Gly Gly Glu Cys Phe Met Val Lys Asp Leu Ser Asn Pro Ser Arg Tyr
210                 215                 220

Leu Cys Lys Cys Gln Pro Gly Phe Thr Gly Ala Arg Cys Thr Glu Asn
225                 230                 235                 240

Val Pro Met Lys Val Gln Thr Gln Glu Ser Ala Gln Met Ser Leu Leu
                245                 250                 255

Val Ile Ala Ala Lys Thr Thr
                260

<210> SEQ ID NO 5
<211> LENGTH: 1108
<212> TYPE: DNA
<213> ORGANISM: Bos taurus
<220> FEATURE:
<221> NAME/KEY: CDS
<222> LOCATION: (8)...(778)

<400> SEQUENCE: 5 cctgcag cat caa gtg tgg gcg gcg aaa gcc ggg ggc ttg aag aag gac      49
        His Gln Val Trp Ala Ala Lys Ala Gly Gly Leu Lys Lys Asp
          1               5                  10 tcg ctg ctc acc gtg cgc ctg ggc gcc tgg ggc cac ccc gcc ttc ccc      97
Ser Leu Leu Thr Val Arg Leu Gly Ala Trp Gly His Pro Ala Phe Pro
 15                  20                  25                  30 tcc tgc ggg cgc ctc aag gag gac agc agg tac atc ttc ttc atg gag     145
Ser Cys Gly Arg Leu Lys Glu Asp Ser Arg Tyr Ile Phe Phe Met Glu
                 35                  40                  45 ccc gag gcc aac agc agc ggc ggg ccc ggc cgc ctt ccg agc ctc ctt     193
Pro Glu Ala Asn Ser Ser Gly Gly Pro Gly Arg Leu Pro Ser Leu Leu
             50                  55                  60 ccc ccc tct cga gac ggg ccg gaa cct caa gaa gga ggt cag ccg ggt     241
Pro Pro Ser Arg Asp Gly Pro Glu Pro Gln Glu Gly Gly Gln Pro Gly
         65                  70                  75 gct gtg caa cgg tgc gcc ttg cct ccc cgc ttg aaa gag atg aag agt     289
Ala Val Gln Arg Cys Ala Leu Pro Pro Arg Leu Lys Glu Met Lys Ser
 80                  85                  90 cag gag tct gtg gca ggt tcc aaa cta gtg ctt cgg tgc gag acc agt     337
Gln Glu Ser Val Ala Gly Ser Lys Leu Val Leu Arg Cys Glu Thr Ser
 95                 100                 105                 110 tct gaa tac tcc tct ctc aag ttc aag tgg ttc aag aat ggg agt gaa     385
Ser Glu Tyr Ser Ser Leu Lys Phe Lys Trp Phe Lys Asn Gly Ser Glu
                115                 120                 125 tta agc cga aag aac aaa cca gaa aac atc aag ata cag aaa agg ccg     433
Leu Ser Arg Lys Asn Lys Pro Glu Asn Ile Lys Ile Gln Lys Arg Pro
            130                 135                 140 ggg aag tca gaa ctt cgc att agc aaa gcg tca ctg gct gat tct gga     481
Gly Lys Ser Glu Leu Arg Ile Ser Lys Ala Ser Leu Ala Asp Ser Gly
```

```
                  145                 150                 155
gaa tat atg tgc aaa gtg atc agc aaa cta gga aat gac agt gcc tct      529
Glu Tyr Met Cys Lys Val Ile Ser Lys Leu Gly Asn Asp Ser Ala Ser
    160                 165                 170 gcc aac atc acc att gtg gag tca aac gcc aca tcc aca tct aca gct      577
Ala Asn Ile Thr Ile Val Glu Ser Asn Ala Thr Ser Thr Ser Thr Ala
175                 180                 185                 190 ggg aca agc cat ctt gtc aag tgt gca gag aag gag aaa act ttc tgt      625
Gly Thr Ser His Leu Val Lys Cys Ala Glu Lys Glu Lys Thr Phe Cys
                195                 200                 205 gtg aat gga ggc gag tgc ttc atg gtg aaa gac ctt tca aat ccc tca      673
Val Asn Gly Gly Glu Cys Phe Met Val Lys Asp Leu Ser Asn Pro Ser
    210                 215                 220 aga tac ttg tgc aag tgc cca aat gag ttt act ggt gat cgc tgc caa      721
Arg Tyr Leu Cys Lys Cys Pro Asn Glu Phe Thr Gly Asp Arg Cys Gln
225                 230                 235 aac tac gta atg gcc agc ttc tac agt acg tcc act ccc ttt ctg tct      769
Asn Tyr Val Met Ala Ser Phe Tyr Ser Thr Ser Thr Pro Phe Leu Ser
    240                 245                 250 ctg cct gaa tagcgcatct cagtcggtgc cgctttcttg ttgccgcatc              818
Leu Pro Glu
255 tcccctcaga ttccgcctag agctagatgc gttttaccag gtctaacatt gactgcctct    878 gcctgtcgca tgagaacatt aacacaagcg attgtatgac ttcctctgtc cgtgactagt    938 gggctctgag ctactcgtag gtgcgtaagg ctccagtgtt tctgaaattg atcttgaatt    998 actgtgatac gacatgatag tccctctcac ccagtgcaat gacaataaag gccttgaaaa   1058 gtcaaaaaaa aaaaaaaaaa aaaatcgatg gtcgactcga gatgtggctg              1108

<210> SEQ ID NO 6
<211> LENGTH: 257
<212> TYPE: PRT
<213> ORGANISM: Bos taurus

<400> SEQUENCE: 6

His Gln Val Trp Ala Ala Lys Ala Gly Gly Leu Lys Lys Asp Ser Leu
1               5                   10                  15

Leu Thr Val Arg Leu Gly Ala Trp Gly His Pro Ala Phe Pro Ser Cys
                20                  25                  30

Gly Arg Leu Lys Glu Asp Ser Arg Tyr Ile Phe Phe Met Glu Pro Glu
            35                  40                  45

Ala Asn Ser Ser Gly Gly Pro Gly Arg Leu Pro Ser Leu Leu Pro Pro
        50                  55                  60

Ser Arg Asp Gly Pro Glu Pro Gln Glu Gly Gly Gln Pro Gly Ala Val
65                  70                  75                  80

Gln Arg Cys Ala Leu Pro Pro Arg Leu Lys Glu Met Lys Ser Gln Glu
                85                  90                  95

Ser Val Ala Gly Ser Lys Leu Val Leu Arg Cys Glu Thr Ser Ser Glu
                100                 105                 110

Tyr Ser Ser Leu Lys Phe Lys Trp Phe Lys Asn Gly Ser Glu Leu Ser
            115                 120                 125

Arg Lys Asn Lys Pro Glu Asn Ile Lys Ile Gln Lys Arg Pro Gly Lys
        130                 135                 140

Ser Glu Leu Arg Ile Ser Lys Ala Ser Leu Ala Asp Ser Gly Glu Tyr
145                 150                 155                 160

Met Cys Lys Val Ile Ser Lys Leu Gly Asn Asp Ser Ala Ser Ala Asn
```

```
                    165                 170                 175
Ile Thr Ile Val Glu Ser Asn Ala Thr Ser Thr Ser Thr Ala Gly Thr
                180                 185                 190

Ser His Leu Val Lys Cys Ala Glu Lys Glu Lys Thr Phe Cys Val Asn
            195                 200                 205

Gly Gly Glu Cys Phe Met Val Lys Asp Leu Ser Asn Pro Ser Arg Tyr
        210                 215                 220

Leu Cys Lys Cys Pro Asn Glu Phe Thr Gly Asp Arg Cys Gln Asn Tyr
225                 230                 235                 240

Val Met Ala Ser Phe Tyr Ser Thr Ser Thr Pro Phe Leu Ser Leu Pro
                245                 250                 255

Glu

<210> SEQ ID NO 7
<211> LENGTH: 559
<212> TYPE: DNA
<213> ORGANISM: Bos taurus
<220> FEATURE:
<223> OTHER INFORMATION: N is unknown.

<400> SEQUENCE: 7
agtttccccc cccaacttgt cggaactctg ggctcgcgcg cagggcagga gcggagcggc      60
ggcggctgcc caggcgatgc gagcgcgggc cggacggtaa tcgcctctcc ctcctcgggc     120
tgcgagcgcg ccggaccgag gcagcgacag gagcggaccg cggcgggaac cgaggactcc     180
ccagcggcgc gccagcagga gccaccccgc gagncgtgcg accgggacgg agcgcccgcc     240
agtcccaggt ggcccggacc gcacgttgcg tccccgcgct ccccgccggc gacaggagac     300 gctcccccccc acgccgcgcg cgcctcggcc cggtcgctgg cccgcctcca ctccggggac     360
aaacttttcc cgaagccgat cccagccctc ggacccaaac ttgtcgcgcg tcgccttcgc     420
cgggagccgt ccgcgcagag cgtgcacttc tcgggcgaga tgtcggagcg cagagaaggc     480
aaaggcaagg ggaagggcgg caagaaggac cgaggctccg ggaagaagcc cgtgcccgcg     540
gctggcggcc cgagcccag                                                 559

<210> SEQ ID NO 8
<211> LENGTH: 34
<212> TYPE: PRT
<213> ORGANISM: Bos taurus

<400> SEQUENCE: 8

Met Ser Glu Arg Arg Glu Gly Lys Gly Lys Gly Gly Lys Lys
1               5                   10                  15

Asp Arg Gly Ser Gly Lys Lys Pro Val Pro Ala Ala Gly Gly Pro Ser
            20                  25                  30

Pro Ala

<210> SEQ ID NO 9
<211> LENGTH: 231
<212> TYPE: DNA
<213> ORGANISM: Homo sapiens
<220> FEATURE:
<221> NAME/KEY: CDS
<222> LOCATION: (132)...(231)

<400> SEQUENCE: 9
cgcgagcgcc tcagcgcggc cgctcgctct ccccctcgag ggacaaactt ttcccaaacc      60
cgatccgagc ccttggacca aactcgcctg cgccgagagc cgtccgcgta gagcgctccg     120
```

```
tctccggcga g atg tcc gag cgc aaa gaa ggc aga ggc aaa ggg aag ggc       170
            Met Ser Glu Arg Lys Glu Gly Arg Gly Lys Gly Lys Gly
            1               5                   10 aag aag aag gag cga ggc tcc ggc aag aag ccg gag tcc gcg gcg ggc        218
Lys Lys Lys Glu Arg Gly Ser Gly Lys Lys Pro Glu Ser Ala Ala Gly
 15                  20                  25 agc cag agc cca g                                                       231
Ser Gln Ser Pro
 30
```

<210> SEQ ID NO 10
<211> LENGTH: 33
<212> TYPE: PRT
<213> ORGANISM: Homo sapiens

<400> SEQUENCE: 10

```
Met Ser Glu Arg Lys Glu Gly Arg Gly Lys Gly Lys Lys Lys
 1               5                  10                  15

Glu Arg Gly Ser Gly Lys Lys Pro Glu Ser Ala Ala Gly Ser Gln Ser
             20                  25                  30

Pro
```

<210> SEQ ID NO 11
<211> LENGTH: 252
<212> TYPE: DNA
<213> ORGANISM: Bos taurus
<220> FEATURE:
<221> NAME/KEY: CDS
<222> LOCATION: (3)...(251)
<221> NAME/KEY: variation
<222> LOCATION: (8)...(8)
<223> OTHER INFORMATION: n can be a or g.
<223> OTHER INFORMATION: Xaa is unknown.

<400> SEQUENCE: 11

```
cc cat can gtg tgg gcg gcg aaa gcc ggg ggc ttg aag aag gac tcg        47
   His Xaa Val Trp Ala Ala Lys Ala Gly Gly Leu Lys Lys Asp Ser
   1               5                   10                  15 ctg ctc acc gtg cgc ctg ggc gcc tgg ggc cac ccc gcc ttc ccc tcc        95
Leu Leu Thr Val Arg Leu Gly Ala Trp Gly His Pro Ala Phe Pro Ser
                 20                  25                  30 tgc ggg cgc ctc aag gag gac agc agg tac atc ttc ttc atg gag ccc       143
Cys Gly Arg Leu Lys Glu Asp Ser Arg Tyr Ile Phe Phe Met Glu Pro
             35                  40                  45 gag gcc aac agc agc ggc ggg ccc ggc cgc ctt ccg agc ctc ctt ccc       191
Glu Ala Asn Ser Ser Gly Gly Pro Gly Arg Leu Pro Ser Leu Leu Pro
         50                  55                  60 ccc tct cga gac ggg ccg gaa cct caa gaa gga ggt cag ccg ggt gct       239
Pro Ser Arg Asp Gly Pro Glu Pro Gln Glu Gly Gly Gln Pro Gly Ala
     65                  70                  75 gtg caa cgg tgc g                                                      252
Val Gln Arg Cys
 80
```

<210> SEQ ID NO 12
<211> LENGTH: 83
<212> TYPE: PRT
<213> ORGANISM: Bos taurus

<400> SEQUENCE: 12

```
His Gln Val Trp Ala Ala Lys Ala Gly Gly Leu Lys Lys Asp Ser Leu
 1               5                  10                  15
```

```
Leu Thr Val Arg Leu Gly Ala Trp Gly His Pro Ala Phe Pro Ser Cys
        20                  25                  30

Gly Arg Leu Lys Glu Asp Ser Arg Tyr Ile Phe Phe Met Glu Pro Glu
            35                  40                  45

Ala Asn Ser Ser Gly Gly Pro Gly Arg Leu Pro Ser Leu Leu Pro Pro
 50                  55                  60

Ser Arg Asp Gly Pro Glu Pro Gln Glu Gly Gly Gln Pro Gly Ala Val
 65                  70                  75                  80

Gln Arg Cys

<210> SEQ ID NO 13
<211> LENGTH: 178
<212> TYPE: DNA
<213> ORGANISM: Bos taurus

<400> SEQUENCE: 13
ccttgcctcc ccgcttgaaa gagatgaaga gtcaggagtc tgtggcaggt tccaaactag      60
tgcttcggtg cgagaccagt tctgaatact cctctctcaa gttcaagtgg ttcaagaatg    120
ggagtgaatt aagccgaaag aacaaaccac aaaacatcaa gatacagaaa aggccggg     178

<210> SEQ ID NO 14
<211> LENGTH: 59
<212> TYPE: PRT
<213> ORGANISM: Bos taurus

<400> SEQUENCE: 14

Leu Pro Pro Arg Leu Lys Glu His Lys Ser Gln Glu Ser Val Ala Gly
 1               5                  10                  15

Ser Lys Leu Val Leu Arg Cys Glu Thr Ser Ser Glu Tyr Ser Ser Leu
            20                  25                  30

Lys Phe Lys Trp Phe Lys Asn Gly Ser Glu Leu Ser Arg Lys Asn Lys
        35                  40                  45

Pro Gly Asn Ile Lys Ile Gln Lys Arg Pro Gly
    50                  55

<210> SEQ ID NO 15
<211> LENGTH: 178
<212> TYPE: DNA
<213> ORGANISM: Homo sapiens
<220> FEATURE:
<221> NAME/KEY: CDS
<222> LOCATION: (3)...(178)

<400> SEQUENCE: 15 cc ttg cct ccc cga ttg aaa gag atg aaa agc cag gaa tcg gct gca       47
   Leu Pro Pro Arg Leu Lys Glu Met Lys Ser Gln Glu Ser Ala Ala
    1               5                  10                  15 ggt tcc aaa cta gtc ctt cgg tgt gaa acc agt tct gaa tac tcc tct      95
Gly Ser Lys Leu Val Leu Arg Cys Glu Thr Ser Ser Glu Tyr Ser Ser
                20                  25                  30 ctc aga ttc aag tgg ttc aag aat ggg aat gaa ttg aat cga aaa aac     143
Leu Arg Phe Lys Trp Phe Lys Asn Gly Asn Glu Leu Asn Arg Lys Asn
            35                  40                  45 aaa cca caa aat atc aag ata caa aaa aag cca gg                      178
Lys Pro Gln Asn Ile Lys Ile Gln Lys Lys Pro
        50                  55

<210> SEQ ID NO 16
<211> LENGTH: 58
<212> TYPE: PRT
```

```
<213> ORGANISM: Homo sapiens

<400> SEQUENCE: 16

Leu Pro Pro Arg Leu Lys Glu Met Lys Ser Gln Glu Ser Ala Ala Gly
  1               5                  10                  15

Ser Lys Leu Val Leu Arg Cys Glu Thr Ser Ser Glu Tyr Ser Ser Leu
             20                  25                  30

Arg Phe Lys Trp Phe Lys Asn Gly Asn Glu Leu Asn Arg Lys Asn Lys
         35                  40                  45

Pro Gln Asn Ile Lys Ile Gln Lys Pro
     50                  55

<210> SEQ ID NO 17
<211> LENGTH: 122
<212> TYPE: DNA
<213> ORGANISM: Bos taurus
<220> FEATURE:
<221> NAME/KEY: CDS
<222> LOCATION: (2)...(121)

<400> SEQUENCE: 17 g aag tca gaa ctt cgc att agc aaa gcg tca ctg gct gat tct gga gaa    49
  Lys Ser Glu Leu Arg Ile Ser Lys Ala Ser Leu Ala Asp Ser Gly Glu
   1               5                  10                  15 tat atg tgc aaa gtg atc agc aaa cta gga aat gac agt gcc tct gcc     97
Tyr Met Cys Lys Val Ile Ser Lys Leu Gly Asn Asp Ser Ala Ser Ala
             20                  25                  30 aac atc acc att gtg gag tca aac g                                   122
Asn Ile Thr Ile Val Glu Ser Asn
             35                  40

<210> SEQ ID NO 18
<211> LENGTH: 41
<212> TYPE: PRT
<213> ORGANISM: Bos taurus

<400> SEQUENCE: 18

Lys Ser Glu Leu Arg Ile Ser Lys Ala Ser Leu Ala Asp Ser Gly Glu
  1               5                  10                  15

Tyr Met Cys Lys Val Ile Ser Lys Leu Gly Asn Asp Ser Ala Ser Ala
             20                  25                  30

Asn Ile Thr Ile Val Glu Ser Asn Ala
         35                  40

<210> SEQ ID NO 19
<211> LENGTH: 122
<212> TYPE: DNA
<213> ORGANISM: Homo sapiens
<220> FEATURE:
<221> NAME/KEY: CDS
<222> LOCATION: (2)...(122)

<400> SEQUENCE: 19 g aag tca gaa ctt cgc att aac aaa gca tca ctg gct gat tct gga gag    49
  Lys Ser Glu Leu Arg Ile Asn Lys Ala Ser Leu Ala Asp Ser Gly Glu
   1               5                  10                  15 tat atg tgc aaa gtg atc agc aaa tta gga aat gac agt gcc tct gcc     97
Tyr Met Cys Lys Val Ile Ser Lys Leu Gly Asn Asp Ser Ala Ser Ala
             20                  25                  30 aat atc acc atc gtg gaa tca aac g                                   122
Asn Ile Thr Ile Val Glu Ser Asn
             35                  40
```

-continued

<210> SEQ ID NO 20
<211> LENGTH: 41
<212> TYPE: PRT
<213> ORGANISM: Homo sapiens

<400> SEQUENCE: 20

Lys Ser Glu Leu Arg Ile Asn Lys Ala Ser Leu Ala Asp Ser Gly Glu
 1               5                  10                  15

Tyr Met Cys Lys Val Ile Ser Lys Leu Gly Asn Asp Ser Ala Ser Ala
             20                  25                  30

Asn Ile Thr Ile Val Glu Ser Asn Ala
         35                  40

<210> SEQ ID NO 21
<211> LENGTH: 417
<212> TYPE: DNA
<213> ORGANISM: Bos taurus
<220> FEATURE:
<221> NAME/KEY: CDS
<222> LOCATION: (84)...(272)

<400> SEQUENCE: 21
tctaaaacta cagagactgt attttcatga tcatcatagt tctgtgaaat atacttaaac      60
cgctttggtc ctgatcttgt agg aag tca gaa ctt cgc att agc aaa gcg tca    113
                         Lys Ser Glu Leu Arg Ile Ser Lys Ala Ser
                          1               5                  10 ctg gct gat tct gga gaa tat atg tgc aaa gtg atc agc aaa cta gga     161
Leu Ala Asp Ser Gly Glu Tyr Met Cys Lys Val Ile Ser Lys Leu Gly
             15                  20                  25 aat gac agt gcc tct gcc aac atc acc att gtg gag tca aac ggt aag     209
Asn Asp Ser Ala Ser Ala Asn Ile Thr Ile Val Glu Ser Asn Gly Lys
         30                  35                  40 aga tgc cta ctg cgt gct att tct cag tct cta aga gga gtg atc aag     257
Arg Cys Leu Leu Arg Ala Ile Ser Gln Ser Leu Arg Gly Val Ile Lys
     45                  50                  55 gta tgt ggt cac act tgaatcacgc aggtgtgtga atctcattg tgaacaaata      312
Val Cys Gly His Thr
     60 aaaatcatga aggaaaact ctatgtttga aatatcttat gggtcctcct gtaaagctct    372 tcactccata aggtgaaata gacctgaaat atatatagat tattt                   417

<210> SEQ ID NO 22
<211> LENGTH: 63
<212> TYPE: PRT
<213> ORGANISM: Bos taurus & Homo sapiens

<400> SEQUENCE: 22

Lys Ser Glu Leu Arg Ile Ser Lys Ala Ser Leu Ala Asp Ser Gly Glu
 1               5                  10                  15

Tyr Met Cys Lys Val Ile Ser Lys Leu Gly Asn Asp Ser Ala Ser Ala
             20                  25                  30

Asn Ile Thr Ile Val Glu Ser Asn Gly Lys Arg Cys Leu Leu Arg Ala
         35                  40                  45

Ile Ser Gln Ser Leu Arg Gly Val Ile Lys Val Cys Gly His Thr
     50                  55                  60

<210> SEQ ID NO 23
<211> LENGTH: 102
<212> TYPE: DNA
<213> ORGANISM: Bos taurus

```
<220> FEATURE:
<221> NAME/KEY: CDS
<222> LOCATION: (3)...(101)

<400> SEQUENCE: 23 ag atc acc act ggc atg cca gcc tca act gag aca gcg tat gtg tct      47
   Ile Thr Thr Gly Met Pro Ala Ser Thr Glu Thr Ala Tyr Val Ser
    1               5                  10                  15 tca gag tct ccc att aga ata tca gta tca aca gaa gga aca aat act     95
Ser Glu Ser Pro Ile Arg Ile Ser Val Ser Thr Glu Gly Thr Asn Thr
                20                  25                  30 tct tca t                                                          102
Ser Ser

<210> SEQ ID NO 24
<211> LENGTH: 35
<212> TYPE: PRT
<213> ORGANISM: Bos taurus

<400> SEQUENCE: 24

Glu Ile Thr Thr Gly Met Pro Ala Ser Thr Glu Thr Ala Tyr Val Ser
 1               5                  10                  15

Ser Glu Ser Pro Ile Arg Ile Ser Val Ser Thr Glu Gly Thr Asn Thr
                20                  25                  30

Ser Ser Ser
        35

<210> SEQ ID NO 25
<211> LENGTH: 102
<212> TYPE: DNA
<213> ORGANISM: Homo sapiens
<220> FEATURE:
<221> NAME/KEY: CDS
<222> LOCATION: (1)...(60)

<400> SEQUENCE: 25 aga tca tca ctg gta tgc cag cct caa ctg aag gag cat atg tgt ctt     48
Arg Ser Ser Leu Val Cys Gln Pro Gln Leu Lys Glu His Met Cys Leu
 1               5                  10                  15 cag agt ctc cca ttagaatatc agtatccaca gaaggagcaa atacttcttc        100
Gln Ser Leu Pro
            20 at                                                                 102

<210> SEQ ID NO 26
<211> LENGTH: 35
<212> TYPE: PRT
<213> ORGANISM: Homo sapiens

<400> SEQUENCE: 26

Glu Ile Ile Thr Gly Met Pro Ala Ser Thr Glu Gly Ala Tyr Val Ser
 1               5                  10                  15

Ser Glu Ser Pro Ile Arg Ile Ser Val Ser Thr Glu Gly Thr Asn Thr
                20                  25                  30

Ser Ser Ser
        35

<210> SEQ ID NO 27
<211> LENGTH: 128
<212> TYPE: DNA
<213> ORGANISM: Bos taurus
<220> FEATURE:
<221> NAME/KEY: CDS
```

<222> LOCATION: (3)...(125)

<400> SEQUENCE: 27

```
cc aca tcc aca tct aca gct ggg aca agc cat ctt gtc aag tgt gca         47
   Thr Ser Thr Ser Thr Ala Gly Thr Ser His Leu Val Lys Cys Ala
   1               5                  10                  15 gag aag gag aaa act ttc tgt gtg aat gga ggc gag tgc ttc atg gtg        95
Glu Lys Glu Lys Thr Phe Cys Val Asn Gly Gly Glu Cys Phe Met Val
                20                  25                  30 aaa gac ctt tca aat ccc tca aga tac ttg tgc                           128
Lys Asp Leu Ser Asn Pro Ser Arg Tyr Leu
                35                  40
```

<210> SEQ ID NO 28
<211> LENGTH: 42
<212> TYPE: PRT
<213> ORGANISM: Bos taurus

<400> SEQUENCE: 28

```
Thr Ser Thr Ser Thr Ala Gly Thr Ser His Leu Val Lys Cys Ala Glu
1               5                  10                  15

Lys Glu Lys Thr Phe Cys Val Asn Gly Gly Glu Cys Phe Met Val Lys
                20                  25                  30

Asp Leu Ser Asn Pro Ser Arg Tyr Leu Cys
                35                  40
```

<210> SEQ ID NO 29
<211> LENGTH: 128
<212> TYPE: DNA
<213> ORGANISM: Homo sapiens
<220> FEATURE:
<221> NAME/KEY: CDS
<222> LOCATION: (3)...(128)

<400> SEQUENCE: 29

```
ct aca tct aca tcc acc act ggg aca agc cat ctt gta aaa tgt gcg         47
   Thr Ser Thr Ser Thr Thr Gly Thr Ser His Leu Val Lys Cys Ala
   1               5                  10                  15 gag aag gag aaa act ttc tgt gtg aat gga ggg gag tgc ttc atg gtg        95
Glu Lys Glu Lys Thr Phe Cys Val Asn Gly Gly Glu Cys Phe Met Val
                20                  25                  30 aaa gac ctt tca aac ccc tcg aga tac ttg tgc                           128
Lys Asp Leu Ser Asn Pro Ser Arg Tyr Leu Cys
                35                  40
```

<210> SEQ ID NO 30
<211> LENGTH: 42
<212> TYPE: PRT
<213> ORGANISM: Homo sapiens

<400> SEQUENCE: 30

```
Thr Ser Thr Ser Thr Thr Gly Thr Ser His Leu Val Lys Cys Ala Glu
1               5                  10                  15

Lys Glu Lys Thr Phe Cys Val Asn Gly Gly Glu Cys Phe Met Val Lys
                20                  25                  30

Asp Leu Ser Asn Pro Ser Arg Tyr Leu Cys
                35                  40
```

<210> SEQ ID NO 31
<211> LENGTH: 69
<212> TYPE: DNA
<213> ORGANISM: Bos taurus
<220> FEATURE:

```
<221> NAME/KEY: CDS
<222> LOCATION: (1)...(69)

<400> SEQUENCE: 31 aag tgc caa cct gga ttc act gga gcg aga tgt act gag aat gtg ccc      48
Lys Cys Gln Pro Gly Phe Thr Gly Ala Arg Cys Thr Glu Asn Val Pro
 1               5                  10                  15 atg aaa gtc caa acc caa gaa                                          69
Met Lys Val Gln Thr Gln Glu
             20

<210> SEQ ID NO 32
<211> LENGTH: 23
<212> TYPE: PRT
<213> ORGANISM: Bos taurus

<400> SEQUENCE: 32

Lys Cys Gln Pro Gly Phe Thr Gly Ala Arg Cys Thr Glu Asn Val Pro
 1               5                  10                  15

Met Lys Val Gln Thr Gln Glu
             20

<210> SEQ ID NO 33
<211> LENGTH: 69
<212> TYPE: DNA
<213> ORGANISM: Homo sapiens
<220> FEATURE:
<221> NAME/KEY: CDS
<222> LOCATION: (1)...(69)

<400> SEQUENCE: 33 aag tgc caa cct gga ttc act gga gca aga tgt act gag aat gtg ccc      48
Lys Cys Gln Pro Gly Phe Thr Gly Ala Arg Cys Thr Glu Asn Val Pro
 1               5                  10                  15 atg aaa gtc caa aac caa gaa                                          69
Met Lys Val Gln Asn Gln Glu
             20

<210> SEQ ID NO 34
<211> LENGTH: 23
<212> TYPE: PRT
<213> ORGANISM: Homo sapiens

<400> SEQUENCE: 34

Lys Cys Gln Pro Gly Phe Thr Gly Ala Arg Cys Thr Glu Asn Val Pro
 1               5                  10                  15

Met Lys Val Gln Asn Gln Glu
             20

<210> SEQ ID NO 35
<211> LENGTH: 60
<212> TYPE: DNA
<213> ORGANISM: Bos taurus and Homo sapiens
<220> FEATURE:
<221> NAME/KEY: CDS
<222> LOCATION: (1)...(60)

<400> SEQUENCE: 35 aag tgc cca aat gag ttt act ggt gat cgc tgc caa aac tac gta atg      48
Lys Cys Pro Asn Glu Phe Thr Gly Asp Arg Cys Gln Asn Tyr Val Met
 1               5                  10                  15 gcc agc ttc tac                                                      60
Ala Ser Phe Tyr
             20
```

```
<210> SEQ ID NO 36
<211> LENGTH: 20
<212> TYPE: PRT
<213> ORGANISM: Bos taurus & Homo sapiens

<400> SEQUENCE: 36

Lys Cys Pro Asn Glu Phe Thr Gly Asp Arg Cys Gln Asn Tyr Val Met
 1               5                  10                  15

Ala Ser Phe Tyr
            20

<210> SEQ ID NO 37
<211> LENGTH: 36
<212> TYPE: DNA
<213> ORGANISM: Bos taurus and Homo sapiens

<400> SEQUENCE: 37
agtacgtcca ctcccttcct gtctctgcct gaatag                              36

<210> SEQ ID NO 38
<211> LENGTH: 11
<212> TYPE: PRT
<213> ORGANISM: Bos taurus & Homo sapiens

<400> SEQUENCE: 38

Ser Thr Ser Thr Pro Phe Leu Ser Leu Pro Glu
 1               5                  10

<210> SEQ ID NO 39
<211> LENGTH: 27
<212> TYPE: DNA
<213> ORGANISM: Homo sapiens
<220> FEATURE:
<221> NAME/KEY: CDS
<222> LOCATION: (1)...(27)

<400> SEQUENCE: 39 aag cat ctt ggg att gaa ttt atg gag                                  27
Lys His Leu Gly Ile Glu Phe Met Glu
 1               5

<210> SEQ ID NO 40
<211> LENGTH: 9
<212> TYPE: PRT
<213> ORGANISM: Homo sapiens

<400> SEQUENCE: 40

Lys His Leu Gly Ile Glu Phe Met Glu
 1               5

<210> SEQ ID NO 41
<211> LENGTH: 569
<212> TYPE: DNA
<213> ORGANISM: Bos taurus
<220> FEATURE:
<221> NAME/KEY: CDS
<222> LOCATION: (1)...(565)

<400> SEQUENCE: 41 aaa gcg gag gag ctc tac cag aag aga gtg ctc acc att acc ggc att      48
Lys Ala Glu Glu Leu Tyr Gln Lys Arg Val Leu Thr Ile Thr Gly Ile
 1               5                  10                  15 tgc atc gcg ctg ctc gtg gtt ggc atc atg tgt gtg gtg gtc tac tgc      96
Cys Ile Ala Leu Leu Val Val Gly Ile Met Cys Val Val Val Tyr Cys
            20                  25                  30
```

```
aaa acc aag aaa caa cgg aaa aag ctt cat gac cgg ctt cgg cag agc      144
Lys Thr Lys Lys Gln Arg Lys Lys Leu His Asp Arg Leu Arg Gln Ser
         35                  40                  45 ctt cgg tct gaa aga aac acc atg atg aac gta gcc aac ggg ccc cac      192
Leu Arg Ser Glu Arg Asn Thr Met Met Asn Val Ala Asn Gly Pro His
 50                  55                  60 cac ccc aat ccg ccc ccc gag aac gtg cag ctg gtg aat caa tac gta      240
His Pro Asn Pro Pro Pro Glu Asn Val Gln Leu Val Asn Gln Tyr Val
 65                  70                  75                  80 tct aaa aat gtc atc tct agc gag cat att gtt gag aga gag gcg gag      288
Ser Lys Asn Val Ile Ser Ser Glu His Ile Val Glu Arg Glu Ala Glu
                     85                  90                  95 agc tct ttt tcc acc agt cac tac act tcg aca gct cat cat tcc act      336
Ser Ser Phe Ser Thr Ser His Tyr Thr Ser Thr Ala His His Ser Thr
                100                 105                 110 act gtc act cag act ccc agt cac agc tgg agc aat gga cac act gaa      384
Thr Val Thr Gln Thr Pro Ser His Ser Trp Ser Asn Gly His Thr Glu
            115                 120                 125 agc atc att tcg gaa agc cac tct gtc atc gtg atg tca tcc gta gaa      432
Ser Ile Ile Ser Glu Ser His Ser Val Ile Val Met Ser Ser Val Glu
        130                 135                 140 aac agt agg cac agc agc ccg act ggg ggc ccg aga gga cgt ctc aat      480
Asn Ser Arg His Ser Ser Pro Thr Gly Gly Pro Arg Gly Arg Leu Asn
145                 150                 155                 160 ggc ttg gga ggc cct cgt gaa tgt aac agc ttc ctc agg cat gcc aga      528
Gly Leu Gly Gly Pro Arg Glu Cys Asn Ser Phe Leu Arg His Ala Arg
                165                 170                 175 gaa acc cct gac tcc tac cga gac tct cct cat agt g aaag              569
Glu Thr Pro Asp Ser Tyr Arg Asp Ser Pro His Ser
                180                 185

<210> SEQ ID NO 42
<211> LENGTH: 190
<212> TYPE: PRT
<213> ORGANISM: Bos taurus

<400> SEQUENCE: 42

Lys Ala Glu Glu Leu Tyr Gln Lys Arg Val Leu Thr Ile Thr Gly Ile
 1               5                  10                  15

Cys Ile Ala Leu Leu Val Val Gly Ile Met Cys Val Val Val Tyr Cys
             20                  25                  30

Lys Thr Lys Lys Gln Arg Lys Lys Leu His Asp Arg Leu Arg Gln Ser
         35                  40                  45

Leu Arg Ser Glu Arg Asn Thr Met Met Asn Val Ala Asn Gly Pro His
 50                  55                  60

His Pro Asn Pro Pro Pro Glu Asn Val Gln Leu Val Asn Gln Tyr Val
 65                  70                  75                  80

Ser Lys Asn Val Ile Ser Ser Glu His Ile Val Glu Arg Glu Ala Glu
                     85                  90                  95

Ser Ser Phe Ser Thr Ser His Tyr Thr Ser Thr Ala His His Ser Thr
                100                 105                 110

Thr Val Thr Gln Thr Pro Ser His Ser Trp Ser Asn Gly His Thr Glu
            115                 120                 125

Ser Ile Ile Ser Glu Ser His Ser Val Ile Val Met Ser Ser Val Glu
        130                 135                 140

Asn Ser Arg His Ser Ser Pro Thr Gly Gly Pro Arg Gly Arg Leu Asn
145                 150                 155                 160
```

```
Gly Leu Gly Gly Pro Arg Glu Cys Asn Ser Phe Leu Arg His Ala Arg
                165                 170                 175

Glu Thr Pro Asp Ser Tyr Arg Asp Ser Pro His Ser Glu Arg
            180                 185                 190
```

<210> SEQ ID NO 43
<211> LENGTH: 569
<212> TYPE: DNA
<213> ORGANISM: Homo sapiens
<220> FEATURE:
<221> NAME/KEY: CDS
<222> LOCATION: (1)...(569)

<400> SEQUENCE: 43

```
aag gcg gag gag ctg tac cag aag aga gtg ctg acc ata acc ggc atc       48
Lys Ala Glu Glu Leu Tyr Gln Lys Arg Val Leu Thr Ile Thr Gly Ile
 1               5                  10                  15 tgc atc gcc ctc ctt gtg gtc ggc atc atg tgt gtg gtg gcc tac tgc       96
Cys Ile Ala Leu Leu Val Val Gly Ile Met Cys Val Val Ala Tyr Cys
                20                  25                  30 aaa acc aag aaa cag cgg aaa aag ctg cat gac cgt ctt cgg cag agc      144
Lys Thr Lys Lys Gln Arg Lys Lys Leu His Asp Arg Leu Arg Gln Ser
            35                  40                  45 ctt cgg tct gaa cga aac aat atg atg aac att gcc aat ggg cct cac      192
Leu Arg Ser Glu Arg Asn Asn Met Met Asn Ile Ala Asn Gly Pro His
 50                  55                  60 cat cct aac cca ccc ccc gag aat gtc cag ctg gtg aat caa tac gta      240
His Pro Asn Pro Pro Pro Glu Asn Val Gln Leu Val Asn Gln Tyr Val
 65                  70                  75                  80 tct aaa aac gtc atc tcc agt gag cat att gtt gag aga gaa gca gag      288
Ser Lys Asn Val Ile Ser Ser Glu His Ile Val Glu Arg Glu Ala Glu
                85                  90                  95 aca tcc ttt tcc acc agt cac tat act tcc aca gcc cat cac tcc act      336
Thr Ser Phe Ser Thr Ser His Tyr Thr Ser Thr Ala His His Ser Thr
            100                 105                 110 act gtc acc cag act cct agc cac agc tgg agc aac gga cac act gaa      384
Thr Val Thr Gln Thr Pro Ser His Ser Trp Ser Asn Gly His Thr Glu
        115                 120                 125 agc atc ctt tcc gaa agc cac tct gta atc gtg atg tca tcc gta gaa      432
Ser Ile Leu Ser Glu Ser His Ser Val Ile Val Met Ser Ser Val Glu
    130                 135                 140 aac agt agg cac agc agc cca act ggg ggc cca aga gga cgt ctt aat      480
Asn Ser Arg His Ser Ser Pro Thr Gly Gly Pro Arg Gly Arg Leu Asn
145                 150                 155                 160 ggc aca gga ggc cct cgt gaa tgt aac agc ttc ctc agg cat gcc aga      528
Gly Thr Gly Gly Pro Arg Glu Cys Asn Ser Phe Leu Arg His Ala Arg
                165                 170                 175 gaa acc cct gat tcc tac cga gac tct cct cat agt gaa ag              569
Glu Thr Pro Asp Ser Tyr Arg Asp Ser Pro His Ser Glu
            180                 185
```

<210> SEQ ID NO 44
<211> LENGTH: 190
<212> TYPE: PRT
<213> ORGANISM: Homo sapiens

<400> SEQUENCE: 44

```
Lys Ala Glu Glu Leu Tyr Gln Lys Arg Val Leu Thr Ile Thr Gly Ile
 1               5                  10                  15

Cys Ile Ala Leu Leu Val Val Gly Ile Met Cys Val Val Ala Tyr Cys
                20                  25                  30
```

```
Lys Thr Lys Lys Gln Arg Lys Lys Leu His Asp Arg Leu Arg Gln Ser
            35                  40                  45

Leu Arg Ser Glu Arg Asn Asn Met Met Asn Ile Ala Asn Gly Pro His
 50                  55                  60

His Pro Asn Pro Pro Glu Asn Val Gln Leu Val Asn Gln Tyr Val
 65              70                  75                  80

Ser Lys Asn Val Ile Ser Ser Glu His Ile Val Glu Arg Glu Ala Glu
                 85                  90                  95

Thr Ser Phe Ser Thr Ser His Tyr Thr Ser Thr Ala His His Ser Thr
            100                 105                 110

Thr Val Thr Gln Thr Pro Ser His Ser Trp Ser Asn Gly His Thr Glu
            115                 120                 125

Ser Ile Leu Ser Glu Ser His Ser Val Ile Val Met Ser Ser Val Glu
            130                 135                 140

Asn Ser Arg His Ser Ser Pro Thr Gly Gly Pro Arg Gly Arg Leu Asn
145                 150                 155                 160

Gly Thr Gly Gly Pro Arg Glu Cys Asn Ser Phe Leu Arg His Ala Arg
                165                 170                 175

Glu Thr Pro Asp Ser Tyr Arg Asp Ser Pro His Ser Glu Arg
            180                 185                 190

<210> SEQ ID NO 45
<211> LENGTH: 141
<212> TYPE: DNA
<213> ORGANISM: Bos taurus
<220> FEATURE:
<221> NAME/KEY: CDS
<222> LOCATION: (2)...(139)

<400> SEQUENCE: 45 a cat aac ctt ata gct gag cta agg aga aac aag gcc cac aga tcc aaa      49
  His Asn Leu Ile Ala Glu Leu Arg Arg Asn Lys Ala His Arg Ser Lys
    1               5                  10                  15 tgc atg cag atc cag ctt tcc gca act cat ctt aga gct tct tcc att        97
Cys Met Gln Ile Gln Leu Ser Ala Thr His Leu Arg Ala Ser Ser Ile
             20                  25                  30 ccc cat tgg gct tca ttc tct aag acc cct tgg cct tta gga               139
Pro His Trp Ala Ser Phe Ser Lys Thr Pro Trp Pro Leu Gly
         35                  40                  45 ag                                                                     141

<210> SEQ ID NO 46
<211> LENGTH: 47
<212> TYPE: PRT
<213> ORGANISM: Homo sapiens

<400> SEQUENCE: 46

His Asn Leu Ile Ala Glu Leu Arg Arg Asn Lys Ala His Arg Ser Lys
  1               5                  10                  15

Cys Met Gln Ile Gln Leu Ser Ala Thr His Leu Arg Ala Ser Ser Ile
             20                  25                  30

Pro His Trp Ala Ser Phe Ser Lys Thr Pro Trp Pro Leu Gly Arg
         35                  40                  45

<210> SEQ ID NO 47
<211> LENGTH: 730
<212> TYPE: DNA
<213> ORGANISM: Bos taurus
<220> FEATURE:
<221> NAME/KEY: CDS
```

<222> LOCATION: (2)...(652)

<400> SEQUENCE: 47

```
  g tat gta tca gca atg acc acc ccg gct cgt atg tca cct gta gat ttc    49
    Tyr Val Ser Ala Met Thr Thr Pro Ala Arg Met Ser Pro Val Asp Phe
    1               5                  10                  15 cac acg cca agc tcc ccc aag tca ccc cct tcg gaa atg tcc ccg ccc        97
His Thr Pro Ser Ser Pro Lys Ser Pro Pro Ser Glu Met Ser Pro Pro
                20                  25                  30 gtg tcc agc acg acg gtc tcc atg ccc tcc atg gcg gtc agt ccc ttc       145
Val Ser Ser Thr Thr Val Ser Met Pro Ser Met Ala Val Ser Pro Phe
            35                  40                  45 gtg gaa gag gag aga ccc ctg ctc ctt gtg acg cca cca cgg ctg cgg       193
Val Glu Glu Glu Arg Pro Leu Leu Leu Val Thr Pro Pro Arg Leu Arg
 50                  55                  60 gag aag tat gac cac cac gcc cag caa ttc aac tcg ttc cac tgc aac       241
Glu Lys Tyr Asp His His Ala Gln Gln Phe Asn Ser Phe His Cys Asn
 65                  70                  75                  80 ccc gcg cat gag agc aac agc ctg ccc ccc agc ccc ttg agg ata gtg       289
Pro Ala His Glu Ser Asn Ser Leu Pro Pro Ser Pro Leu Arg Ile Val
                85                  90                  95 gag gat gag gaa tat gaa acg acc cag gag tac gaa cca gct caa gag       337
Glu Asp Glu Glu Tyr Glu Thr Thr Gln Glu Tyr Glu Pro Ala Gln Glu
            100                 105                 110 ccg gtt aag aaa ctc acc aac agc agc cgg cgg gcc aaa aga acc aag       385
Pro Val Lys Lys Leu Thr Asn Ser Ser Arg Arg Ala Lys Arg Thr Lys
        115                 120                 125 ccc aat ggt cac att gcc cac agg ttg gaa atg gac aac aac aca ggc       433
Pro Asn Gly His Ile Ala His Arg Leu Glu Met Asp Asn Asn Thr Gly
130                 135                 140 gct gac agc agt aac tca gag agc gaa aca gag gat gaa aga gta gga       481
Ala Asp Ser Ser Asn Ser Glu Ser Glu Thr Glu Asp Glu Arg Val Gly
145                 150                 155                 160 gaa gat acg cct ttc ctg gcc ata cag aac ccc ctg gca gcc agt ctc       529
Glu Asp Thr Pro Phe Leu Ala Ile Gln Asn Pro Leu Ala Ala Ser Leu
                165                 170                 175 gag gcg gcc cct gcc ttc cgc ctg gtc gac agc agg act aac cca aca       577
Glu Ala Ala Pro Ala Phe Arg Leu Val Asp Ser Arg Thr Asn Pro Thr
            180                 185                 190 ggc ggc ttc tct ccg cag gaa gaa ttg cag gcc agg ctc tcc ggt gta       625
Gly Gly Phe Ser Pro Gln Glu Glu Leu Gln Ala Arg Leu Ser Gly Val
        195                 200                 205 atc gct aac caa gac cct atc gct gtc taaaaccgaa atacacccat             672
Ile Ala Asn Gln Asp Pro Ile Ala Val
210                 215 agattcacct gtaaaacttt attttatata ataaagtatt ccaccttaaa ttaaacaa      730
```

<210> SEQ ID NO 48
<211> LENGTH: 217
<212> TYPE: PRT
<213> ORGANISM: Bos taurus

<400> SEQUENCE: 48

```
Tyr Val Ser Ala Met Thr Thr Pro Ala Arg Met Ser Pro Val Asp Phe
1               5                  10                  15

His Thr Pro Ser Ser Pro Lys Ser Pro Pro Ser Glu Met Ser Pro Pro
            20                  25                  30

Val Ser Ser Thr Thr Val Ser Met Pro Ser Met Ala Val Ser Pro Phe
        35                  40                  45
```

```
Val Glu Glu Arg Pro Leu Leu Val Thr Pro Arg Leu Arg
 50                  55                  60

Glu Lys Tyr Asp His His Ala Gln Gln Phe Asn Ser Phe His Cys Asn
 65                  70                  75                  80

Pro Ala His Glu Ser Asn Ser Leu Pro Pro Ser Pro Leu Arg Ile Val
                 85                  90                  95

Glu Asp Glu Glu Tyr Glu Thr Thr Gln Glu Tyr Glu Pro Ala Gln Glu
            100                 105                 110

Pro Val Lys Lys Leu Thr Asn Ser Ser Arg Arg Ala Lys Arg Thr Lys
            115                 120                 125

Pro Asn Gly His Ile Ala His Arg Leu Glu Met Asp Asn Asn Thr Gly
        130                 135                 140

Ala Asp Ser Ser Asn Ser Glu Ser Glu Thr Glu Asp Glu Arg Val Gly
145                 150                 155                 160

Glu Asp Thr Pro Phe Leu Ala Ile Gln Asn Pro Leu Ala Ala Ser Leu
                165                 170                 175

Glu Ala Ala Pro Ala Phe Arg Leu Val Asp Ser Arg Thr Asn Pro Thr
            180                 185                 190

Gly Gly Phe Ser Pro Gln Gly Glu Leu Gln Ala Arg Leu Ser Gly Val
        195                 200                 205

Ile Ala Asn Gln Asp Pro Ile Ala Val
        210                 215
```

```
<210> SEQ ID NO 49
<211> LENGTH: 730
<212> TYPE: DNA
<213> ORGANISM: Homo sapiens

<400> SEQUENCE: 49
gtatgtgtca gccatgacca ccccggctcg tatgtcacct gtagatttcc acacgccaag      60
ctcccccaaa tcgccccctt cggaaatgtc tccaccctgtg tccagcatga cggtgtccat     120
gccttccatg gcggtcagcc ccttcatgga agaagagaga cctctacttc tcgtgacacc     180
accaaggctg cgggagaaga agtttgacca tcaccctcag cagttcagct ccttccacca     240 caacccccgcg catgacagta acagcctccc tgctagcccc ttgaggatag tggaggatga     300
ggagtatgaa acgacccaag agtacgagcc agcccaagag cctgttaaga aactcgccaa     360
tagccggcgg gccaaaagaa ccaagcccaa tggccacatt gctaacagat tggaagtgga     420
cagcaacaca agctcccaga gcagtaactc agagagtgaa acagaagatg aaagagtagg     480
tgaagatacg cctttcctgg catacagaa ccccctggca gccagtcttg aggcaacacc     540
tgccttccgc ctggctgaca gcaggactaa cccagcaggc cgcttctcga cacaggaaga     600
aatccaggcc aggctgtcta gtgtaattgc taaccaagac cctattgctg tataaaacct     660
aaataaacac atagattcac ctgtaaaact ttatttata taataaagta ttccaccta      720 aattaaacaa                                                            730
```

```
<210> SEQ ID NO 50
<211> LENGTH: 217
<212> TYPE: PRT
<213> ORGANISM: Homo sapiens

<400> SEQUENCE: 50

Tyr Val Ser Ala Met Thr Thr Pro Ala Arg Met Ser Pro Val Asp Phe
  1                5                  10                  15

His Thr Pro Ser Ser Pro Lys Ser Pro Ser Glu Met Ser Pro Pro
```

```
                          20                  25                  30
        Val Ser Ser Met Thr Val Ser Met Pro Ser Met Ala Val Ser Pro Phe
                      35                  40                  45

Met Glu Glu Arg Pro Leu Leu Val Thr Pro Pro Arg Leu Arg
         50                  55                  60

Glu Lys Lys Phe Asp His His Pro Gln Gln Phe Ser Phe His His
         65                  70                  75                  80

Asn Pro Ala His Asp Ser Asn Ser Leu Pro Ala Ser Pro Leu Arg Ile
                          85                  90                  95

Val Glu Asp Glu Glu Tyr Glu Thr Thr Gln Glu Tyr Glu Pro Ala Gln
                         100                 105                 110

Glu Pro Val Lys Lys Leu Ala Asn Ser Arg Arg Ala Lys Arg Thr Lys
                         115                 120                 125

Pro Asn Gly His Ile Ala Asn Arg Leu Glu Val Asp Ser Asn Thr Ser
            130                 135                 140

Ser Gln Ser Ser Asn Ser Glu Ser Glu Thr Glu Asp Glu Arg Val Gly
        145                 150                 155                 160

Glu Asp Thr Pro Phe Leu Gly Ile Gln Asn Pro Leu Ala Ala Ser Leu
                         165                 170                 175

Glu Ala Thr Pro Ala Phe Arg Leu Ala Asp Ser Arg Thr Asn Pro Ala
                     180                 185                 190

Gly Arg Phe Ser Thr Gln Glu Glu Ile Gln Ala Arg Leu Ser Ser Val
                     195                 200                 205

Ile Ala Asn Gln Asp Pro Ile Ala Val
            210                 215

<210> SEQ ID NO 51
<211> LENGTH: 745
<212> TYPE: DNA
<213> ORGANISM: Homo sapiens
<220> FEATURE:
<221> NAME/KEY: CDS
<222> LOCATION: (1)...(744)

<400> SEQUENCE: 51 atg aga tgg cga cgc gcc ccg cgc cgc tcc ggg cgt ccc ggc ccc cgg     48
Met Arg Trp Arg Arg Ala Pro Arg Arg Ser Gly Arg Pro Gly Pro Arg
  1               5                  10                  15 gcc cag cgc ccc ggc tcc gcc gcc cgc tcg tcg ccg ccg ctg ccg ctg     96
Ala Gln Arg Pro Gly Ser Ala Ala Arg Ser Ser Pro Pro Leu Pro Leu
                 20                  25                  30 ctg cca cta ctg ctg ctg ctg ggg acc gcg gcc ctg gcg ccg ggg gcg    144
Leu Pro Leu Leu Leu Leu Leu Gly Thr Ala Ala Leu Ala Pro Gly Ala
             35                  40                  45 gcg gcc ggc aac gag gcg gct ccc gcg ggg gcc tcg gtg tgc tac tcg    192
Ala Ala Gly Asn Glu Ala Ala Pro Ala Gly Ala Ser Val Cys Tyr Ser
         50                  55                  60 tcc ccg ccc agc gtg gga tcg gtg cag gag cta gct cag cgc gcc gcg    240
Ser Pro Pro Ser Val Gly Ser Val Gln Glu Leu Ala Gln Arg Ala Ala
 65                  70                  75                  80 gtg gtg atc gag gga aag gtg cac ccg cag cgg cgg cag cag ggg gca    288
Val Val Ile Glu Gly Lys Val His Pro Gln Arg Arg Gln Gln Gly Ala
                 85                  90                  95 ctc gac agg aag gcg gcg gcg gcg ggc gag gca ggg gcg tgg ggc        336
Leu Asp Arg Lys Ala Ala Ala Ala Gly Glu Ala Gly Ala Trp Gly
                100                 105                 110 ggc gat cgc gag ccg cca gcc gcg ggc cca cgg gcg ctg ggg ccg ccc    384
Gly Asp Arg Glu Pro Pro Ala Ala Gly Pro Arg Ala Leu Gly Pro Pro
```

```
gcc gag gag ccg ctg ctc gcc gcc aac ggg acc gtg ccc tct tgg ccc        432
Ala Glu Glu Pro Leu Leu Ala Ala Asn Gly Thr Val Pro Ser Trp Pro
130                 135                 140 acc gcc ccg gtg ccc agc gcc ggc gag ccc ggg gag gag gcg ccc tat        480
Thr Ala Pro Val Pro Ser Ala Gly Glu Pro Gly Glu Glu Ala Pro Tyr
145                 150                 155                 160 ctg gtg aag gtg cac cag gtg tgg gcg gtg aaa gcc ggg ggc ttg aag        528
Leu Val Lys Val His Gln Val Trp Ala Val Lys Ala Gly Gly Leu Lys
                165                 170                 175 aag gac tcg ctg ctc acc gtg cgc ctg ggg acc tgg ggc cac ccc gcc        576
Lys Asp Ser Leu Leu Thr Val Arg Leu Gly Thr Trp Gly His Pro Ala
            180                 185                 190 ttc ccc tcc tgc ggg agg ctc aag gag gac agc agg tac atc ttc ttc        624
Phe Pro Ser Cys Gly Arg Leu Lys Glu Asp Ser Arg Tyr Ile Phe Phe
        195                 200                 205 atg gag ccc gac gcc aac agc acc agc cgc gcg ccg gcc gcc ttc cga        672
Met Glu Pro Asp Ala Asn Ser Thr Ser Arg Ala Pro Ala Ala Phe Arg
    210                 215                 220 gcc tct ttc ccc cct ctg gag acg ggc cgg aac ctc aag aag gag gtc        720
Ala Ser Phe Pro Pro Leu Glu Thr Gly Arg Asn Leu Lys Lys Glu Val
225                 230                 235                 240 agc cgg gtg ctg tgc aag cgg tgc g                                      745
Ser Arg Val Leu Cys Lys Arg Cys
                245
```

<210> SEQ ID NO 52
<211> LENGTH: 248
<212> TYPE: PRT
<213> ORGANISM: Homo sapiens

<400> SEQUENCE: 52

Met Arg Trp Arg Ala Pro Arg Ser Gly Arg Pro Gly Arg
1               5                   10                  15

Ala Gln Arg Pro Gly Ser Ala Ala Arg Ser Ser Pro Pro Leu Pro Leu
            20                  25                  30

Leu Pro Leu Leu Leu Leu Leu Gly Thr Ala Ala Leu Ala Pro Gly Ala
        35                  40                  45

Ala Ala Gly Asn Glu Ala Ala Pro Ala Gly Ala Ser Val Cys Tyr Ser
    50                  55                  60

Ser Pro Pro Ser Val Gly Ser Val Gln Glu Leu Ala Gln Arg Ala Ala
65                  70                  75                  80

Val Val Ile Glu Gly Lys Val His Pro Gln Arg Arg Gln Gln Gly Ala
                85                  90                  95

Leu Asp Arg Lys Ala Ala Ala Ala Gly Glu Ala Gly Ala Trp Gly
            100                 105                 110

Gly Asp Arg Glu Pro Pro Ala Ala Gly Pro Arg Ala Leu Gly Pro Pro
        115                 120                 125

Ala Glu Glu Pro Leu Leu Ala Ala Asn Gly Thr Val Pro Ser Trp Pro
    130                 135                 140

Thr Ala Pro Val Pro Ser Ala Gly Glu Pro Gly Glu Glu Ala Pro Tyr
145                 150                 155                 160

Leu Val Lys Val His Gln Val Trp Ala Val Lys Ala Gly Gly Leu Lys
                165                 170                 175

Lys Asp Ser Leu Leu Thr Val Arg Leu Gly Thr Trp Gly His Pro Ala
            180                 185                 190

Phe Pro Ser Cys Gly Arg Leu Lys Glu Asp Ser Arg Tyr Ile Phe Phe

```
                     195                 200                     205
Met Glu Pro Asp Ala Asn Ser Thr Ser Arg Ala Pro Ala Ala Phe Arg
            210                 215                 220

Ala Ser Phe Pro Pro Leu Glu Thr Gly Arg Asn Leu Lys Lys Glu Val
225                 230                 235                 240

Ser Arg Val Leu Cys Lys Arg Cys
                245

<210> SEQ ID NO 53
<211> LENGTH: 1652
<212> TYPE: DNA
<213> ORGANISM: Bos taurus
<220> FEATURE:
<221> NAME/KEY: CDS
<222> LOCATION: (459)...(1181)

<400> SEQUENCE: 53
agtttccccc cccaacttgt cggaactctg ggctcgcgcg cagggcagga gcggagcggc        60
ggcggctgcc caggcgatgc gagcgcgggc cggacggtaa tcgcctctcc ctcctcgggc       120
tgcgagcgcg ccggaccgag gcagcgacag gagcggaccg cggcgggaac cgaggactcc       180
ccagcggcgc gccagcagga gccacccccgc gagcgtgcga ccgggacgga gcgcccgcca      240
gtcccaggtg gcccggaccg cacgttgcgt ccccgcgctc cccgccggcg acaggagacg       300
ctccccccca cgccgcgcgc gcctcggccc ggtcgctggc ccgcctccac tccggggaca       360
aacttttccc gaagccgatc ccagccctcg gacccaaact tgtcgcgcgt cgccttcgcc       420
gggagccgtc cgcgcagagc gtgcacttct cgggcgag atg tcg gag cgc aga gaa     476
                                          Met Ser Glu Arg Arg Glu
                                            1               5 ggc aaa ggc aag ggg aag ggc ggc aag aag gac cga ggc tcc ggg aag       524
Gly Lys Gly Lys Gly Lys Gly Gly Lys Lys Asp Arg Gly Ser Gly Lys
            10                  15                  20 aag ccc gtg ccc gcg gct ggc ggc ccg agc cca gcc ttg cct ccc cgc       572
Lys Pro Val Pro Ala Ala Gly Gly Pro Ser Pro Ala Leu Pro Pro Arg
        25                  30                  35 ttg aaa gag atg aag atg cag gag tct gtg gca ggt tcc aaa cta gtg       620
Leu Lys Glu Met Lys Met Gln Glu Ser Val Ala Gly Ser Lys Leu Val
    40                  45                  50 ctt cgg tgc gag acc agt tct gaa tac tcc tct ctc aag ttc aag tgg       668
Leu Arg Cys Glu Thr Ser Ser Glu Tyr Ser Ser Leu Lys Phe Lys Trp
55                  60                  65                  70 ttc aag aat ggg agt gaa tta agc cga aag aac aaa cca caa aac atc       716
Phe Lys Asn Gly Ser Glu Leu Ser Arg Lys Asn Lys Pro Gln Asn Ile
                75                  80                  85 aag ata cag aaa agg ccg ggg aag tca gaa ctt cgc att agc aaa gcg       764
Lys Ile Gln Lys Arg Pro Gly Lys Ser Glu Leu Arg Ile Ser Lys Ala
            90                  95                 100 tca ctg gct gat tct gga gaa tat atg tgc aaa gtg atc agc aaa cta       812
Ser Leu Ala Asp Ser Gly Glu Tyr Met Cys Lys Val Ile Ser Lys Leu
        105                 110                 115 gga aat gac agt gcc tct gcc aac atc acc att gtg gag tca aac gag       860
Gly Asn Asp Ser Ala Ser Ala Asn Ile Thr Ile Val Glu Ser Asn Glu
    120                 125                 130 atc acc act ggc atg cca gcc tca act gag aca gcg tat gtg tct tca       908
Ile Thr Thr Gly Met Pro Ala Ser Thr Glu Thr Ala Tyr Val Ser Ser
135                 140                 145                 150 gag tct ccc att aga ata tca gta tca aca gaa gga aca aat act tct       956
Glu Ser Pro Ile Arg Ile Ser Val Ser Thr Glu Gly Thr Asn Thr Ser
                155                 160                 165
```

```
tca tcc aca tcc aca tct aca gct ggg aca agc cat ctt gtc aag tgt    1004
Ser Ser Thr Ser Thr Ser Thr Ala Gly Thr Ser His Leu Val Lys Cys
            170                 175                 180 gca gag aag gag aaa act ttc tgt gtg aat gga ggc gag tgc ttc atg    1052
Ala Glu Lys Glu Lys Thr Phe Cys Val Asn Gly Gly Glu Cys Phe Met
                185                 190                 195 gtg aaa gac ctt tca aat ccc tca aga tac ttg tgc aag tgc cca aat    1100
Val Lys Asp Leu Ser Asn Pro Ser Arg Tyr Leu Cys Lys Cys Pro Asn
        200                 205                 210 gag ttt act ggt gat cgc tgc caa aac tac gta atg gcc agc ttc tac    1148
Glu Phe Thr Gly Asp Arg Cys Gln Asn Tyr Val Met Ala Ser Phe Tyr
215                 220                 225                 230 agt acg tcc act ccc ttt ctg tct ctg cct gaa taggcgcatg ctcagtcggt  1201
Ser Thr Ser Thr Pro Phe Leu Ser Leu Pro Glu
                235                 240 gccgctttct tgttgccgca tctcccctca gattcaacct agagctagat gcgttttacc  1261
aggtctaaca ttgactgcct ctgcctgtcg catgagaaca ttaacacaag cgattgtatg  1321
acttcctctg tccgtgacta gtgggctctg agctactcgt aggtgcgtaa ggctccagtg  1381
tttctgaaat tgatcttgaa ttactgtgat acgacatgat agtccctctc acccagtgca  1441
atgacaataa aggccttgaa aagtctcact tttattgaga aaataaaaat cgttccacgg  1501
gacagtccct cttctttata aaatgaccct atccttgaaa aggaggtgtg ttaagttgta  1561
accagtacac acttgaaatg atggtaagtt cgcttcggtt cagaatgtgt tctttctgac  1621
aaataaacag aataaaaaaa aaaaaaaaaa a                                  1652

<210> SEQ ID NO 54
<211> LENGTH: 241
<212> TYPE: PRT
<213> ORGANISM: Bos taurus

<400> SEQUENCE: 54

Met Ser Glu Arg Arg Glu Gly Lys Gly Lys Gly Lys Gly Gly Lys Lys
1               5                   10                  15

Asp Arg Gly Ser Gly Lys Lys Pro Val Pro Ala Ala Gly Gly Pro Ser
            20                  25                  30

Pro Ala Leu Pro Pro Arg Leu Lys Glu Met Lys Met Gln Glu Ser Val
        35                  40                  45

Ala Gly Ser Lys Leu Val Leu Arg Cys Glu Thr Ser Ser Glu Tyr Ser
    50                  55                  60

Ser Leu Lys Phe Lys Trp Phe Lys Asn Gly Ser Glu Leu Ser Arg Lys
65                  70                  75                  80

Asn Lys Pro Gln Asn Ile Lys Ile Gln Lys Arg Pro Gly Lys Ser Glu
                85                  90                  95

Leu Arg Ile Ser Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Thr Thr Gly Met Pro Ala Ser Thr Glu
    130                 135                 140

Thr Ala Tyr Val Ser Ser Glu Ser Pro Ile Arg Ile Ser Val Ser Thr
145                 150                 155                 160

Glu Gly Thr Asn Thr Ser Ser Ser Thr Ser Thr Ala Gly Thr
                165                 170                 175

Ser His Leu Val Lys Cys Ala Glu Lys Glu Lys Thr Phe Cys Val Asn
```

-continued

```
                      180                 185                 190
Gly Gly Glu Cys Phe Met Val Lys Asp Leu Ser Asn Pro Ser Arg Tyr
            195                 200                 205

Leu Cys Lys Cys Pro Asn Glu Phe Thr Gly Asp Arg Cys Gln Asn Tyr
            210                 215                 220

Val Met Ala Ser Phe Tyr Ser Thr Ser Thr Pro Phe Leu Ser Leu Pro
225                 230                 235                 240

Glu

<210> SEQ ID NO 55
<211> LENGTH: 1140
<212> TYPE: DNA
<213> ORGANISM: Bos taurus
<220> FEATURE:
<221> NAME/KEY: CDS
<222> LOCATION: (1)...(840)
<223> OTHER INFORMATION: n is unknown.
<223> OTHER INFORMATION: Xaa is unknown.

<400> SEQUENCE: 55 cat can gtg tgg gcg gcg aaa gcc ggg ggc ttg aag aag gac tcg ctg        48
His Xaa Val Trp Ala Ala Lys Ala Gly Gly Leu Lys Lys Asp Ser Leu
  1               5                  10                  15 ctc acc gtg cgc ctg ggc gcc tgg ggc cac ccc gcc ttc ccc tcc tgc        96
Leu Thr Val Arg Leu Gly Ala Trp Gly His Pro Ala Phe Pro Ser Cys
             20                  25                  30 ggg cgc ctc aag gag gac agc agg tac atc ttc ttc atg gag ccc gag       144
Gly Arg Leu Lys Glu Asp Ser Arg Tyr Ile Phe Phe Met Glu Pro Glu
         35                  40                  45 gcc aac agc agc ggc ggg ccc ggc cgc ctt ccg agc ctc ctt ccc ccc       192
Ala Asn Ser Ser Gly Gly Pro Gly Arg Leu Pro Ser Leu Leu Pro Pro
     50                  55                  60 tct cga gac ggg ccg gaa cct caa gaa gga ggt cag ccg ggt gct gtg       240
Ser Arg Asp Gly Pro Glu Pro Gln Glu Gly Gly Gln Pro Gly Ala Val
 65                  70                  75                  80 caa cgg tgc gcc ttg cct ccc cgc ttg aaa gag atg aag agt cag gag       288
Gln Arg Cys Ala Leu Pro Pro Arg Leu Lys Glu Met Lys Ser Gln Glu
                 85                  90                  95 tct gtg gca ggt tcc aaa cta gtg ctt cgg tgc gag acc agt tct gaa       336
Ser Val Ala Gly Ser Lys Leu Val Leu Arg Cys Glu Thr Ser Ser Glu
            100                 105                 110 tac tcc tct ctc aag ttc aag tgg ttc aag aat ggg agt gaa tta agc       384
Tyr Ser Ser Leu Lys Phe Lys Trp Phe Lys Asn Gly Ser Glu Leu Ser
        115                 120                 125 cga aag aac aaa cca gaa aac atc aag ata cag aaa agg ccg ggg aag       432
Arg Lys Asn Lys Pro Glu Asn Ile Lys Ile Gln Lys Arg Pro Gly Lys
    130                 135                 140 tca gaa ctt cgc att agc aaa gcg tca ctg gct gat tct gga gaa tat       480
Ser Glu Leu Arg Ile Ser Lys Ala Ser Leu Ala Asp Ser Gly Glu Tyr
145                 150                 155                 160 atg tgc aaa gtg atc agc aaa cta gga aat gac agt gcc tct gcc aac       528
Met Cys Lys Val Ile Ser Lys Leu Gly Asn Asp Ser Ala Ser Ala Asn
                165                 170                 175 atc acc att gtg gag tca aac gcc aca tcc aca tct aca gct ggg aca       576
Ile Thr Ile Val Glu Ser Asn Ala Thr Ser Thr Ser Thr Ala Gly Thr
            180                 185                 190 agc cat ctt gtc aag tgt gca gag aag gag aaa act ttc tgt gtg aat       624
Ser His Leu Val Lys Cys Ala Glu Lys Glu Lys Thr Phe Cys Val Asn
        195                 200                 205 gga ggc gag tgc ttc atg gtg aaa gac ctt tca aat ccc tca aga tac       672
```

```
Gly Gly Glu Cys Phe Met Val Lys Asp Leu Ser Asn Pro Ser Arg Tyr
        210                 215                 220 ttg tgc aag tgc caa cct gga ttc act gga gcg aga tgt act gag aat       720
Leu Cys Lys Cys Gln Pro Gly Phe Thr Gly Ala Arg Cys Thr Glu Asn
225                 230                 235                 240 gtg ccc atg aaa gtc caa acc caa gaa aag tgc cca aat gag ttt act       768
Val Pro Met Lys Val Gln Thr Gln Glu Lys Cys Pro Asn Glu Phe Thr
                245                 250                 255 ggt gat cgc tgc caa aac tac gta atg gcc agc ttc tac agt acg tcc       816
Gly Asp Arg Cys Gln Asn Tyr Val Met Ala Ser Phe Tyr Ser Thr Ser
            260                 265                 270 act ccc ttt ctg tct ctg cct gaa tagcgcatct cagtcggtgc cgctttcttg      870
Thr Pro Phe Leu Ser Leu Pro Glu
        275                 280 ttgccgcatc tcccctcaga ttccncctag agctagatgc gttttaccag gtctaacatt     930
gactgcctct gcctgtcgca tgagaacatt aacacaagcg attgtatgac ttcctctgtc     990
cgtgactagt gggctctgag ctactcgtag gtgcgtaagg ctccagtgtt tctgaaattg    1050
atcttgaatt actgtgatac gacatgatag tccctctcac ccagtgcaat gacaataaag    1110
gccttgaaaa gtcaaaaaaa aaaaaaaaaa                                     1140

<210> SEQ ID NO 56
<211> LENGTH: 280
<212> TYPE: PRT
<213> ORGANISM: Bos taurus

<400> SEQUENCE: 56

His Gln Val Trp Ala Ala Lys Ala Gly Gly Leu Lys Lys Asp Ser Leu
 1               5                  10                  15

Leu Thr Val Arg Leu Gly Ala Trp Gly His Pro Ala Phe Pro Ser Cys
            20                  25                  30

Gly Arg Leu Lys Glu Asp Ser Arg Tyr Ile Phe Phe Met Glu Pro Glu
        35                  40                  45

Ala Asn Ser Ser Gly Gly Pro Gly Arg Leu Pro Ser Leu Leu Pro Pro
    50                  55                  60

Ser Arg Asp Gly Pro Glu Pro Gln Glu Gly Gly Gln Pro Gly Ala Val
65                  70                  75                  80

Gln Arg Cys Ala Leu Pro Pro Arg Leu Lys Glu Met Lys Ser Gln Glu
                85                  90                  95

Ser Val Ala Gly Ser Lys Leu Val Leu Arg Cys Glu Thr Ser Ser Glu
            100                 105                 110

Tyr Ser Ser Leu Lys Phe Lys Trp Phe Lys Asn Gly Ser Glu Leu Ser
        115                 120                 125

Arg Lys Asn Lys Pro Glu Asn Ile Lys Ile Gln Lys Arg Pro Gly Lys
    130                 135                 140

Ser Glu Leu Arg Ile Ser Lys Ala Ser Leu Ala Asp Ser Gly Glu Tyr
145                 150                 155                 160

Met Cys Lys Val Ile Ser Lys Leu Gly Asn Asp Ser Ala Ser Ala Asn
                165                 170                 175

Ile Thr Ile Val Glu Ser Asn Ala Thr Ser Thr Ser Thr Ala Gly Thr
            180                 185                 190

Ser His Leu Val Lys Cys Ala Glu Lys Glu Lys Thr Phe Cys Val Asn
        195                 200                 205

Gly Gly Glu Cys Phe Met Val Lys Asp Leu Ser Asn Pro Ser Arg Tyr
    210                 215                 220
```

```
Leu Cys Lys Cys Gln Pro Gly Phe Thr Gly Ala Arg Cys Thr Glu Asn
225                 230                 235                 240

Val Pro Met Lys Val Gln Thr Gln Glu Lys Cys Pro Asn Glu Phe Thr
            245                 250                 255

Gly Asp Arg Cys Gln Asn Tyr Val Met Ala Ser Phe Tyr Ser Thr Ser
        260                 265                 270

Thr Pro Phe Leu Ser Leu Pro Glu
    275                 280

<210> SEQ ID NO 57
<211> LENGTH: 1764
<212> TYPE: DNA
<213> ORGANISM: Bos taurus
<220> FEATURE:
<221> NAME/KEY: CDS
<222> LOCATION: (2)...(1681)

<400> SEQUENCE: 57
```

| | | | | | | | | | | | | | | | | |
|---|---|---|---|---|---|---|---|---|---|---|---|---|---|---|---|---|
| g | aag | tca | gaa | ctt | cgc | att | agc | aaa | gcg | tca | ctg | gct | gat | tct | gga | gaa | 49 |
|   | Lys | Ser | Glu | Leu | Arg | Ile | Ser | Lys | Ala | Ser | Leu | Ala | Asp | Ser | Gly | Glu |   |
|   | 1   |     |     | 5   |     |     |     |     | 10  |     |     |     |     | 15  |     |     |   |

```
tat atg tgc aaa gtg atc agc aaa cta gga aat gac agt gcc tct gcc      97
Tyr Met Cys Lys Val Ile Ser Lys Leu Gly Asn Asp Ser Ala Ser Ala
            20                  25                  30 aac atc acc att gtg gag tca aac gcc aca tcc aca tct aca gct ggg     145
Asn Ile Thr Ile Val Glu Ser Asn Ala Thr Ser Thr Ser Thr Ala Gly
        35                  40                  45 aca agc cat ctt gtc aag tgt gca gag aag gag aaa act ttc tgt gtg     193
Thr Ser His Leu Val Lys Cys Ala Glu Lys Glu Lys Thr Phe Cys Val
    50                  55                  60 aat gga ggc gac tgc ttc atg gtg aaa gac ctt tca aat ccc tca aga     241
Asn Gly Gly Asp Cys Phe Met Val Lys Asp Leu Ser Asn Pro Ser Arg
65                  70                  75                  80 tac ttg tgc aag tgc caa cct gga ttc act gga gcg aga tgt act gag     289
Tyr Leu Cys Lys Cys Gln Pro Gly Phe Thr Gly Ala Arg Cys Thr Glu
                85                  90                  95 aat gtg ccc atg aaa gtc caa acc caa gaa aaa gcg gag gag ctc tac     337
Asn Val Pro Met Lys Val Gln Thr Gln Glu Lys Ala Glu Glu Leu Tyr
            100                 105                 110 cag aag aga gtg ctc acc att acc ggc att tgc atc gcg ctg ctc gtg     385
Gln Lys Arg Val Leu Thr Ile Thr Gly Ile Cys Ile Ala Leu Leu Val
        115                 120                 125 gtt ggc atc atg tgt gtg gtg gtc tac tgc aaa acc aag aaa caa cgg     433
Val Gly Ile Met Cys Val Val Val Tyr Cys Lys Thr Lys Lys Gln Arg
    130                 135                 140 aaa aag ctt cat gac cgg ctt cgg cag agc ctt cgg tct gaa aga aac     481
Lys Lys Leu His Asp Arg Leu Arg Gln Ser Leu Arg Ser Glu Arg Asn
145                 150                 155                 160 acc atg atg aac gta gcc aac ggg ccc cac cac ccc aat ccg ccc ccc     529
Thr Met Met Asn Val Ala Asn Gly Pro His His Pro Asn Pro Pro Pro
                165                 170                 175 gag aac gtg cag ctg gtg aat caa tac gta tct aaa aat gtc atc tct     577
Glu Asn Val Gln Leu Val Asn Gln Tyr Val Ser Lys Asn Val Ile Ser
            180                 185                 190 agc gag cat att gtt gag aga gag gcg gag agc tct ttt tcc acc agt     625
Ser Glu His Ile Val Glu Arg Glu Ala Glu Ser Ser Phe Ser Thr Ser
        195                 200                 205 cac tac act tcg aca gct cat cat tcc act act gtc act cag act ccc     673
His Tyr Thr Ser Thr Ala His His Ser Thr Thr Val Thr Gln Thr Pro
    210                 215                 220
```

-continued

| | |
|---|---|
| agt cac agc tgg agc aat gga cac act gaa agc atc att tcg gaa agc<br>Ser His Ser Trp Ser Asn Gly His Thr Glu Ser Ile Ile Ser Glu Ser<br>225                         230                     235                 240 | 721 |
| cac tct gtc atc gtg atg tca tcc gta gaa aac agt agg cac agc agc<br>His Ser Val Ile Val Met Ser Ser Val Glu Asn Ser Arg His Ser Ser<br>                       245                     250                     255 | 769 |
| ccg act ggg ggc ccg aga gga cgt ctc aat ggc ttg gga ggc cct cgt<br>Pro Thr Gly Gly Pro Arg Gly Arg Leu Asn Gly Leu Gly Gly Pro Arg<br>                260                     265                     270 | 817 |
| gaa tgt aac agc ttc ctc agg cat gcc aga gaa acc cct gac tcc tac<br>Glu Cys Asn Ser Phe Leu Arg His Ala Arg Glu Thr Pro Asp Ser Tyr<br>          275                     280                     285 | 865 |
| cga gac tct cct cat agt gaa aga cat aac ctt ata gct gag cta agg<br>Arg Asp Ser Pro His Ser Glu Arg His Asn Leu Ile Ala Glu Leu Arg<br>290                         295                     300 | 913 |
| aga aac aag gcc cac aga tcc aaa tgc atg cag atc cag ctt tcc gca<br>Arg Asn Lys Ala His Arg Ser Lys Cys Met Gln Ile Gln Leu Ser Ala<br>305                         310                     315                     320 | 961 |
| act cat ctt aga gct tct tcc att ccc cat tgg gct tca ttc tct aag<br>Thr His Leu Arg Ala Ser Ser Ile Pro His Trp Ala Ser Phe Ser Lys<br>                       325                     330                     335 | 1009 |
| acc cct tgg cct tta gga agg tat gta tca gca atg acc acc ccg gct<br>Thr Pro Trp Pro Leu Gly Arg Tyr Val Ser Ala Met Thr Thr Pro Ala<br>             340                     345                     350 | 1057 |
| cgt atg tca cct gta gat ttc cac acg cca agc tcc ccc aag tca ccc<br>Arg Met Ser Pro Val Asp Phe His Thr Pro Ser Ser Pro Lys Ser Pro<br>          355                     360                     365 | 1105 |
| cct tcg gaa atg tcc ccg ccc gtg tcc agc acg acg gtc tcc atg ccc<br>Pro Ser Glu Met Ser Pro Pro Val Ser Ser Thr Thr Val Ser Met Pro<br>370                         375                     380 | 1153 |
| tcc atg gcg gtc agt ccc ttc gtg gaa gag gag aga ccc ctg ctc ctt<br>Ser Met Ala Val Ser Pro Phe Val Glu Glu Glu Arg Pro Leu Leu Leu<br>385                         390                     395                     400 | 1201 |
| gtg acg cca cca cgg ctg cgg gag aag tat gac cac cac gcc cag caa<br>Val Thr Pro Pro Arg Leu Arg Glu Lys Tyr Asp His His Ala Gln Gln<br>                       405                     410                     415 | 1249 |
| ttc aac tcg ttc cac tgc aac ccc gcg cat gag agc aac agc ctg ccc<br>Phe Asn Ser Phe His Cys Asn Pro Ala His Glu Ser Asn Ser Leu Pro<br>             420                     425                     430 | 1297 |
| ccc agc ccc ttg agg ata gtg gag gat gag gaa tat gaa acg acc cag<br>Pro Ser Pro Leu Arg Ile Val Glu Asp Glu Glu Tyr Glu Thr Thr Gln<br>          435                     440                     445 | 1345 |
| gag tac gaa cca gct caa gag ccg gtt aag aaa ctc acc aac agc agc<br>Glu Tyr Glu Pro Ala Gln Glu Pro Val Lys Lys Leu Thr Asn Ser Ser<br>450                         455                     460 | 1393 |
| cgg cgg gcc aaa aga acc aag ccc aat ggt cac att gcc cac agg ttg<br>Arg Arg Ala Lys Arg Thr Lys Pro Asn Gly His Ile Ala His Arg Leu<br>465                         470                     475                     480 | 1441 |
| gaa atg gac aac aac aca ggc gct gac agc agt aac tca gag agc gaa<br>Glu Met Asp Asn Asn Thr Gly Ala Asp Ser Ser Asn Ser Glu Ser Glu<br>                       485                     490                     495 | 1489 |
| aca gag gat gaa aga gta gga gaa gat acg cct ttc ctg gcc ata cag<br>Thr Glu Asp Glu Arg Val Gly Glu Asp Thr Pro Phe Leu Ala Ile Gln<br>             500                     505                     510 | 1537 |
| aac ccc ctg gca gcc agt ctc gag gcg gcc cct gcc ttc cgc ctg gtc<br>Asn Pro Leu Ala Ala Ser Leu Glu Ala Ala Pro Ala Phe Arg Leu Val<br>          515                     520                     525 | 1585 |
| gac agc agg act aac cca aca ggc ggc ttc tct ccg cag gaa gaa ttg<br>Asp Ser Arg Thr Asn Pro Thr Gly Gly Phe Ser Pro Gln Glu Glu Leu<br>530                         535                     540 | 1633 |

```
cag gcc agg ctc tcc ggt gta atc gct aac caa gac cct atc gct gtc    1681
Gln Ala Arg Leu Ser Gly Val Ile Ala Asn Gln Asp Pro Ile Ala Val
545                 550                 555                 560 taaaaccgaa atacacccat agattcacct gtaaactttt attttatata ataagtatt   1741 ccaccttaaa ttaaacaaaa aaa                                           1764
```

<210> SEQ ID NO 58
<211> LENGTH: 560
<212> TYPE: PRT
<213> ORGANISM: Bos taurus

<400> SEQUENCE: 58

```
Lys Ser Glu Leu Arg Ile Ser Lys Ala Ser Leu Ala Asp Ser Gly Glu
1               5                   10                  15

Tyr Met Cys Lys Val Ile Ser Lys Leu Gly Asn Asp Ser Ala Ser Ala
                20                  25                  30

Asn Ile Thr Ile Val Glu Ser Asn Ala Thr Ser Thr Ser Thr Ala Gly
            35                  40                  45

Thr Ser His Leu Val Lys Cys Ala Glu Lys Glu Lys Thr Phe Cys Val
        50                  55                  60

Asn Gly Gly Asp Cys Phe Met Val Lys Asp Leu Ser Asn Pro Ser Arg
65                  70                  75                  80

Tyr Leu Cys Lys Cys Gln Pro Gly Phe Thr Gly Ala Arg Cys Thr Glu
                85                  90                  95

Asn Val Pro Met Lys Val Gln Thr Gln Glu Lys Ala Glu Glu Leu Tyr
            100                 105                 110

Gln Lys Arg Val Leu Thr Ile Thr Gly Ile Cys Ile Ala Leu Leu Val
        115                 120                 125

Val Gly Ile Met Cys Val Val Tyr Cys Lys Thr Lys Lys Gln Arg
    130                 135                 140

Lys Lys Leu His Asp Arg Leu Arg Gln Ser Leu Arg Ser Glu Arg Asn
145                 150                 155                 160

Thr Met Met Asn Val Ala Asn Gly Pro His His Pro Asn Pro Pro Pro
                165                 170                 175

Glu Asn Val Gln Leu Val Asn Gln Tyr Val Ser Lys Asn Val Ile Ser
            180                 185                 190

Ser Glu His Ile Val Glu Arg Glu Ala Glu Ser Ser Phe Ser Thr Ser
        195                 200                 205

His Tyr Thr Ser Thr Ala His His Ser Thr Thr Val Thr Gln Thr Pro
    210                 215                 220

Ser His Ser Trp Ser Asn Gly His Thr Glu Ser Ile Ile Ser Glu Ser
225                 230                 235                 240

His Ser Val Ile Val Met Ser Ser Val Glu Asn Ser Arg His Ser Ser
                245                 250                 255

Pro Thr Gly Gly Pro Arg Gly Arg Leu Asn Gly Leu Gly Gly Pro Arg
            260                 265                 270

Glu Cys Asn Ser Phe Leu Arg His Ala Arg Glu Thr Pro Asp Ser Tyr
        275                 280                 285

Arg Asp Ser Pro His Ser Glu Arg His Asn Leu Ile Ala Glu Leu Arg
    290                 295                 300

Arg Asn Lys Ala His Arg Ser Lys Cys Met Gln Ile Gln Leu Ser Ala
305                 310                 315                 320

Thr His Leu Arg Ala Ser Ser Ile Pro His Trp Ala Ser Phe Ser Lys
                325                 330                 335
```

```
Thr Pro Trp Pro Leu Gly Arg Tyr Val Ser Ala Met Thr Thr Pro Ala
            340                 345                 350

Arg Met Ser Pro Val Asp Phe His Thr Pro Ser Ser Pro Lys Ser Pro
        355                 360                 365

Pro Ser Glu Met Ser Pro Val Ser Ser Thr Thr Val Ser Met Pro
    370                 375                 380

Ser Met Ala Val Ser Pro Phe Val Glu Glu Arg Pro Leu Leu Leu
385                 390                 395                 400

Val Thr Pro Pro Arg Leu Arg Glu Lys Tyr Asp His His Ala Gln Gln
                405                 410                 415

Phe Asn Ser Phe His Cys Asn Pro Ala His Glu Ser Asn Ser Leu Pro
            420                 425                 430

Pro Ser Pro Leu Arg Ile Val Glu Asp Glu Glu Tyr Glu Thr Thr Gln
            435                 440                 445

Glu Tyr Glu Pro Ala Gln Glu Pro Val Lys Lys Leu Thr Asn Ser Ser
    450                 455                 460

Arg Arg Ala Lys Arg Thr Lys Pro Asn Gly His Ile Ala His Arg Leu
465                 470                 475                 480

Glu Met Asp Asn Asn Thr Gly Ala Asp Ser Ser Asn Ser Glu Ser Glu
                485                 490                 495

Thr Glu Asp Glu Arg Val Gly Glu Asp Thr Pro Phe Leu Ala Ile Gln
            500                 505                 510

Asn Pro Leu Ala Ala Ser Leu Glu Ala Ala Pro Ala Phe Arg Leu Val
            515                 520                 525

Asp Ser Arg Thr Asn Pro Thr Gly Gly Phe Ser Pro Gln Glu Glu Leu
            530                 535                 540

Gln Ala Arg Leu Ser Gly Val Ile Ala Asn Gln Asp Pro Ile Ala Val
545                 550                 555                 560

<210> SEQ ID NO 59
<211> LENGTH: 198
<212> TYPE: DNA
<213> ORGANISM: Homo sapiens
<220> FEATURE:
<221> NAME/KEY: CDS
<222> LOCATION: (1)...(195)

<400> SEQUENCE: 59 agc cat ctt gtc aag tgt gca gag aag gag aaa act ttc tgt gtg aat      48
Ser His Leu Val Lys Cys Ala Glu Lys Glu Lys Thr Phe Cys Val Asn
 1               5                  10                  15 gga ggc gag tgc ttc atg gtg aaa gac ctt tca aat ccc tca aga tac      96
Gly Gly Glu Cys Phe Met Val Lys Asp Leu Ser Asn Pro Ser Arg Tyr
             20                  25                  30 ttg tgc aag tgc cca aat gag ttt act ggt gat cgc tgc caa aac tac     144
Leu Cys Lys Cys Pro Asn Glu Phe Thr Gly Asp Arg Cys Gln Asn Tyr
         35                  40                  45 gta atg gcc agc ttc tac agt acg tcc act ccc ttt ctg tct ctg cct     192
Val Met Ala Ser Phe Tyr Ser Thr Ser Thr Pro Phe Leu Ser Leu Pro
     50                  55                  60 gaa tag                                                             198

<210> SEQ ID NO 60
<211> LENGTH: 65
<212> TYPE: PRT
<213> ORGANISM: Homo sapiens

<400> SEQUENCE: 60
```

```
Ser His Leu Val Lys Cys Ala Glu Lys Glu Lys Thr Phe Cys Val Asn
 1               5                  10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
             35                  40                  45

Val Met Ala Ser Phe Tyr Ser Thr Ser Thr Pro Phe Leu Ser Leu Pro
    50                  55                  60

Glu
65

<210> SEQ ID NO 61
<211> LENGTH: 192
<212> TYPE: DNA
<213> ORGANISM: Homo sapiens
<220> FEATURE:
<221> NAME/KEY: CDS
<222> LOCATION: (1)...(189)

<400> SEQUENCE: 61 agc cat ctt gtc aag tgt gca gag aag gag aaa act ttc tgt gtg aat      48
Ser His Leu Val Lys Cys Ala Glu Lys Glu Lys Thr Phe Cys Val Asn
 1               5                  10                  15 gga ggc gag tgc ttc atg gtg aaa gac ctt tca aat ccc tca aga tac      96
Gly Gly Glu Cys Phe Met Val Lys Asp Leu Ser Asn Pro Ser Arg Tyr
            20                  25                  30 ttg tgc aag tgc caa cct gga ttc act gga gcg aga tgt act gag aat     144
Leu Cys Lys Cys Gln Pro Gly Phe Thr Gly Ala Arg Cys Thr Glu Asn
             35                  40                  45 gtg ccc atg aaa gtc caa acc caa gaa aaa gcg gag gag ctc tac         189
Val Pro Met Lys Val Gln Thr Gln Glu Lys Ala Glu Glu Leu Tyr
    50                  55                  60 taa                                                                  192

<210> SEQ ID NO 62
<211> LENGTH: 63
<212> TYPE: PRT
<213> ORGANISM: Homo sapiens

<400> SEQUENCE: 62

Ser His Leu Val Lys Cys Ala Glu Lys Glu Lys Thr Phe Cys Val Asn
 1               5                  10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
             35                  40                  45

Val Pro Met Lys Val Gln Thr Gln Glu Lys Ala Glu Glu Leu Tyr
    50                  55                  60

<210> SEQ ID NO 63
<211> LENGTH: 183
<212> TYPE: DNA
<213> ORGANISM: Homo sapiens
<220> FEATURE:
<221> NAME/KEY: CDS
<222> LOCATION: (1)...(180)

<400> SEQUENCE: 63 agc cat ctt gtc aag tgt gca gag aag gag aaa act ttc tgt gtg aat      48
Ser His Leu Val Lys Cys Ala Glu Lys Glu Lys Thr Phe Cys Val Asn
 1               5                  10                  15
```

```
gga ggc gag tgc ttc atg gtg aaa gac ctt tca aat ccc tca aga tac      96
Gly Gly Glu Cys Phe Met Val Lys Asp Leu Ser Asn Pro Ser Arg Tyr
         20                  25                  30 ttg tgc aag tgc cca aat gag ttt act ggt gat cgc tgc caa aac tac     144
Leu Cys Lys Cys Pro Asn Glu Phe Thr Gly Asp Arg Cys Gln Asn Tyr
         35                  40                  45 gta atg gcc agc ttc tac aaa gcg gag gag ctc tac taa                 183
Val Met Ala Ser Phe Tyr Lys Ala Glu Glu Leu Tyr
 50                  55                  60

<210> SEQ ID NO 64
<211> LENGTH: 60
<212> TYPE: PRT
<213> ORGANISM: Homo sapiens

<400> SEQUENCE: 64

Ser His Leu Val Lys Cys Ala Glu Lys Glu Lys Thr Phe Cys Val Asn
 1               5                  10                  15

Gly Gly Glu Cys Phe Met Val Lys Asp Leu Ser Asn Pro Ser Arg Tyr
         20                  25                  30

Leu Cys Lys Cys Pro Asn Glu Phe Thr Gly Asp Arg Cys Gln Asn Tyr
         35                  40                  45

Val Met Ala Ser Phe Tyr Lys Ala Glu Glu Leu Tyr
 50                  55                  60

<210> SEQ ID NO 65
<211> LENGTH: 210
<212> TYPE: DNA
<213> ORGANISM: Homo sapiens
<220> FEATURE:
<221> NAME/KEY: CDS
<222> LOCATION: (1)...(207)

<400> SEQUENCE: 65 agc cat ctt gtc aag tgt gca gag aag gag aaa act ttc tgt gtg aat      48
Ser His Leu Val Lys Cys Ala Glu Lys Glu Lys Thr Phe Cys Val Asn
 1               5                  10                  15 gga ggc gag tgc ttc atg gtg aaa gac ctt tca aat ccc tca aga tac      96
Gly Gly Glu Cys Phe Met Val Lys Asp Leu Ser Asn Pro Ser Arg Tyr
         20                  25                  30 ttg tgc aag tgc cca aat gag ttt act ggt gat cgc tgc caa aac tac     144
Leu Cys Lys Cys Pro Asn Glu Phe Thr Gly Asp Arg Cys Gln Asn Tyr
         35                  40                  45 gta atg gcc agc ttc tac aag cat ctt ggg att gaa ttt atg gag aaa     192
Val Met Ala Ser Phe Tyr Lys His Leu Gly Ile Glu Phe Met Glu Lys
 50                  55                  60 gcg gag gag ctc tac taa                                             210
Ala Glu Glu Leu Tyr
 65

<210> SEQ ID NO 66
<211> LENGTH: 69
<212> TYPE: PRT
<213> ORGANISM: Homo sapiens

<400> SEQUENCE: 66

Ser His Leu Val Lys Cys Ala Glu Lys Glu Lys Thr Phe Cys Val Asn
 1               5                  10                  15

Gly Gly Glu Cys Phe Met Val Lys Asp Leu Ser Asn Pro Ser Arg Tyr
         20                  25                  30

Leu Cys Lys Cys Pro Asn Glu Phe Thr Gly Asp Arg Cys Gln Asn Tyr
```

```
                    35                  40                  45
Val Met Ala Ser Phe Tyr Lys His Leu Gly Ile Glu Phe Met Glu Lys
    50                  55                  60

Ala Glu Glu Leu Tyr
65

<210> SEQ ID NO 67
<211> LENGTH: 267
<212> TYPE: DNA
<213> ORGANISM: Homo sapiens
<220> FEATURE:
<221> NAME/KEY: CDS
<222> LOCATION: (1)...(264)

<400> SEQUENCE: 67 agc cat ctt gtc aag tgt gca gag aag gag aaa act ttc tgt gtg aat      48
Ser His Leu Val Lys Cys Ala Glu Lys Glu Lys Thr Phe Cys Val Asn
1               5                  10                  15 gga ggc gag tgc ttc atg gtg aaa gac ctt tca aat ccc tca aga tac      96
Gly Gly Glu Cys Phe Met Val Lys Asp Leu Ser Asn Pro Ser Arg Tyr
                20                  25                  30 ttg tgc aag tgc caa cct gga ttc act gga gcg aga tgt act gag aat     144
Leu Cys Lys Cys Gln Pro Gly Phe Thr Gly Ala Arg Cys Thr Glu Asn
            35                  40                  45 gtg ccc atg aaa gtc caa acc caa gaa aag tgc cca aat gag ttt act     192
Val Pro Met Lys Val Gln Thr Gln Glu Lys Cys Pro Asn Glu Phe Thr
        50                  55                  60 ggt gat cgc tgc caa aac tac gta atg gcc agc ttc tac agt acg tcc     240
Gly Asp Arg Cys Gln Asn Tyr Val Met Ala Ser Phe Tyr Ser Thr Ser
65                  70                  75                  80 act ccc ttt ctg tct ctg cct gaa tag                                  267
Thr Pro Phe Leu Ser Leu Pro Glu
                85

<210> SEQ ID NO 68
<211> LENGTH: 88
<212> TYPE: PRT
<213> ORGANISM: Homo sapiens

<400> SEQUENCE: 68

Ser His Leu Val Lys Cys Ala Glu Lys Glu Lys Thr Phe Cys Val Asn
1               5                  10                  15

Gly Gly Glu Cys Phe Met Val Lys Asp Leu Ser Asn Pro Ser Arg Tyr
                20                  25                  30

Leu Cys Lys Cys Gln Pro Gly Phe Thr Gly Ala Arg Cys Thr Glu Asn
            35                  40                  45

Val Pro Met Lys Val Gln Thr Gln Glu Lys Cys Pro Asn Glu Phe Thr
        50                  55                  60

Gly Asp Arg Cys Gln Asn Tyr Val Met Ala Ser Phe Tyr Ser Thr Ser
65                  70                  75                  80

Thr Pro Phe Leu Ser Leu Pro Glu
                85

<210> SEQ ID NO 69
<211> LENGTH: 252
<212> TYPE: DNA
<213> ORGANISM: Homo sapiens
<220> FEATURE:
<221> NAME/KEY: CDS
<222> LOCATION: (1)...(249)

<400> SEQUENCE: 69
```

-continued

```
agc cat ctt gtc aag tgt gca gag aag gag aaa act ttc tgt gtg aat      48
Ser His Leu Val Lys Cys Ala Glu Lys Glu Lys Thr Phe Cys Val Asn
 1               5                  10                  15 gga ggc gag tgc ttc atg gtg aaa gac ctt tca aat ccc tca aga tac      96
Gly Gly Glu Cys Phe Met Val Lys Asp Leu Ser Asn Pro Ser Arg Tyr
             20                  25                  30 ttg tgc aag tgc caa cct gga ttc act gga gcg aga tgt act gag aat     144
Leu Cys Lys Cys Gln Pro Gly Phe Thr Gly Ala Arg Cys Thr Glu Asn
         35                  40                  45 gtg ccc atg aaa gtc caa acc caa gaa aag tgc cca aat gag ttt act     192
Val Pro Met Lys Val Gln Thr Gln Glu Lys Cys Pro Asn Glu Phe Thr
     50                  55                  60 ggt gat cgc tgc caa aac tac gta atg gcc agc ttc tac aaa gcg gag     240
Gly Asp Arg Cys Gln Asn Tyr Val Met Ala Ser Phe Tyr Lys Ala Glu
 65                  70                  75                  80 gag ctc tac taa                                                     252
Glu Leu Tyr
```

<210> SEQ ID NO 70
<211> LENGTH: 83
<212> TYPE: PRT
<213> ORGANISM: Homo sapiens

<400> SEQUENCE: 70

```
Ser His Leu Val Lys Cys Ala Glu Lys Glu Lys Thr Phe Cys Val Asn
 1               5                  10                  15

Gly Gly Glu Cys Phe Met Val Lys Asp Leu Ser Asn Pro Ser Arg Tyr
             20                  25                  30

Leu Cys Lys Cys Gln Pro Gly Phe Thr Gly Ala Arg Cys Thr Glu Asn
         35                  40                  45

Val Pro Met Lys Val Gln Thr Gln Glu Lys Cys Pro Asn Glu Phe Thr
     50                  55                  60

Gly Asp Arg Cys Gln Asn Tyr Val Met Ala Ser Phe Tyr Lys Ala Glu
 65                  70                  75                  80

Glu Leu Tyr
```

<210> SEQ ID NO 71
<211> LENGTH: 2003
<212> TYPE: DNA
<213> ORGANISM: Homo sapiens
<220> FEATURE:
<221> NAME/KEY: CDS
<222> LOCATION: (265)...(1530)
<221> NAME/KEY: variation
<222> LOCATION: (31)...(32)
<223> OTHER INFORMATION: n can be a or g.

<400> SEQUENCE: 71

```
ggaattcctt tttttttttt tttttttctt nnttttttttt tgcccttata cctcttcgcc      60
tttctgtggt tccatccact tcttcccct cctcctccca taaacaactc tcctacccct     120 gcaccccaa taaataaata aaggaggag ggcaagggg gaggaggagg agtggtgctg      180 cgagggaag gaaaagggag gcagcgcgag aagagccggg cagagtccga accgacagcc     240
agaagcccgc acgcacctcg cacc atg aga tgg cga cgc gcc ccg cgc cgc      291
                              Met Arg Trp Arg Arg Ala Pro Arg Arg
                                1               5 tcc ggg cgt ccc ggc ccc cgg gcc cag cgc ccc ggc tcc gcc gcc cgc     339
Ser Gly Arg Pro Gly Pro Arg Ala Gln Arg Pro Gly Ser Ala Ala Arg
 10              15                  20                  25
```

| | | |
|---|---|---|
| tcg tcg ccg ccg ctg ccg ctg ctg cca cta ctg ctg ctg ctg ggg acc | 387 | |
| Ser Ser Pro Pro Leu Pro Leu Leu Pro Leu Leu Leu Leu Leu Gly Thr | | |
| 30 35 40 | | |
| gcg gcc ctg gcg ccg ggg gcg gcg gcc ggc aac gag gcg gct ccc gcg | 435 | |
| Ala Ala Leu Ala Pro Gly Ala Ala Ala Gly Asn Glu Ala Ala Pro Ala | | |
| 45 50 55 | | |
| ggg gcc tcg gtg tgc tac tcg tcc ccg ccc agc gtg gga tcg gtg cag | 483 | |
| Gly Ala Ser Val Cys Tyr Ser Ser Pro Pro Ser Val Gly Ser Val Gln | | |
| 60 65 70 | | |
| gag cta gct cag cgc gcc gcg gtg gtc atc gag gga aag gtg cac ccg | 531 | |
| Glu Leu Ala Gln Arg Ala Ala Val Val Ile Glu Gly Lys Val His Pro | | |
| 75 80 85 | | |
| cag cgg cgg cag cag ggg gca ctc gac agg aag gcg gcg gcg gcg gcg | 579 | |
| Gln Arg Arg Gln Gln Gly Ala Leu Asp Arg Lys Ala Ala Ala Ala Ala | | |
| 90 95 100 105 | | |
| ggc gag gca ggg gcg tgg ggc ggc gat cgc gag ccg cca gcc gcg ggc | 627 | |
| Gly Glu Ala Gly Ala Trp Gly Gly Asp Arg Glu Pro Pro Ala Ala Gly | | |
| 110 115 120 | | |
| cca cgg gcg ctg ggg ccg ccc gcc gag gag ccg ctg ctc gcc gcc aac | 675 | |
| Pro Arg Ala Leu Gly Pro Pro Ala Glu Glu Pro Leu Leu Ala Ala Asn | | |
| 125 130 135 | | |
| ggg acc gtg ccc tct tgg ccc acc gcc ccg gtg ccc agc gcc ggc gag | 723 | |
| Gly Thr Val Pro Ser Trp Pro Thr Ala Pro Val Pro Ser Ala Gly Glu | | |
| 140 145 150 | | |
| ccc ggg gag gag gcg ccc tat ctg gtg aag gtg cac cag gtg tgg gcg | 771 | |
| Pro Gly Glu Glu Ala Pro Tyr Leu Val Lys Val His Gln Val Trp Ala | | |
| 155 160 165 | | |
| gtg aaa gcc ggg ggc ttg aag aag gac tcg ctg ctc acc gtg cgc ctg | 819 | |
| Val Lys Ala Gly Gly Leu Lys Lys Asp Ser Leu Leu Thr Val Arg Leu | | |
| 170 175 180 185 | | |
| ggg acc tgg ggc cac ccc gcc ttc ccc tcc tgc ggg agg ctc aag gag | 867 | |
| Gly Thr Trp Gly His Pro Ala Phe Pro Ser Cys Gly Arg Leu Lys Glu | | |
| 190 195 200 | | |
| gac agc agg tac atc ttc ttc atg gag ccc gac gcc aac agc acc agc | 915 | |
| Asp Ser Arg Tyr Ile Phe Phe Met Glu Pro Asp Ala Asn Ser Thr Ser | | |
| 205 210 215 | | |
| cgc gcg ccg gcc gcc ttc cga gcc tct ttc ccc cct ctg gag acg ggc | 963 | |
| Arg Ala Pro Ala Ala Phe Arg Ala Ser Phe Pro Pro Leu Glu Thr Gly | | |
| 220 225 230 | | |
| cgg aac ctc aag aag gag gtc agc cgg gtg ctg tgc aag cgg tgc gcc | 1011 | |
| Arg Asn Leu Lys Lys Glu Val Ser Arg Val Leu Cys Lys Arg Cys Ala | | |
| 235 240 245 | | |
| ttg cct ccc caa ttg aaa gag atg aaa agc cag gaa tcg gct gca ggt | 1059 | |
| Leu Pro Pro Gln Leu Lys Glu Met Lys Ser Gln Glu Ser Ala Ala Gly | | |
| 250 255 260 265 | | |
| tcc aaa cta gtc ctt cgg tgt gaa acc agt tct gaa tac tcc tct ctc | 1107 | |
| Ser Lys Leu Val Leu Arg Cys Glu Thr Ser Ser Glu Tyr Ser Ser Leu | | |
| 270 275 280 | | |
| aga ttc aag tgg ttc aag aat ggg aat gaa ttg aat cga aaa aac aaa | 1155 | |
| Arg Phe Lys Trp Phe Lys Asn Gly Asn Glu Leu Asn Arg Lys Asn Lys | | |
| 285 290 295 | | |
| cca caa aat atc aag ata caa aaa aag cca ggg aag tca gaa ctt cgc | 1203 | |
| Pro Gln Asn Ile Lys Ile Gln Lys Lys Pro Gly Lys Ser Glu Leu Arg | | |
| 300 305 310 | | |
| att aac aaa gca tca ctg gct gat tct gga gag tat atg tgc aaa gtg | 1251 | |
| Ile Asn Lys Ala Ser Leu Ala Asp Ser Gly Glu Tyr Met Cys Lys Val | | |
| 315 320 325 | | |
| atc agc aaa tta gga aat gac agt gcc tct gcc aat atc acc atc gtg | 1299 | |
| Ile Ser Lys Leu Gly Asn Asp Ser Ala Ser Ala Asn Ile Thr Ile Val | | |
| 330 335 340 345 | | |

```
gaa tca aac gct aca tct aca tcc acc act ggg aca agc cat ctt gta    1347
Glu Ser Asn Ala Thr Ser Thr Ser Thr Thr Gly Thr Ser His Leu Val
            350                 355                 360 aaa tgt gcg gag aag gag aaa act ttc tgt gtg aat gga ggg gag tgc    1395
Lys Cys Ala Glu Lys Glu Lys Thr Phe Cys Val Asn Gly Gly Glu Cys
365                 370                 375 ttc atg gtg aaa gac ctt tca aac ccc tcg aga tac ttg tgc aag tgc    1443
Phe Met Val Lys Asp Leu Ser Asn Pro Ser Arg Tyr Leu Cys Lys Cys
        380                 385                 390 cca aat gag ttt act ggt gat cgc tgc caa aac tac gta atg gcc agc    1491
Pro Asn Glu Phe Thr Gly Asp Arg Cys Gln Asn Tyr Val Met Ala Ser
    395                 400                 405 ttc tac agt acg tcc act ccc ttt ctg tct ctg cct gaa taggagcatg     1540
Phe Tyr Ser Thr Ser Thr Pro Phe Leu Ser Leu Pro Glu
410                 415                 420 ctcagttggt gctgctttct tgttgctgca tctcccctca gattccacct agagctagat  1600
gtgtcttacc agatctaata ttgactgcct ctgcctgtcg catgagaaca ttaacaaaag  1660
caattgtatt acttcctctg ttcgcgacta gttggctctg agatactaat aggtgtgtga  1720
ggctccggat gtttctggaa ttgatattga atgatgtgat acaaattgat agtcaatatc  1780
aagcagtgaa atatgataat aaaggcattt caaagtctca cttttattga taaaataaaa  1840
atcattctac tgaacagtcc atcttcttta tacaatgacc acatcctgaa aagggtgttg  1900
ctaagctgta accgatatgc acttgaaatg atggtaagtt aatttttgatt cagaatgtgt 1960 tatttgtcac aaataaacat aataaaagga aaaaaaaaa aaa                    2003
```

<210> SEQ ID NO 72
<211> LENGTH: 422
<212> TYPE: PRT
<213> ORGANISM: Homo sapiens

<400> SEQUENCE: 72

```
Met Arg Trp Arg Arg Ala Pro Arg Arg Ser Gly Arg Pro Gly Pro Arg
1               5                   10                  15

Ala Gln Arg Pro Gly Ser Ala Ala Arg Ser Ser Pro Pro Leu Pro Leu
            20                  25                  30

Leu Pro Leu Leu Leu Leu Leu Gly Thr Ala Ala Leu Ala Pro Gly Ala
        35                  40                  45

Ala Ala Gly Asn Glu Ala Ala Pro Ala Gly Ala Ser Val Cys Tyr Ser
    50                  55                  60

Ser Pro Pro Ser Val Gly Ser Val Gln Glu Leu Ala Gln Arg Ala Ala
65                  70                  75                  80

Val Val Ile Glu Gly Lys Val His Pro Gln Arg Arg Gln Gln Gly Ala
                85                  90                  95

Leu Asp Arg Lys Ala Ala Ala Ala Gly Glu Ala Gly Ala Trp Gly
            100                 105                 110

Gly Asp Arg Glu Pro Pro Ala Ala Gly Pro Arg Ala Leu Gly Pro Pro
        115                 120                 125

Ala Glu Glu Pro Leu Leu Ala Ala Asn Gly Thr Val Pro Ser Trp Pro
    130                 135                 140

Thr Ala Pro Val Pro Ser Ala Gly Glu Pro Gly Glu Glu Ala Pro Tyr
145                 150                 155                 160

Leu Val Lys Val His Gln Val Trp Ala Val Lys Ala Gly Gly Leu Lys
                165                 170                 175

Lys Asp Ser Leu Leu Thr Val Arg Leu Gly Thr Trp Gly His Pro Ala
```

```
                180                 185                 190
Phe Pro Ser Cys Gly Arg Leu Lys Glu Asp Ser Arg Tyr Ile Phe Phe
            195                 200                 205

Met Glu Pro Asp Ala Asn Ser Thr Ser Arg Ala Pro Ala Ala Phe Arg
    210                 215                 220

Ala Ser Phe Pro Pro Leu Glu Thr Gly Arg Asn Leu Lys Lys Glu Val
225                 230                 235                 240

Ser Arg Val Leu Cys Lys Arg Cys Ala Leu Pro Pro Gln Leu Lys Glu
                245                 250                 255

Met Lys Ser Gln Glu Ser Ala Ala Gly Ser Lys Leu Val Leu Arg Cys
            260                 265                 270

Glu Thr Ser Ser Glu Tyr Ser Ser Leu Arg Phe Lys Trp Phe Lys Asn
    275                 280                 285

Gly Asn Glu Leu Asn Arg Lys Asn Lys Pro Gln Asn Ile Lys Ile Gln
    290                 295                 300

Lys Lys Pro Gly Lys Ser Glu Leu Arg Ile Asn Lys Ala Ser Leu Ala
305                 310                 315                 320

Asp Ser Gly Glu Tyr Met Cys Lys Val Ile Ser Lys Leu Gly Asn Asp
                325                 330                 335

Ser Ala Ser Ala Asn Ile Thr Ile Val Glu Ser Asn Ala Thr Ser Thr
            340                 345                 350

Ser Thr Thr Gly Thr Ser His Leu Val Lys Cys Ala Glu Lys Glu Lys
        355                 360                 365

Thr Phe Cys Val Asn Gly Gly Glu Cys Phe Met Val Lys Asp Leu Ser
    370                 375                 380

Asn Pro Ser Arg Tyr Leu Cys Lys Cys Pro Asn Glu Phe Thr Gly Asp
385                 390                 395                 400

Arg Cys Gln Asn Tyr Val Met Ala Ser Phe Tyr Ser Thr Ser Thr Pro
                405                 410                 415

Phe Leu Ser Leu Pro Glu
                420

<210> SEQ ID NO 73
<211> LENGTH: 69
<212> TYPE: PRT
<213> ORGANISM: Homo sapiens

<400> SEQUENCE: 73

Met Ser Glu Arg Lys Glu Gly Arg Gly Lys Gly Lys Gly Lys Lys Lys
 1               5                  10                  15

Glu Arg Gly Ser Gly Lys Lys Pro Glu Ser Ala Ala Gly Ser Gln Ser
            20                  25                  30

Pro Arg Glu Ile Ile Thr Gly Met Pro Ala Ser Thr Glu Gly Ala Tyr
        35                  40                  45

Val Ser Ser Glu Ser Pro Ile Arg Ile Ser Val Ser Thr Glu Gly Ala
    50                  55                  60

Asn Thr Ser Ser Ser
65

<210> SEQ ID NO 74
<211> LENGTH: 19
<212> TYPE: PRT
<213> ORGANISM: Homo sapiens

<400> SEQUENCE: 74

Arg Lys Gly Asp Val Pro Gly Pro Arg Val Lys Ser Ser Arg Ser Thr
```

```
                    1               5              10              15
Thr Thr Ala

<210> SEQ ID NO 75
<211> LENGTH: 6
<212> TYPE: DNA
<213> ORGANISM: Homo sapiens & Bos taurus

<400> SEQUENCE: 75 aataaa                                                                      6

<210> SEQ ID NO 76
<211> LENGTH: 417
<212> TYPE: DNA
<213> ORGANISM: Bos taurus

<400> SEQUENCE: 76
tctaaaacta cagagactgt attttcatga tcatcatagt tctgtgaaat atacttaaac          60
cgctttggtc ctgatcttgt aggaagtcag aacttcgcat tagcaaagcg tcactggctg         120
attctggaga atatatgtgc aaagtgatca gcaaactagg aaatgacagt gcctctgcca         180
acatcaccat tgtggagtca acggtaaga gatgcctact gcgtgctatt tctcagtctc          240
taagaggagt gatcaaggta tgtggtcaca cttgaatcac gcaggtgtct gaaatctcat         300
tgtgaacaaa taaaaatcat gaaaggaaaa ctctatgttt gaaatatctt atgggtcctc         360
ctgtaaagct cttcactcca taaggtgaaa tagacctgaa atatatatag attattt            417

<210> SEQ ID NO 77
<211> LENGTH: 137
<212> TYPE: PRT
<213> ORGANISM: Bos taurus
<220> FEATURE:
<221> NAME/KEY: VARIANT
<222> LOCATION: (14)...(135)
<223> OTHER INFORMATION: Xaa in positions 14, 23, 90, 100, 126, and 135
      is unknown.

<400> SEQUENCE: 77

Asn Tyr Arg Asp Cys Ile Phe Met Ile Ile Ile Val Leu Xaa Asn Ile
 1               5                  10                  15

Leu Lys Pro Leu Trp Ser Xaa Ser Cys Arg Lys Ser Glu Leu Arg Ile
            20                  25                  30

Ser Lys Ala Ser Leu Ala Asp Ser Gly Glu Ser Met Cys Lys Val Ile
        35                  40                  45

Ser Lys Leu Gly Asn Asp Ser Ala Ser Ala Asn Ile Arg Ile Val Glu
    50                  55                  60

Ser Asn Gly Lys Arg Cys Leu Leu Arg Ala Ile Ser Gln Ser Leu Arg
65                  70                  75                  80

Gly Val Ile Lys Val Cys Gly His Thr Xaa Ile Thr Gln Val Ser Glu
                85                  90                  95

Ile Ser Cys Xaa Thr Asn Lys Asn His Glu Arg Lys Thr Leu Cys Leu
            100                 105                 110

Lys Tyr Leu Met Gly Pro Pro Val Lys Leu Phe Thr Pro Xaa Gly Glu
        115                 120                 125

Ile Asp Leu Lys Tyr Ile Xaa Ile Ile
    130                 135

<210> SEQ ID NO 78
<211> LENGTH: 8
```

```
<212> TYPE: PRT
<213> ORGANISM: Bos taurus

<400> SEQUENCE: 78

Val His Glu Val Trp Ala Ala Lys
 1               5

<210> SEQ ID NO 79
<211> LENGTH: 13
<212> TYPE: PRT
<213> ORGANISM: Bos taurus
<220> FEATURE:
<223> OTHER INFORMATION: Xaa in 10 is unknown.

<400> SEQUENCE: 79

Tyr Ile Phe Phe Met Glu Pro Glu Ala Xaa Ser Ser Gly
 1               5                  10

<210> SEQ ID NO 80
<211> LENGTH: 13
<212> TYPE: PRT
<213> ORGANISM: Bos taurus
<220> FEATURE:
<223> OTHER INFORMATION: Xaa is unknown.

<400> SEQUENCE: 80

Leu Gly Ala Trp Gly Pro Pro Ala Phe Pro Val Xaa Tyr
 1               5                  10

<210> SEQ ID NO 81
<211> LENGTH: 8
<212> TYPE: PRT
<213> ORGANISM: Bos taurus

<400> SEQUENCE: 81

Trp Phe Val Val Ile Glu Gly Lys
 1               5

<210> SEQ ID NO 82
<211> LENGTH: 15
<212> TYPE: PRT
<213> ORGANISM: Bos taurus

<400> SEQUENCE: 82

Ala Ser Pro Val Ser Val Gly Ser Val Gln Glu Leu Val Gln Arg
 1               5                  10                  15

<210> SEQ ID NO 83
<211> LENGTH: 11
<212> TYPE: PRT
<213> ORGANISM: Bos taurus

<400> SEQUENCE: 83

Val Cys Leu Leu Thr Val Ala Ala Leu Pro Pro
 1               5                  10

<210> SEQ ID NO 84
<211> LENGTH: 9
<212> TYPE: PRT
<213> ORGANISM: Bos taurus

<400> SEQUENCE: 84

Lys Val His Glu Val Trp Ala Ala Lys
 1               5
```

-continued

```
<210> SEQ ID NO 85
<211> LENGTH: 13
<212> TYPE: PRT
<213> ORGANISM: Bos taurus
<220> FEATURE:
<223> OTHER INFORMATION: Xaa is unknown.

<400> SEQUENCE: 85

Lys Ala Ser Leu Ala Asp Ser Gly Glu Tyr Met Xaa Lys
1               5                   10

<210> SEQ ID NO 86
<211> LENGTH: 6
<212> TYPE: PRT
<213> ORGANISM: Bos taurus
<220> FEATURE:
<223> OTHER INFORMATION: Xaa is unknown.

<400> SEQUENCE: 86

Asp Leu Leu Leu Xaa Val
1               5

<210> SEQ ID NO 87
<211> LENGTH: 4
<212> TYPE: PRT
<213> ORGANISM: Bos taurus

<400> SEQUENCE: 87

Leu Val Leu Arg
```

USE OF NEUREGULINS AS MODULATORS OF CELLULAR COMMUNICATION

This Application is a continuation-in-part of Ser. No. 08/036,555, Mar. 24, 1993, Pat. No. 5,530,109, which is a continuation-in-part of Ser. No 07/965, 173, Oct. 23, 1992, now abandoned, Ser. No.07/940,389, Sep. 3, 1992, now abandoned, Ser. No.07/907,138, Jun. 30, 1992, now abandoned, and Ser. No. 07/863,703, Apr. 3, 1992, now abandoned.

FIELD OF THE INVENTION

This invention relates to methods of affecting cellular communication.

BACKGROUND OF THE INVENTION

Vertebrate cells depend on externally produced factors for growth, differentiation and survival. These factors can be in the form of diffusible, molecules that act at a distance from their site of synthesis. Alternatively these factors can be in the form of cell-surface-bound molecules that rely on cell-to-cell contact for their function. In many cases, different cell types may interact in a reciprocal manner in that both cell types produce factors that affect the other cell type. Vertebrates rely on these reciprocal interactions during embryogenesis and during the response to injury and disease.

Interdependence of cells and tissues plays important roles in the vertebrate nervous system. The nervous system is composed of neurons and neuroglial support cells. Peripheral nervous system axons are ensheathed by neuroglial cells (Schwann cells) and target organs which include skin, sensory receptors, muscle and other neurons. Additionally, peripheral axons interact with components of the central nervous system in the spinal cord. These include neurons and neuroglial cells such as astrocytes and oligodendrocytes It is well established that neurons and the tissues and cells with which they interact are dependent on each other for trophic support. This relationship is mediated by factors (proteins) produced by neurons that maintain the viability of target tissues (e.g. motor neuron derived factors that maintain muscle integrity) and neurotrophic factors produced by target (and other) tissues that maintain neuronal viability (e.g. muscle derived factors that maintain motor neuron viability). This interdependence plays an important role in embryonic development, maintenance of viability and response to injury in the nervous system and its targets.

The survival of various neuronal populations has been thought to be dependent only upon neurotrophic factors produced by targets of innervation. Recently it has been realized that neurotrophic factors are also derived from axonally associated cells (periaxonal glia), soma associated (perisomatic) cells (e.g. glia and efferent synapses) and from autocrine sources. These proteins are taken up by neurons where they exert their effect at the cell body. Neurotrophic factors either maintain the viability of the neuron or induce specific effects such as axonal extension, sprouting and other responses to injury and disease. Examples include factors such as nerve growth factor (NGF), brain derived neurotrophic factor (BDNF) and related molecules as well as ciliary neurotrophic factor (CNTF), insulin like growth factor (IGF) and fibroblast growth factors (FGF's) that all have neurotrophic activity and are derived from neuronally associated tissues as diverse as muscle, Schwann cells and spinal cord astrocytes and other neurons (e.g., Nishi, *Science* (1994) 265:1052).

The identification of pharmaceutical products or agents which induce the endogenous production of trophic factors would be beneficial treatment of diseases which involve trophic support.

SUMMARY OF THE INVENTION

In general, the present invention relates to methods of affecting cellular communication in a vertebrate. The communication is affected by the administration of a neuregulin to a vertebrate, where the neuregulin interacts with a first cell type which results in the production of a product or products (i.e., Product(s) A). This product, in turn, affects the function of a second cell type. (See FIGS. 9 and 10)

Neuregulins are a family of protein factors encoded by one gene. A variety of messenger RNA splicing variants (and their resultant proteins) are derived from this gene and many of these products show binding and activation to erbB2 (neu) and closely related receptors erbB3 and erbB4. The invention provides methods for using all of the known products of the neuregulin gene, as well as, other not yet discovered splicing variants of the neuregulin gene.

Methods also are provided by the invention in which the effect in function of the second cell type, as described above, results in the production of a second product (i.e., Product B) which, in turn, can affect the function of the first cell type or a third cell type. (See FIGS. 9 and 10)

Included in the invention as well, are methods for treatment when disorders involve an altered or inadequate level of production of a product involved in cellular communication.

Advantages of the present invention include the development of new therapeutic approaches to injury or disease based on the interdependence or communication of cells and the ability to influence or affect that communication with neuregulins. For example, a neuregulin factor that is produced by the second cell type can induce the first cell type to produce a product or products (Product(s) A) that are trophic for the second cell type. More specifically, cells and tissues that are associated with neurons may be induced to respond to a neuronally produced factor (neuregulin). This response would be in the form of the production of products (Product(s) A) that are trophic for neurons. The endogenous induction of more than one neurotrophic products by the neuregulin would be more effective than the therapeutic use of a single neurotrophic factor. Neurotrophic factors generally have restricted effects on specific neuronal subtypes (e.g. CNTF is trophic for motor neurons and NGF is trophic for sympathetic neurons as well as a subset of sensory neurons). Furthermore, the types of neurotrophic factors produced by a particular tissue are probably dependent on the target neuron type as well as the type and stage of injury. As an example, CNTF, which is trophic for motor neurons, is released by Schwann cells in the early stages of recovery from nerve injury. This is replaced within a few days by Schwann cell and muscle derived BDNF, another motor neuron trophic factor (Curtis, et al., *Nature* (1993) 365:253–255; and Funakoshi, et al, *J. Cell Biol.* (1993) 123:455–465). In addition multiple neurotrophic factors function in vivo and may be synergistic in their effects. For example, it has been shown that multiple factors more efficiently arrest disease induced neuronal degeneration in animals than the use of a single factor (Mitsumoto et al., *Science* (1994) 265:1107).

In the central nervous system, the neuregulin target, the first cell type, could be a neuron that in turn produces Product(s) A. Product A then affects other tissues (the second cell type) that produce neurotrophic products (Product(s) B) that affect the second cell type (the second cell type may be the source of the neuregulin), or perhaps a third cell type.

Thus, the use of the neuregulins, that are trophic for neuronally associated tissues in the manner described above would be therapeutically useful. Treatment would ensure the production of target specific combinations of products that are tailored to a particular disease state.

BRIEF DESCRIPTION OF THE FIGURES

FIG. 11A is a listing of the coding strand DNA sequence (SEQ ID NO: 1) and deduced amino aid sequence (SEQ ID NO: 2) of the cDNA obtained from splicing pattern of GGF2BPP1 shown in FIG. 12. Potential glycosylation sites are underlined (along with polyadenylation signal AATAAA (SEQ ID NO: 75);

FIGS. 11B–11C is a listing of the coding strand DNA sequence (SEQ ID NO: 3) and deduced amino acid sequence (SEQ ID NO: 4) of the cDNA obtained from splicing pattern of GGF2BPP2. Potential glycosylation sites are underlined (along with polyadenylation signal AATAAA(SEQ ID NO: 75);

FIGS. 11D–11E is a listing of the coding strand DNA (SEQ ID NO: 5) sequence and deduced amino acid sequence (SEQ ID NO: 6) of the cDNA obtained from splicing pattern of GGF2BPP3. Potential glycosylation sites are underlined (along with polyadenylation signal AATAAA(SEQ ID NO: 75).

FIGS. 13A–13R is a listing of the DNA sequences and predicted peptide sequences of the coding segments of GGF(SEQ ID NOs: 7–52). Line 1 is a listing of the predicted amino acid sequences of bovine GGF, line 2 is a listing of the nucleotide sequences of bovine GGF, line 3 is a listing of the nucleotide sequences of human GGF (heregulin) (nucleotide base matches are indicated with a vertical line) and line 4 is a listing of the predicted amino acid sequences of human GGF/heregulin where it differs from the predicted bovine sequence. Coding segments E, A' and K represent only the bovine sequences. Coding segment D' represents only the human (heregulin) sequence.

FIGS. 14A–14B is the predicted GGF2 amino acid sequence (SEQ ID NO: 54) and nucleotide sequence (SEQ ID NO: 53) of BPP5. The upper line is the nucleotide sequence and the lower line is the predicted amino acid sequence.

FIGS. 15A–15B is the predicted amino acid sequence (SEQ ID NO: 56) and nucleotide sequence (SEQ ID NO: 55) of GGF2BPP2. The upper line is the nucleotide sequence and the lower line is the predicted amino acid sequence.

FIGS. 16A–16C is the predicted amino acid sequence (SEQ ID NO: 58) and nucleotide sequence (SEQ ID NO: 57) of GGF2BPP4. The upper line is the nucleotide sequence and the lower line is the predicted amino acid sequence.

Figure 17B:
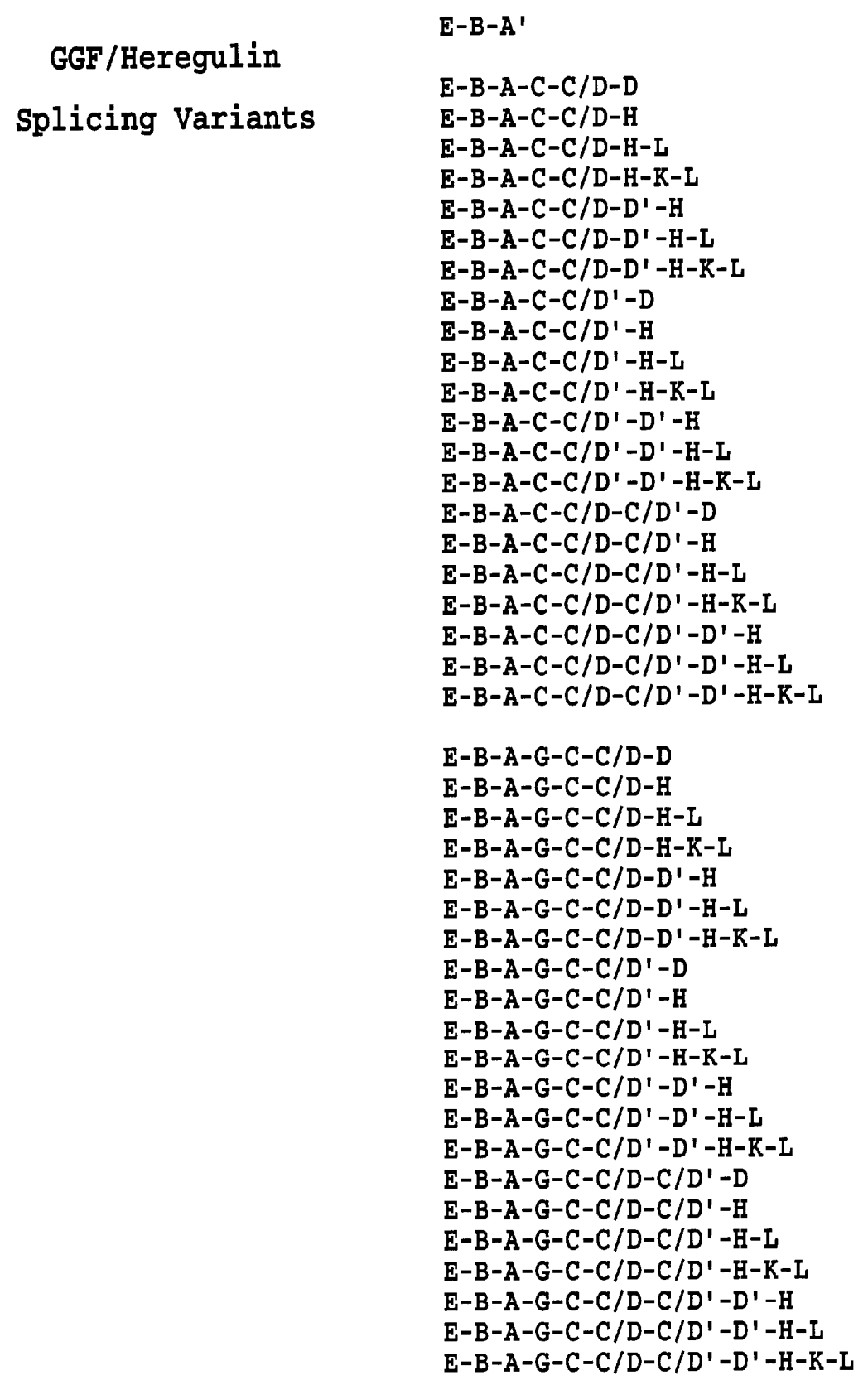

FIG. 17 is a list of splicing variants derived from the sequences shown in FIG. 13.

FIG. 18 is the predicted amino acid sequence (SEQ ID NO: 60), bottom, and nucleotide sequence (SEQ ID NO: 59), top, of EGFL1.

FIG. 19 is the predicted amino acid sequence (SEQ ID NO: 62), bottom, and nucleotide sequence (SEQ ID NO: 61), top, of EGFL2.

FIG. 20 is the predicted amino acid sequence (SEQ ID NO: 64), bottom, and nucleotide sequence (SEQ ID NO: 63), top, of EGFL3.

FIG. 21 is the predicted amino acid sequence (SEQ ID NO: 66), bottom, and nucletide sequence (SEQ ID NO: 65), top, of EGFL4.

FIG. 22 is the predicted amino acid sequence (SEQ ID NO: 68), bottom, and nucleotide sequence (SEQ ID NO: 67), top, of EGFL5.

FIG. 23 is the predicted amino acid sequence (SEQ ID NO: 70), bottom, and nucleotide sequence (SEQ ID NO: 69), top, of EGFL6.

FIG. 24 is the predicted amino acid sequence (SEQ ID NO: 72) (middle) and nucleotide sequence (SEQ ID NO: 71) (top) of GGF2HBS5. The bottom (intermittent) sequence represents peptide sequences derived from GGF-II preparations (SEQ ID NOs: 42, 45–53).

FIG. 25 is the sequences of GGFHBS5 (SEQ ID NO: 72), GGFHB1 (SEQ ID NO: 73) and GGFBPP5 (SEQ ID NO: 74) polypeptides.

FIG. 26 is the amino acid sequence of cDNA encoding mature hGGF2 (SEQ ID NO: 72).

FIG. 27 depicts a stretch of the putative bovine GGF-II gene sequence from the recombinant bovine genomic phage GGF2BG1. The figure is the coding strand of the DNA sequence (SEQ ID NO: 76) and the deduced amino acid sequence in the third reading frame.

DETAILED DESCRIPTION OF THE INVENTION

Figure 1:
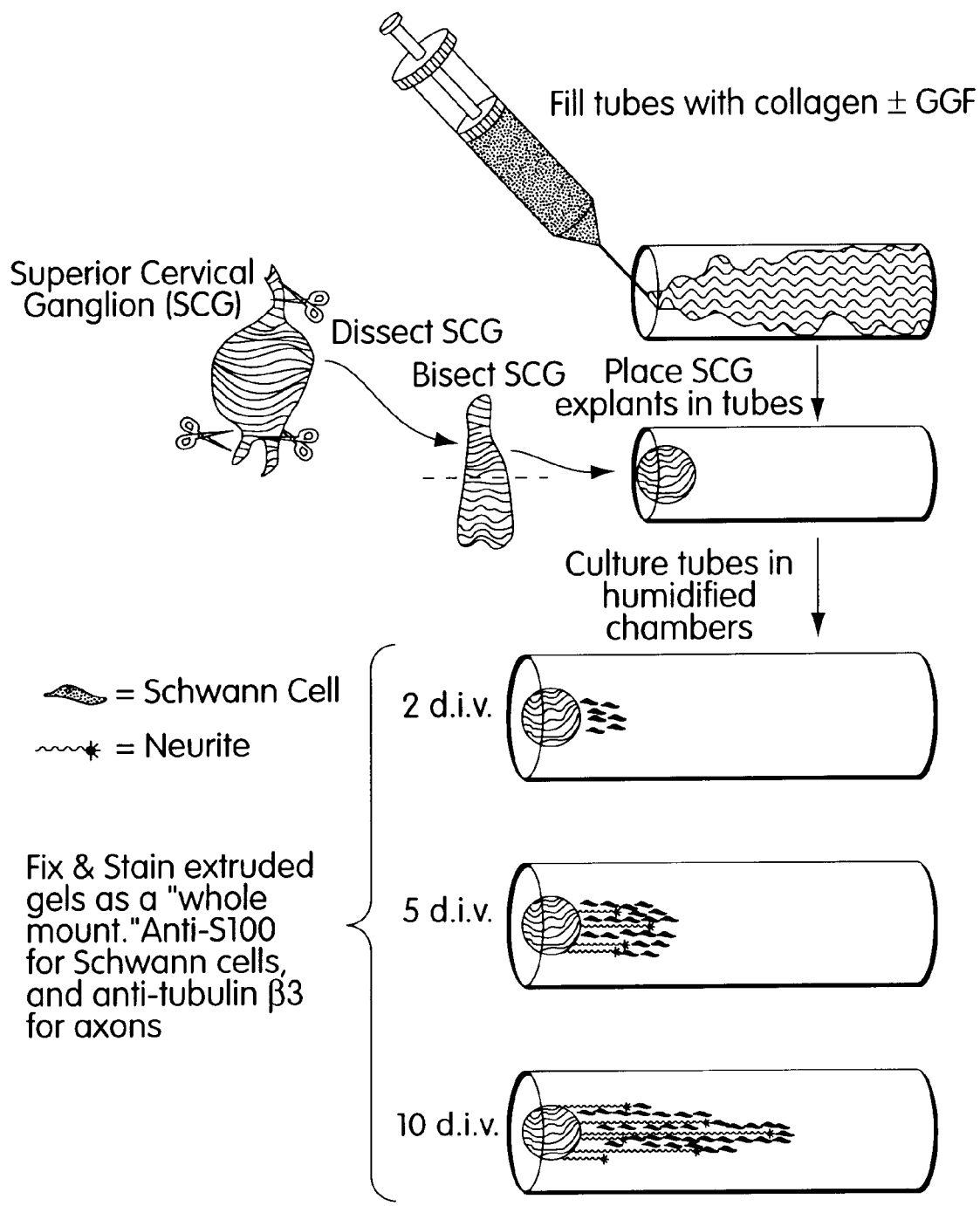
FIG. 1 is a schematic diagram showing the method used to set up the SCG (superior cervical ganglion)/culture tube experiments.

It is intended that all references cited shall be incorporated herein by reference.

General

The invention pertains to methods of affecting cellular communication in vertebrates. The communication is affected by the administration of a neuregulin to a vertebrate where the neuregulin interacts with a first cell type which results in the production of a product. This product, in turn, affects the function of a second cell type. More specifically, the invention relates to the induction of endogenous tropic factors (products) by the administration of a neuregulin.

Methods also are provided by the invention in which the affect in function of the second cell type, described above, results in the production of a second product which, in turn, can affect the function of the first cell type, the second cell type or a third cell type.

Definition of Key Terms

The term affecting as used herein refers to the induction of a quantitative change in the response of a target cell, as a result of an interaction with a Product.

The term interacts as used herein refers to a contact with a target (cell), including but not limited to binding of a product to a cell receptor.

The term cellular communication as used herein refers to the synthesis of a substance in one cell type and the interaction of that substance with a second cell type. This process includes but is not limited to secretion of the substance from a cell. The substance elicits a change in the second cell type or with the first cell type. Communication can occur reciprocally or non-reciprocally with one or more cell types.

The term vertebrate as used herein refers to an animal that is a member of the Subphylum Vertebrata (Phylum Chordata).

The term administration as used herein refers to a pharmaceutical preparation of a substance and the delivery of that preparation to a recipient.

The term neuregulin as used herein refers to the glial growth factors, the heregulins, neu differentiation factor, acetylcholine receptor inducing activity, and erbB2, 3 and 4 binding proteins. A more complete definition of neuregulins can be found in the specification herein and in the following materials: U.S. Pat. No. 5,237,056; U.S. patent application Ser. No. 08/249,322; WO 92/20798; EPO 0 505 148 A1; Marchionni, et al., *Nature* 362:313, 1993; Benveniste, et al., *PNAS* 82:3930–3934, 1985; Kimura, et al., *Nature* (1990) 348:257–260; Davis and Stroobant, *J. Cell. Biol.* (1990) 110:1353–1360; Wen, et al., *Cell* (1992) 69:559; Yarden and Ullrich, *Ann. Rev. Biochem.* (1988) 57:443,; Holmes, et al., *Science* 256:1205, 1992; Dobashi, et al., *Proc. Natl. Acad. Sci.* 88:8582, 1991; Lupu, et al., *Proc. Natl. Acad. Sci.* (1992) 89:2287; Peles and Yarden, *BioEssays* (1993) 15:815, Mudge, *Current Biology* (1993) 3:361, all hereby incorporated by reference.

The term first cell type as used herein refers to the cell type that interacts with a neuregulin. The first cell type includes but is not limited to one or more of the following: neuron, glial cell, Schwann cell, astrocyte, oligodendrocyte, myoblast, muscle cell, satellite cell, skin cell, sensory organ cell, inflammatory cell such as macrophage, neutrophil, T-cell, eosinophil, mast cell, basophil and stromal cell such as fibroblasts or endothelial cells. Bloom and Fawcett, A *Textbook of Histology*, tenth ed. (1975), W. B. Saunders Company, Philadelphia, Pa.

The term second cell type as used herein refers to the cell type that interacts with and responds to Product A. The second cell type includes but is not limited to one or more of the following: neuron, glial cell, Schwann cell, astrocyte, oligodendrocyte, myoblast, muscle cell, satellite cell, skin cell, sensory organ cell, inflammatory cell such as macrophage, neutrophil, T-cell, eosinophil, mast cell, basophil and stromal cell such as fibroblasts or endothelial cells. A more complete definition may be found in Bloom and Fawcett, A *Textbook of Histology*, tenth ed. (1975), W. B. Saunders Company, Philadelphia, Pa.

The term third cell type as used herein refers to a cell type that interacts with and responds to Product B. The third cell type may be identical to the first cell type. The third cell type includes but is not limited to one or more of the following: neuron, glial cell, Schwann cell, astrocyte, oligodendrocyte, myoblast, muscle cell, satellite cell, skin cell, sensory organ cell, inflammatory cell such as macrophage, neutrophil, T-cell, eosinophil, mast cell, basophil and stromal cell such as fibroblasts or endothelial cells. A more complete definition may be found in Bloom and Fawcett, A *Textbook of Histology*, tenth ed. (1975), W. B. Saunders Company, Philadelphia, Pa.

The term production as used herein refers to induced or constitutive synthesis and/or release of a Product from a cell.

The term Product as used herein refers to any substance as defined herein as Product A or Product B.

The term Product A as used herein refers to the substances whose synthesis and release are induced in the first cell type by neuregulin. Such substances include but are not limited to one or more of the following: nerve growth factor (NGF), neurotrophins, brain-derived neurotrophic factor, ciliary neurotrophic factor, leukemia inhibiting factor, interleukin 6, platelet derived growth factor, fibroblast growth factors, transforming growth factor $\beta$, epidermal growth factor, transforming growth factor $\alpha$, neuregulins, insulin like growth factor, matrix molecules, adhesion molecules, growth factor receptors, low affinity NGF receptor, proteases, protease inhibitors, and antioxidants.

The term Product B as used herein refers to the substances whose synthesis and release are induced in the second cell type by Product A. Such substances include but are not limited to one or more of the following: nerve growth factor (NGF), neurotrophins, brain-derived neurotrophic factor, ciliary neurotrophic factor, leukemia inhibiting factor, interleukin 6, platelet derived growth factor, fibroblast growth factors, transforming growth factor $\beta$, epidermal growth factor, transforming growth factor $\alpha$, neuregulins, glial derived neurotrophic factor, insulin like growth factor, matrix molecules, adhesion molecules, growth factor receptors, low affinity NGF receptor (p75), proteases, protease inhibitors and antioxidants.

The term function as used herein refers to any activity or response of a cell. These include but are not limited to proliferation, differentiation, growth, survival, changes in the pattern of gene expression and secretion, and metabolic changes.

The term glial cell as used herein refers to connective and support tissues of the nervous system and includes ectodermally derived astrocytes, oligodendroglia, Schwann cells and mesodermally derived microglia and their progenitors. A more complete definition of glial cells and their progenitors can be found in the following materials: Anderson, *FASEB J.* (1994) 8:707–713; Reynolds and Weiss, *Science* (1992) 255:1707–1710; Reynolds, Tetzlaff, and Weiss, *J. Neurosci* (1992) 12:4565–4574; and Kandel, et al., *Principles of Neuroscience*, third ed. (1991), Appleton & Lange, Norwalk, Conn.

The term astrocyte as used herein refers to a neuroglial cell of ectodermal origin and its progenitor cells. This cell has a round nucleus and a "star shaped" body and many long processes that end as vascular foot plates on the small blood vessels of the CNS and is associated with other structures. A more complete definition of astrocyte and its progenitors can be found in the following materials: Reynolds and Weiss, *Science* (1992) 255:1707–1710; Reynolds, Tetzlaff, and Weiss, *J. Neurosci* (1992) 12:4565–4574; and Kandel, et al., *Principles of Neuroscience*, third ed. (1991), Appleton & Lange, Norwalk, Conn.

The term skin cell as used herein refers to the cellular components of the skin and includes fibroblasts, keratinocytes, epidermal cells, hair follicle cells, melanocytes, myoepithelial sweat gland cells, and sebaceous gland cells and their progenitors. A more complete definition of skin cells and their progenitors can be found in, Wheater, et al., *Functional Histology* (1987), Churchill Livingstone, New York, N.Y.

The term Schwann cell as used herein refers to the neuroglial cell composing the neurolemma of peripheral nerve fibers and its progenitors. A more complete definition of Schwann cells and their progenitors can be found in the following materials: Anderson, *FASEB J.* (1994) 8:707–713; Kandel, et al., *Principles of Neuroscience*, third ed. (1991), Appleton & Lange, Norwalk, Conn.

The term oligodendrocyte as used herein refers to the neuroglial cells, of ectodermal origin, with small oval nuclei and fine cytoplasmic processes that are responsible for the formation of myelin in the CNS. The progenitors of oligodendrocytes are also included. A more complete definition of oligodendrocytes and their progenitors can be found in, Kandel, et al., *Principles of Neuroscience*, third ed. (1991), Appleton & Lange, Norwalk, Conn.

The term sensory organ cell as used herein refers to a primary sensory cell contained within a sensory organ and its progenitors and includes but is not limited to one or more of the following: taste cells, olfactory epithelial cell, rod and cone photoreceptors, Meisner corpuscle, Ruffini corpuscle, Merckel receptor, Pacinian corpuscle, muscle spindle cell, cochleovestibular hair cells and joint mechanoreceptor cells. A more complete definition of sensory organ cells and their progenitors can be found in, Wheater, et al., *Functional Histology* (1987), Churchill Livingstone, New York, N.Y.; Mahanthappa and Schwarting, *Neuron* (1993) 10:293–305; Forge, Li, Corwin and Nevill, *Science* (1993) 259:1616–1622; Tsue, Watling, Weisleder, Coltrera and Rubel, *J. Neurosci* (1994) 14:140–152.

The term neurotrophic agent as used herein refers to a substance that elicits a trophic effect in one or more neuronal subtypes. These effects include but are not limited to survival, sprouting and differentiation.

The term neuron as used herein refers to a complete nerve cell, including the cell body and all of its processes, and its progenitors. A more complete definition of neuron and its progenitors can be found in the following materials: Reynolds and Weiss, *Science* (1992) 255:1707–1710; Reynolds, Tetzlaff, and Weiss, *J. Neurosci* (1992) 12:4565–4574; Ray, Peterson, Schinstine, and Gage, *PNAS* (1993) 90:3602–3606; and Kandel, et al., *Principles of Neuroscience*, third ed. (1991), Appleton & Lange, Norwalk, Conn.

The term matrix molecule as used herein refers to a chemical component of the insoluble meshwork of extracellular proteins that mediate adhesive interactions between cells and modulate the functions of cells.

The term muscle cell as used herein refers to a cellular component of skeletal, smooth or cardiac muscle, including but not limited to myofibrils, satellite cells, and myoepithelial cells and their progenitors. A more complete definition of muscle cells can be found in, Wheater, et al., *Functional Histology* (1987), Churchill Livingstone, New York, N.Y.; and *Myology*, ed. by Engel and Franzini-Armstrong, second ed. (1994) McGraw Hill, New York, N.Y.

The term protease as used herein refers to an enzyme that hydrolyses peptide bonds in a protein molecule.

The term protease inhibitor as used herein refers to a molecule that inhibits the activity and/or function of a protease.

The term differentiation as used herein refers to a morphological and/or chemical change that results in the generation of a different cell type or state of specialization. The differentiation of cells as used herein refers to the induction of a cellular developmental program which specifies one or more components of a cell type. The therapeutic usefulness of differentiation can be seen, in increases in quantity of any component of a cell type in diseased tissue by at least 10% or more, more preferably by 50% or more, and most preferably by more than 100% relative to the equivalent tissue in a similarly treated control animal.

The term mitosis as used herein refers to the division of a cell where each daughter nucleus receives identical complements of the numbers of chromosomes characteristic of the somatic cells of the species. Mitosis as used herein refers to any cell division which results in the production of new cells in the patient. More specifically, a useful therapeutic is defined in vitro as an increase in mitotic index relative to untreated cells of 50%), more preferably 100%, and most preferably 300%, when the cells are exposed to labeling agent for a time equivalent to two doubling times. The mitotic index is the fraction of cells in the culture which have labeled nuclei when grown in the presence of a tracer which only incorporates during S phase (i.e., BrdU) and the doubling time is defined as the average time required for the number of cells in the culture to increase by a factor of two. An effect on mitosis in vivo is defined as an increase in satellite cell activation as measured by the appearance of labeled satellite cells in the muscle tissue of a mammal exposed to a tracer which only incorporates during S phase (i.e., BrdU). A useful therapeutic is defined in vivo as a compound which increases satellite cell activation relative to a control mammal by at least 10%, more preferably by at least 50%, and most preferably by more than 200% when the mammal is exposed to labeling agent for a period of greater than 15 minutes and tissues are assayed between 10 hours and 24 hours after administration of the mitogen at the therapeutic dose.

The term survival as used herein refers to any process where a cell avoids death. The term survival as used herein also refers to the prevention of cell loss as evidenced by necrosis or apoptosis or the prevention of other mechanisms of cell loss. Survival as used herein indicates a decrease in the rate of cell death of at least 10%, more preferably by at least 50%, and most preferably by the least 300% relative to an untreated control. The rate of survival may be measured by counting cells stainable with a dye specific for dead cells (such as propidium iodide) in culture when the cells are 8 days post-differentiation (i.e., 8 days after the media is changed from 20% to 0.5% serum).

The term disorder as used herein refers to a disturbance of function and/or structure of a living organism, resulting from an external source, a genetic predisposition, a physical or chemical trauma, or a combination of the above, including but not limited to any mammalian disease.

The term treating as used herein may refer to a procedure (e.g. medical procedure) designed to exert a beneficial effect on a disorder. Treating as used herein means any administration of a substance described herein for the purpose of increasing cellular communication of products. Most preferably, the treating is for the purpose of reducing or diminishing the symptoms or progression of a disease or disorder of cells. Treating as used herein also means the administration of a substance to increase or alter the cells in healthy individuals. The treating may be brought about by the contacting of the cells which are sensitive or responsive to the neuregulins described herein with an effective amount of the neuregulin.

The term mammal as used herein describes a member of the Class Mammalia (Subphylum Vertebrata).

The term neurological disorder as described herein refers to a disorder of the nervous system.

The term administration as used herein refers to the act of delivering a substance, including but not limited to the following routes: parenteral, intravenous, subcutaneous, intramuscular, intraorbital, ophthalmic, intraventricular, intracranial, intracapsular, intraspinal, intracisternal, intraperitoneal, topical, intranasal, aerosol, scarification, orally, buccal, rectal or vaginal.

The term therapeutically effective amount as used herein refers to that amount which will produce a desirable result upon administration and which will vary depending upon a number of issues, including the dosage to be administered, and the route of administration.

The term peripheral neuropathy as used herein refers to functional disturbances and/or pathological changes in the peripheral nervous system.

The term amyotrophic lateral sclerosis (ALS) as used herein refers to a motor neuron disease characterized by a progressive degeneration of the neurons that give rise to the corticospinal tract that results in a deficit in upper and lower motor neurons.

The term spinal muscular atrophy as used herein refers to a progressive disease of upper and lower motor neurons, usually present in childhood.

The term Alzheimer's Disease as used herein refers to a progressive central neurodegeneration involving loss of cortical and other neurons, and associated with neurofibrillary tangles and β-amyloid deposits.

The term Parkinson's Disease as used herein refers to a progressive central neurodegeneration involving dopaminergic neurons.

The term trophic as used herein refers to an effect of a substance on a cell, including but not limited to proliferation, growth, sprouting, differentiation or survival.

The term neuregulin producing cell as used herein refers to a cell that produces a neuregulin. The term refers to all producer cells including cells that produce recombinant neuregulins.

The term nervous system cell as used herein includes nervous system support cells and neurons.

Neuregulins

A novel aspect of the present invention relates to the ability of neuregulins to affect cellular communication between different and similar cell types. Neuregulins are the products of a gene which produce a number of variably-sized, differentially-spliced RNA transcripts that give rise to a series of proteins. These proteins are of different lengths and contain some common peptide sequences and some unique peptide sequences. The conclusion that these factors are encoded by a single gene is supported by the differentially-spliced RNA sequences which are recoverable from bovine posterior pituitary, human spinal chord and human breast cancer cells (MDA-MB-231). Further support for this conclusion derives from the size range of proteins which act as ligands for the $p185^{erbB2}$ receptor (see below).

Further evidence to support the fact that the genes encoding GGF/$p185^{erbB2}$ binding proteins are homologous comes from nucleotide sequence comparison. Holmes et al., (*Science* (1992) 256:1205–1210) demonstrate the purification of a 45-kilodalton human protein (Heregulin-α) which specifically interacts with the receptor protein $p185^{erbB2}$. Peles et al., (*Cell* (1992) 69:559) describe a complementary DNA isolated from rat cells encoding a protein call "neu differentiation factor" (NDF). The translation product of the NDF cDNA has $p185^{erbB}$ binding activity. Several other groups have reported the purification of proteins of various molecular weights with $p185^{erbB2}$ binding activity. These groups include the following: Lupu et al., (1992) *Proc. Natl. Acad. Sci. USA* 89:2287; Yarden and Peles, (1991) *Biochemistry* 30:3543; Lupu et al., (1990) *Science* 249:1552; Dobashi et al., (1991) *Biochem. Biophys. Res. Comm.* 179:1536; and Huang et al., (1992) *J. Biol. Chem.* 257:11508–11512.

We have found that $p185^{erbB2}$ and related receptor binding proteins (i.e., $p185^{erbB3}$ and $p185^{erbB4}$) affect cellular communication. This effect results in the production of a product from a first cell type, where the product, in turn affects the function of a second cell type. The affect in a function of the second cell type and can result in the production of other products which also can affect functions of other cell types. For example, neuregulins can interact with Schwann cells, which as a result of this interaction produce neurotrophic agents. These agents, in turn, interact with neurons to promote their neuronal regeneration. Alternatively, in the central nervous system, a first cell type, being a neuron, could produce a neuregulin, which in turn, affects a second cell type which is a neuron also.

These neuregulins may be identified using the protocols described herein (Examples 1 and 2) and in Holmes et al., *Science* (1992) 256: 1205; Peles et al., *Cell* (1992) 69:205; Wen et al., *Cell* (1992) 69:559; Lupu et al., *Proc. Natl. Acad. Sci. USA* (1992) 89:2287; Yarden and Peles, *Biochemistry* (1991) 30:3543; Lupu et al., *Science* (1990) 249:1552; Dobashi et al., *Biochem. Biophys. Res. Comm.* (1991) 179:1536; Huang et al., *J. Biol. Chem.* (1992) 257:11508–11512; Marchionni et al., *Nature* (1993) 362:313; and in U.S. patent application Ser. No. 07/931,041, filed Aug. 17, 1992, all of which are incorporated herein by reference.

Specifically, the invention provides for use of polypeptides of a specified formula, and DNA sequences encoding those polypeptides. The polypeptides have the formula

WYBAZCX wherein WYBAZCX is composed of the amino acid sequences shown in FIGS. 13A–13D and 13F–13R (SEQ ID NOs: 8, 10, 12, 14, 16, 18, 20, 24, 26, 28, 30, 32, 34, 36, 38, 40, 42, 44, 46, 48, 50, and 52); wherein W comprises the polypeptide segment F, or is absent; wherein Y comprises the polypeptide segment E, or is absent; wherein Z comprises the polypeptide segment G or is absent; and wherein X comprises the polypeptide segments C/D HKL, C/D H, C/D HL, C/D D, C/D' HL, C/D' HKL, C/D' H, C/D' D, C/D C/D' HKL, C/D C/D' H, C/D C/D' HL, C/D C/D' D, C/D D' H, C/D D' HL, C/D D' HKL, C/D' D' H, C/D' D' HL, C/D' D' HKL, C/D C/D' D' H, C/D C/D' D' HL, or C/D C/D' D' HKL; provided that, either a) at least one of F, Y, B, A, Z, C, or X is of bovine origin; or b) Y comprises the polypeptide segment E; or c) X comprises the polypeptide segments C/D HKL, C/D D, C/D' HKL, C/D C/D' HKL, C/D C/D' D, C/D D' H, C/D D' HL, C/D D' HKL, C/D' D' H, C/D' D' HKL, C/D C/D' D' H, C/D C/D' D' HL, C/D C/D' D' HKL, C/D' H, C/D C/D' H, or C/D C/D' HL.

In addition, the invention includes the use of the DNA sequence comprising coding segments 5'FBA'3' as well as the with corresponding polypeptide segments having the amino acid sequences shown in FIGS. 13A, 13C, and 13D (SEQ ID NOs: 7–10 and 13–20);

the DNA sequence comprising the coding segments 5'FBA'3' as well as the corresponding polypeptide segments having the amino acid sequences shown in FIGS. 13A, 13C, and 13E (SEQ ID NOs; 7–10, 13–16, 21, and 22);

the DNA sequence comprising the coding segments 5'FEBA'3' as well as the corresponding polypeptide segments having the amino acid sequences shown in FIGS. 13A–13D and 13R (SEQ ID NOs: 7–20, 51, and 52);

the DNA sequence comprising the coding segments 5'FEBA'3' as well as the corresponding polypeptide segments having the amino acid sequences shown in FIGS. 13A–13C, 13E, and 13R (SEQ ID NOs: 7–16, 21, 22, 51, and 52).

the DNA sequence comprising the polypeptide coding segments of the GGF2HBS5 cDNA clone (ATCC Deposit No. 75298, deposited Sep. 2, 1992), also known as GGF-II (SEQ ID NO: 72).

The invention further includes the use of peptides of the formula FBA, FEBA, FBA' FEBA' and DNA sequences encoding these peptides wherein the polypeptide segments correspond to amino acid sequences shown in FIGS. 13A–13E and 13R (SEQ ID NOs: 7–10 and 13–20), (SEQ ID NOs; 7–10, 13–16, 21, and 22), (SEQ ID NOs: 7–20, 51, and 52), and (SEQ ID NOs: 7–20, 51, and 52). The polypeptide purified GGF-II polypeptide (SEQ ID NO: 72) is also included as part of the invention.

Also included in this invention is the mature GGF peptide and the DNA encoding said peptide, exclusive of the N-terminal signal sequence, which is also useful for treatment of conditions involving abnormalities in cellular communication.

Furthermore, the invention includes a method of cellular communication by the application to a vertebrate of a –30 kD polypeptide factor isolated from the MDA-MB 231 human breast cell line; or –35 kD polypeptide factor isolated from the rat I-EJ transformed fibroblast cell line to the glial cell; or –75 kD polypeptide factor isolated from the SKBR-3 human breast cell line; or –44 kD polypeptide factor isolated from the rat I-EJ transformed fibroblast cell line, or –25 kD polypeptide factor isolated from activated mouse peritoneal macrophages; or –45 kD polypeptide factor isolated from the MDA-MB 231 human breast cell; or –7 to 14 kD polypeptide factor isolated from the ATL-2 human T-cell line to the glial cell; or –25 kD polypeptide factor isolated from the bovine kidney cell; or –42 kD polypeptide factor (ARIA) isolated from brains.

The invention further includes a method for the use of the EGFL1, EGFL2, EGFL3, EGFL4, EGFL5, and EGFL6 polypeptides, FIG. 18 to 23 and (SEQ ID NOs: 60, 62, 64, 66, 68 and 70) respectively, for the methods of affecting cellular communication in vivo and in vitro.

Also included in the invention is the administration of the GGF-II polypeptide whose sequence is shown in FIG. 24 (SEQ ID NO: 72) for affecting cellular communication.

An additional aspect of the invention includes the use of the above-referenced peptides for the purpose of stimulating Schwann cells to produce growth factors which may, in turn, be harvested for scientific or therapeutic use.

Thus, the invention further embraces a polypeptide factor capable of affecting cellular communication and including an amino acid sequence encoded by:

(a) a DNA sequence shown in FIG. 11A–11E (SEQ ID NOs: 1,3, and 5);

(b) a DNA sequence shown in FIG. 27 (SEQ ID NO: 76);

(c) the DNA sequence represented by nucleotides 281–557 of the sequences shown in FIG. 11A–11E (SEQ ID NOs: 1,3, and 5); or (d) a DNA sequence hybridizable to any one of the DNA sequences according to (a), (b) or (c).

The invention further includes sequences which have greater than 60%, preferably 80%, sequence identity of homology to the sequences indicated above.

While the present invention is not limited to a particular set of hybridization conditions, the following protocol gives general guidance which may, if desired, be followed:

DNA probes may be labeled to high specific activity (approximately $10^8$ to $10^9$ $^{32}$Pdmp/$\mu$g) by nick-translation or by PCR reactions according to Schowalter and Sommer (*Anal. Biochem.* (1989) 177:90–94) and purified by desalting on G-150 Sephadex columns. Probes may be denatured (10 minutes in boiling water followed by immersion into ice water), then added to hybridization solutions of 80% buffer B (2 g polyvinylpyrolidine, 2 g Ficoll-400, 2 g bovine serum albumin, 50 ml 1 M Tris HCL (pH 7.5), 58 g NaCl, 1 g sodium pyrophosphate, 10 g sodium dodecyl sulfate, 950 ml $H_2O$) containing 10% dextran sulfate at $10^6$ dpm $^{32}$P per ml and incubated overnight (approximately 16 hours) at 60° C. The filters may then be washed at 60° C. first in buffer B for 15 minutes followed by three 20-minute washes in 2×SSC, 0.1% SDS then one for 20 minutes in 1×SSC, 0.1% SDS.

In other respects, the invention provides:

(a) a basic polypeptide factor which has, if obtained from bovine pituitary material, an observed molecular weight, whether in reducing conditions or not, of from about 30 kD to about 36 kD on SDS-polyacrylamide gel electrophoresis using the following molecular weight standards:

| | |
|---|---|
| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phosphorylase B (rabbit muscle) | 97,400; | which factor has glial cell mitogenic activity including stimulating the division of rat Schwann cells in the presence of fetal calf plasma, and when isolated using reversed-phase HPLC retains at least 50% of said activity after 10 weeks incubation in 0.1% trifluoroacetic acid at 4° C.; and (b) a basic polypeptide factor which has, if obtained from bovine pituitary material, an observed molecular weight, under non-reducing conditions, or from about 55 kD to about 63 kD on SDS-polyacrylamide gel electrophoresis using the following molecular weight standards:

| | |
|---|---|
| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phosphorylase B (rabbit muscle) | 97,400; | which factor the human equivalent of which is encoded by DNA clone GGF2HBS5 described herein and is capable of affecting cellular communication.

For convenience of description only, the lower molecular weight and higher molecular weight factors of this invention are referred to hereafter as "GGF-I" and "GGF-II", respectively. The "GGF2" designation is used for all clones isolated with peptide sequence data derived from GGF-II protein (i.e., GGF2HBS5, GGF2BPP3).

It will be appreciated that the molecular weight range limits quoted are not exact, but are subject to slight variations depending upon the source of the particular polypeptide factor. A variation of, say, about 10% would not, for example, be impossible for material from another source.

Another important aspect of the invention is a DNA sequence encoding a polypeptide capable of affecting cellular communication and comprising:

(a) a DNA sequence shown FIG. 11A–11E (SEQ ID NOs: 1,3, and 5);

(b) a DNA sequence shown in FIG. 27 (SEQ ID NO: 76);

(c) the DNA sequence represented by nucleotides 281–557 of the sequence shown in FIG. 11A–11E (SEQ ID NO: 1,3, and 5); or (d) a DNA sequence hybridizable to any one of the DNA sequences according to (a), (b) or (c).

Thus other important aspects of the invention are:

(a) A series of human and bovine polypeptide factors capable of affecting cellular communication. These peptide sequences are shown in FIGS. 13, 14, 15 and 16 (SEQ ID NOs: 8, 10, 12, 14, 16, 18, 20, 22, 24, 26, 28, 30, 32, 34, 36, 38, 40, 42, 44, 46, 48, 50, 52, 54, 56, and 58) respectively.

(b) A series of polypeptide factors capable of affecting cellular communication and purified and characterized according to the procedures outlined by Lupu et al., *Science* (1990) 249:1552; Lupu et al., *Proc. Natl. Acad. Sci USA* (1992) 89: 2287; Holmes et al., *Science* (1992) 256:1205; Peles et al., *Cell* (1992) 69:205; Yarden and Peles, *Biochemistry* (1991) 30:3543; Dobashi et al., *Proc. Natl. Acad. Sci.* (1991) 88: 8582; Davis et al., *Biochem. Biophys. Res. Commun.* (1991) 179:1536; Beaumont et al., Patent Application PCT/US91/03443 (1990); Greene et al., Patent Application PCT/US91/02331 (1990); Usdin and Fischbach, *J. Cell. Biol.* (1986) 103:493–507; Falls et al., *Cold Spring Harbor Symp. Quant. Biol.* (1990) 55:397–406; Harris et al., *Proc. Natl. Acad. Sci. USA* (1991) 88:7664–7668; and Falls et al., *Cell* (1993) 72:801–815.

(c) A polypeptide factor (GGFBPP5) is capable of affecting cellular communication. The amino acid sequence is shown in FIG. 14A–14B (SEQ ID NO: 54), and is encoded by the bovine DNA sequence shown in FIG. 14A–14B (SEQ ID NO: 53).

The novel human peptide sequences described above and presented FIGS. 13, 14, 15, and 16 in FIGS. 13A, 13C, 13D, 13F–13M, 13O–13R (SEQ ID NOs: 10, 16, 20, 26, 30, 34, 36, 38, 40, 44, 50, and 52), respectively, represent a series of splicing variants which can be isolated as full length complementary DNAs (cDNAs) from natural sources (cDNA libraries prepared from the appropriate tissues) or can be assembled as DNA constructs with individual exons (e.g., derived as separate exons) by someone skilled in the art.

Other compounds in particular, peptides, which bind specifically to the p185$^{erbB2}$ receptor and related receptors can also be used according to the invention as affections of cellular communication. A candidate compound can be routinely screened for p185$^{erbB2}$ binding, and, if it binds, can then be screened for affecting cellular communication using the methods described herein.

The invention includes any modifications or equivalents of the above polypeptide factors which do not exhibit a significantly reduced activity. For example, modifications in which amino acid content or sequence is altered without substantially adversely affecting activity are included. By way of illustration, in EP-A 109748 mutations of native proteins are disclosed in which the possibility of unwanted disulfide bonding is avoided by replacing any cysteine in the native sequence which is not necessary for biological activity with a neutral amino acid. The statements of effect and use contained herein are therefore to be construed accordingly, with such uses and effects employing modified or equivalent factors being part of the invention.

The new sequences of the invention open up the benefits of recombinant technology. The invention thus also includes the following aspects:

(a) DNA constructs comprising DNA sequences as defined above in operable reading frame position within vectors (positioned relative to control sequences so as to permit expression of the sequences) in chosen host cells after transformation thereof by the constructs (preferably the control sequence includes regulatable promoters, e.g. Trp). It will be appreciated that the selection of a promoter and regulatory sequences (if any) are matters of choice for those of skill in the art:

(b) host cells modified by incorporating constructs as defined in (a) immediately above so that said DNA sequences may be expressed in said host cells—the choice of host is not critical, and chosen cells may be prokaryotic or eukaryotic and may be genetically modified to incorporate said constructs by methods known in the art; and, (c) a process for the preparation of factors as defined above comprising cultivating the modified host cells under conditions permitting expression of the DNA sequences. These conditions can be readily determined, for any particular embodiment, by those of skill in the art of recombinant DNA technology. Glial cell mitogens prepared by this means are included in the present invention.

None of the factors described in the art has the combination of characteristics possessed by the present new polypeptide factors.

The invention also includes a neuregulin as defined above, by extracting vertebrate brain material to obtain protein, subjecting the resulting extract to chromatographic purification by hydroxyapatite HPLC and then subjecting these fractions to SDS-polyacrylamide gel electrophoresis. The fraction which as an observed molecular weight of about 30 kD to 36 kD and/or the fraction which has an observed molecular weight of about 55 kD to 63 kD is collected. In either case, the fraction is subjected to SDS-polyacrylamide gel electrophoresis using the following molecular weight standards:

| | |
|---|---|
| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phosphorylase B (rabbit muscle) | 97,400 |

In the case of the smaller molecular weight fraction, the SDS-polyacrylamide gel is run in non-reducing conditions in reducing conditions or, and in the case of the larger molecular weight fraction the gel is run under non-reducing conditions. The fractions are then tested for activity stimulating the division of rat Schwann cells against a background of fetal calf plasma.

Preferably, the above process starts by isolating a relevant fraction obtained by carboxymethyl cellulose chromatography, e.g. from bovine pituitary material. It is also preferred that hydroxyapatite HPLC, cation exchange chromatography, gel filtration, and/or reversed-phase HPLC be employed prior to the SDS-Polyacrylamide gel electrophoresis. At each stage in the process, activity may be determined using Schwann cell incorporation of radioactive iododeoxyuridine as a measure in an assay generally as described by Brockes in *Meth. Enz.* (1987) 147:217–225, but modified by substituting 10% FCP for 10% FCS. As already noted, such as assay is an aspect of the invention in its own substance for CNS or PNS cell, e.g. Schwann cell, mitogenic effects.

Compounds may be assayed for their usefulness in vitro using the methods provided in the description and examples below. Following the in vitro demonstration of the effect of neuregulins on cellular communication between various cell types, the in vivo therapeutic benefit of the effect can be accomplished by the administration of neuregulins, neuregulin producing cells or DNA encoding neuregulins to a vertebrate requiring therapy. In a specific example, in vivo testing can be demonstrated as described in Example 3.

The invention includes the use of the above named family of proteins (i.e. neuregulins) as extracted from natural sources (tissues or cell lines) or as prepared by recombinant means.

Other compounds in particular, peptides, which bind specifically to the $p185^{erbB2}$ and related receptor binding proteins (i.e., $p185^{erbB3}$ and $p185^{erbB4}$) can also be used according to the invention as affectors of cellular communication. A candidate compound can be routinely screened for $p185^{erbB2}$, $p185^{erbB3}$ and $p185^{erbB4}$ binding, and if it binds, can then be screened for affecting cellular communication using the methods described herein.

The invention includes use of any modifications or equivalents of the above polypeptide factors which do not exhibit a significantly reduced activity related to affecting cellular communication. For example, modifications in which amino acid content or sequence is altered without substantially adversely affecting activity are included. The statements of effect and use contained herein are therefore to be construed accordingly, with such uses and effects employing modified or equivalent factors being part of the invention.

The human peptide sequences described above represent a series of splicing variants which can be isolated as full length complementary DNAs (cDNAS) from natural sources (cDNA libraries prepared from the appropriate tissues) or can be assembled as DNA constructs with individual exons (e.g., derived as separate exons) by someone skilled in the art.

The invention includes methods for the use of any protein which is substantially homologous to the coding segments in FIGS. 13A–13R (SEQ ID NOs: 8, 10, 12, 14, 16, 18, 20, 22, 24, 26, 28, 30, 32, 34, 36, 38, 40, 42, 44, 46, 48, 50, and 52), as well as other naturally occurring GGF polypeptides for the purpose of inducing muscle mitogenesis. Also included are the use of: allelic variations; natural mutants; induced mutants; proteins encoded by DNA that hybridizes under high or low stringency conditions to a nucleic acid naturally occurring (for definitions of high and low stringency see *Current Protocols in Molecular Biology*, (1989) John Wiley & Sons, New York, NY, 6.3.1–6.3.6, hereby incorporated by reference); and the use of polypeptides or proteins specifically bound by antisera to GGF polypeptides. The term also includes the use of chimeric polypeptides that include the GGF polypeptides comprising sequences from FIGS. 13A–13R (SEQ ID NOs: 8, 10, 12, 14, 16, 18, 20, 22, 24, 26, 28, 30, 32, 34, 36, 38,40, 42, 44, 46,48, 50, and 52).

Use of Neuregulins

A novel aspect of the invention involves the use of neuregulins as factors to promote cell communication by inducing the production of products. These Products affect the function of these cells. Treatment of the cells to achieve these effects may be achieved by contacting cells with a polypeptide described herein.

The methods of the invention may also be used to treat a patient suffering from a disease caused by a lack of trophic factor(s). The lack of trophic factor(s) is defined by a decreased amount of trophic factor(s) relative to that of an unaffected individual sufficient to cause detectable alteration in the biological effect of those trophic factor(s). The neurotrophic factor(s) may be present at levels 10% below those observed in unaffected individuals. More preferably, the factor(s) are present at levels 20% lower than that observed in unaffected individuals, and most preferably the levels are lowered by 80% relative to unaffected individuals under similar circumstances.

The methods of the invention make use of the fact that the neuregulin proteins are encoded by the same gene. A variety of messenger RNA splicing variants (and their resultant proteins) are derived from this gene and many of these products show binding to $p185^{erbB2}$ and related receptors and activation of the same. This invention provides a use for all of the known products of the neuregulin gene (described herein and in the references listed above). Most preferably, recombinant human GGF2 (rhGGF2) is used in these methods.

Figure 12:
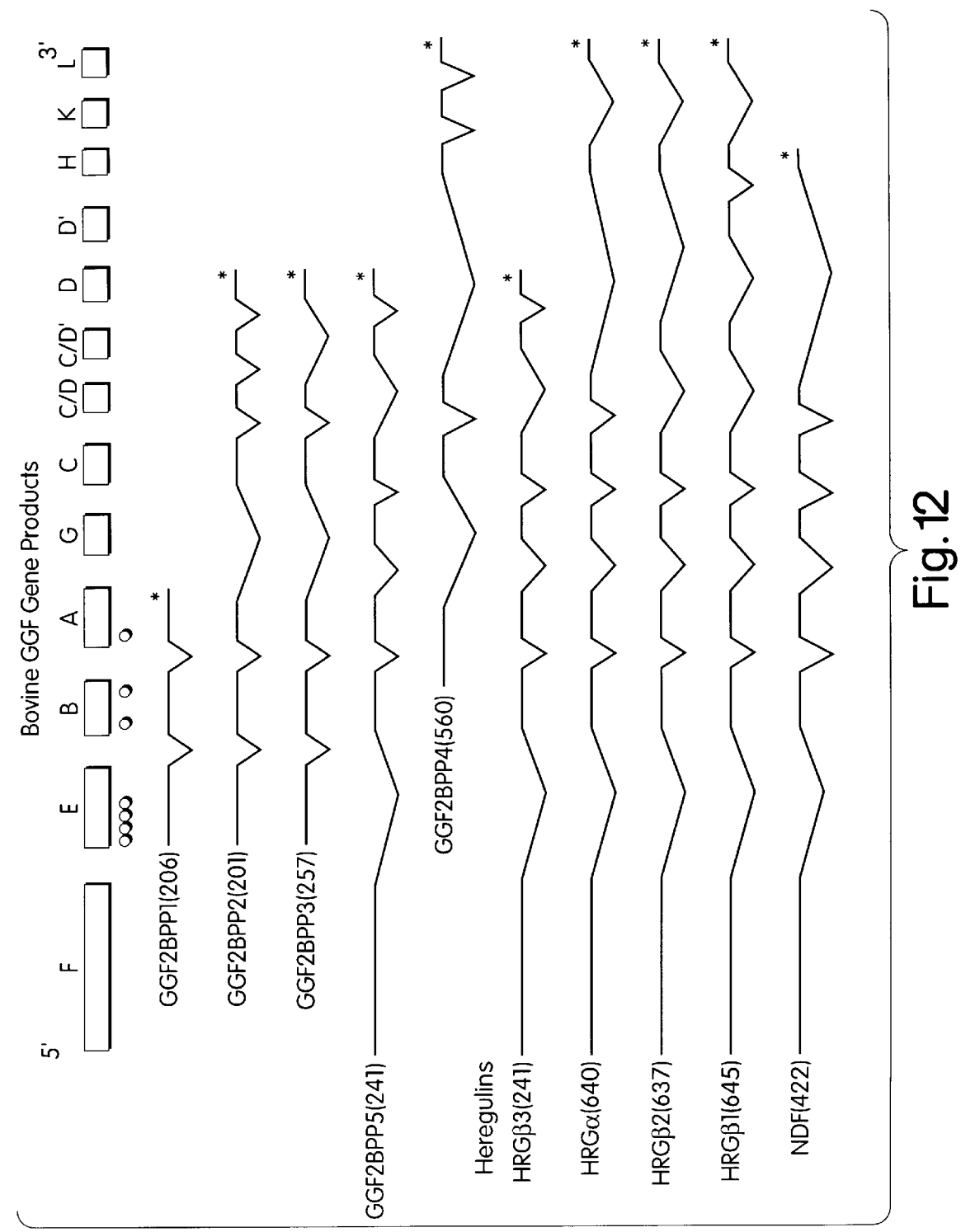
FIG. 12 is a diagram of representative splicing variants. The coding segments are represented by F, E, B, A, G, C, C/D, C/D', D, D', H, K, and L. The location of the peptide sequences derived from purified protein are indicated by "o."

The invention also relates to the use of other, not yet naturally isolated, splicing variants of the neuregulin gene. FIG. 12 shows the known patterns of splicing. These patterns are derived from polymerase chain reaction experiments (on reverse transcribed RNA), analysis of cDNA clones (as presented within), and analysis of published sequences encoding neuregulins (Peles et al., Cell (1992) 69:205 and Wen et al., Cell (1992) 69:559). These patterns, as well as additional patterns disclosed herein, represent probable splicing variants which exist. The splicing variants are fully described in Goodearl et al., U.S. Ser. No. 08/036,555, filed Mar. 24, 1993, incorporated herein by reference.

More specifically, effects on cell communication may be achieved by contacting cells with a polypeptide defined by the formula

WYBAZCX wherein WYBAZCX is composed of the polypeptide segments shown in FIGS. 13A–13D and 13F–13R (SEQ ID NOs: 8, 10, 12, 14, 16, 18, 20, 24, 26, 28, 30, 32, 34, 36, 38, 40, 42, 44, 46, 48, 50, and 52); wherein W comprises the polypeptide segment F, or is absent wherein Y comprises the polypeptide segment E, or is absent; wherein Z comprises the polypeptide segment G or is absent; and wherein X comprises the polypeptide segment C/D HKL, C/D H, C/D HL, C/D D, C/D' HL, C/D' HKL, C/D' H, C/D' D,C/D C/D' HKL, C/DC/D' H,C/D C/D' HL,C/D C/D' D,C/D D' H, C/D D' HL, C/D D' HKL, C/D' D' H, C/D' D' HL, C/D' D' HKL, C/D C/D' D' H, C/D C/D' D' HL, or C/D C/D' D' HKL.

Furthermore, the invention includes a method of treating muscle cells by the application to the muscle cell of a

- –30 kD polypeptide factor isolated from the MDA-MB 231 human breast cell line; or
- –35 kD polypeptide factor isolated from the rat I-EJ transformed fibroblast cell line to the glial cell; or
- –75 kD polypeptide factor isolated from SKBR-3 human breast cell line; or
- –44 kD polypeptide factor isolated from the rat I-EJ transformed fibroblast cell line; or
- –25 kD polypeptide factor isolated from activated mouse peritoneal macrophages; or
- –45 kD polypeptide factor isolated from the MDA-MB 231 human breast cell; or
- –7 to 14 kD polypeptide factor isolated from the ATL-2 human T-cell line to the glial cell; or
- –25 kD polypeptide factor isolated from the bovine kidney cells; or
- –42 kD ARIA polypeptide factor isolated from brain; or
- –46–47 kD polypeptide factor which stimulates 0–2A glial progenitor cells; or
- –43–45 kD polypeptide factor, GGFIII, U.S. patent application Ser. No. 07/931,041, filed Aug. 17, 1992, incorporated herein by reference.

The invention includes use of any modifications or equivalents of the above polypeptide factors which do not exhibit a significantly reduced activity. For example, modifications in which amino acid content or sequence is altered without substantially adversely affecting activity are included. The statements of effect and use contained herein are therefore to be construed accordingly, with such uses and effects employing modified or equivalent factors being part of the invention.

The human peptide sequences described above and presented in FIGS. 13A, 13C, 13D, 13F–13M, 13O–13R (SEQ ID NOs: 10, 16, 20, 26, 30, 34, 36, 38, 40, 44, 50, and 52), respectively, represent a series of splicing variants which can be isolated as full-length complementary DNAs (cDNAs) from natural sources (cDNA libraries prepared from the appropriate tissues) or can be assembled as DNA constructs with individual exons (e.g., derived as separate exons) by someone skilled in the art.

Another aspect of the invention is the use of a pharmaceutical or veterinary formulation comprising any factor as defined above formulated for pharmaceutical or veterinary use, respectively, optionally together with an acceptable diluent, carrier or excipient and/or in unit dosage form. In using the factors of the invention, conventional pharmaceutical or veterinary practice may be employed to provide suitable formulations or compositions.

A medicament is made by administering the polypeptide with a pharmaceutically effective carrier.

Thus, the formulations to be used as a part of the invention can be applied to parenteral administration, for example, intravenous, subcutaneous, intramuscular, intraorbital, ophthalmic, intraventricular, intracranial, intracapsular, intraspinal, intracisternal, intraperitoneal, topical, intranasal, aerosol, scarification, transdermal and by other slow release devices (i.e., osmotic pump-driven devices; see also U.S. Ser. No. 08/293,465, hereby incorporated by reference) and also oral, buccal, rectal or vaginal administration.

The formulations of this invention may also be administered by the transplantation into the patient of host cells expressing the DNA encoding polypeptides which are effective for the methods of the invention or by the use of surgical implants which release the formulations of the invention.

Parenteral formulations may be in the form of liquid solutions or suspensions; for oral administration, formulations may be in the form of tablets or capsules; and for intranasal formulations, in the form of powders, nasal drops, or aerosols.

Methods well-known in the art for making formulations are to be found in, for example, "Remington's Pharmaceutical Sciences." Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The present factors can be used as the sole active agents, or can be used in combination with other active ingredients, e.g., other growth factors which could facilitate neuronal survival in neurological diseases, or peptidase or protease inhibitors.

The concentration of the present factors in the formulations of the invention will vary depending upon a number of issues, including the dosage to be administered, and the route of administration.

In general terms, the factors of this invention may be provided in an aqueous physiological buffer solution containing about 0.1 to 10% w/v compound for parenteral administration. General dose ranges are from about 1 μg/kg to about 1 g/kg of body weight per day; a preferred dose range is from about 0.01 mg/kg to 100 mg/kg of body weight per day. The preferred dosage to be administered is likely to depend upon the type and extent of progression of the pathophysiological condition being addressed, the overall health of the patient, the make up of the formulation, and the route of administration.

A further general aspect of the invention is the use of a factor of the invention in the manufacture of a medicament, preferably for the treatment of a disease or disorder. The "GGF2" designation is used for all clones which were previously isolated with peptide sequence data derived from GGF-II protein (i.e., GF2HBS5, GGF2BPP3) and, when present alone (i.e., GGF2 OR rhGGF2), to indicate recombinant human protein encoded by plasmids isolated with peptide sequence data derived from the GGF-II protein (i.e., as produced in insect cells from the plasmid HBS5). Recombinant human GGF from the GGFHBS5 clone is called GGF2, rhGGF2 and GGF2HBS5 polypeptide.

Methods for treatment of diseases or disorders using neuregulins in this manner are also part of the invention. Administration of neuregulins to induce the production of a substance or substances from a neuregulin responsive cell can be used in any disorder where an increase in a neuregulin inducible substance that is trophic for the disease affected neurons would be of benefit. In peripheral nerve injury or peripheral nerve disorders such as the neuropathies administration of neuregulins will elicit the production of neurotrophic substances from known neuregulin target tissues such as Schwann cells and muscle. These induced substances can enhance axonal repair. Alzheimer's disease is another target for neuregulin therapy. In the brain, neuregulins are detectable in cholinergic motor neurons (Chen, et al., *J. Comparative Neurology* (1994) 349:389–400), these neurons degenerate in Alzheimer's disease and many show trophic responses to neurotrophic factors such as NGF. Neuregulins can be used to induce the synthesis of neurotrophic factors in those neurons that interact with cholinergic neurons. Similar therapeutic approaches may be used in other neurodegenerative disorders such as Parkinson's disease, amyotrophic lateral sclerosis, spinal muscular atrophy or any disease where stimulation of the synthesis of substances that are trophic for disease affected neurons might be of benefit.

Methods for treatment of diseases or disorders using nucleic acid constructs encoding neuregulins or neuregulin producer cells are also part of the invention.

Delivery of DNA to a cell or tissue that will take up the DNA, express the DNA and produce neuregulin as shown by Wolff et al., (*Science* (1990) 247:1465) and Ascadi et al., (*Nature* (1991) 352:815) is an aspect of the invention. The neuregulin produced by this method will act on the first cell type and elicit the responses described above. Genetic modification of cultured cells (or their precursors) such as fibroblasts (as shown by Wolff et al. *Proc. Nat'l Acad. Sci. USA* (1988) 86:1575 ) or such as those derived from the nervous system (as shown by Weiss et al. International Patent Application number PCT/US94/01053; publication number WO 94/16718) to induce the production of neuregulin from the cultured cells is another aspect of this invention. The genetically modified neuregulin producer cells can be transplanted to a position near the first cell type and elicit the responses described above.

Assays for Determining Neuregulin Effect(s) on Cellular Communication

Described below are generic methods for detecting the ability of a neuregulin to induce in a first cell type, the production of a product (Product A) that is trophic for a second cell type. A general reference on cell and tissue culture is *Cell and Tissue Culture: Laboratory Procedures* (Ed. by A. Doyle, J. B. Griffiths, and D. G. Newell, John Wiley and Sons, New York, N.Y., 1994). General references on the culture of neural cells and tissues are *Methods in Neurosciences*, Vol. 2 (Ed. by P. M. Conn. Academic Press, Sand Diego, Calif., 1990) and *Culturing Nerve Cells* (Ed. by G. Banker and K. Goslin, MIT Press, Cambridge, Mass. 1991). General references of immunocytochemistry are *Antibodies: A Laboratory Manual* (E. Harlow and D. Lane, Cold Spring Harbor Laboratory, Cold Spring Harbor, N.Y., 1988), and *Immunocytochemistry II* (Ed. by A. C. Cuello, John Wiley and Sons, New York, N.Y., 1993).

The vertebrate cells used in this invention may be cultured in a variety of media. Commercially available media such as Ham's F10(Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.* (1979) 58:44; Barnes and Sato, *Anal. Biochem.* (1980) 102:255; U.S. Pat. Nos. 4,767, 704; 4,657,866; 4,927,762; or 4,560,655; WO 90/03430; WO 87/00195 and U.S. Pat. Re. 30,985, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression and will be apparent to the ordinarily skilled artisan.

Method I

The use of separate cultures of a first cell type and a second cell type, to demonstrate that neuregulin induces the first cell type to produce a secreted substance that is trophic for the second cell type.

1. Establish cultures of cells from the tissue of interest (e.g. spinal cord, pancreas, gut, etc.). These cultures are enriched for the first cell type such that preferably greater than 90% of the cells can be demonstrated to be the same cell type through the use of immunocytochemical and/or enzymatic markers (e.g. tubulin b3 for neurons (A. Banerjee, M. C. Roach, P. Trcka, and R. F. Luduena Increased microtubule assembly in bovine brain tubulin lacking the type III isotype of b tubulin. *J. Biol. Chem.* (1990) 265:1794–1799), Islet-1 for pancreatic islet cells (O. Karlsson, S. Thor, T. Norbert, H. Ohlsson, and T. Edlund Insulin gene enhanced binding protein Isl-1 is a member of a novel class of proteins containing both a homeo and a Cys-His domain. *Nature* (1990) 344:879–882)).

2. Establish cultures of cells from the same tissue of interest as in step 1. These cultures are enriched for the second cell type such that preferably greater than 90% of the cells can be demonstrated to be the same cell type through the use of immunocytochemical and/or enzymatic markers.

3. Expose the first cell type cultures to varying doses of neuregulin for varying periods of time, preferably greater than 1 minute and less than 7 days. At the end of the culture period, collect the conditioned culture medium, remove debris by centrifugation (200 g, 10 minutes) and filtration (nylon filter, 0.22 mm pore size). This medium (conditioned medium) will contain the secreted product(s) of the first cell type, Product A.

4. Replace or supplement the medium of the second cell type cultures with media prepared as in step 3. Include among these medium samples, medium that has been conditioned by the first cell type cultures in the absence of neuregulin (control conditioned medium). Include among the medium samples, media containing neuregulin that have not been conditioned by the first cell type cultures (non-conditioned medium).

5. Maintain the second cell type cultures as described in step 4 for varying periods of time preferably greater than 1 day and less than 7 days. Assess various aspects of cellular phenotype such as, but not limited to, cell survival, morphology, production of enzymes and secreted products, etc.

6. Assess the effects of the neuregulin. The neuregulin is trophic for the first cell type in a manner that promotes the production of products trophic for the second cell type if:
   a. Medium conditioned by the first cell type cultures in the presence of neuregulin maintains or increases desired aspects of cellular phenotype such as, but not limited to cell survival, morphology, production of enzymes and secreted products, etc.;
   b. equal volumes of control conditioned medium lack the activity described in criterion (a.), or demonstrate lesser degrees of the activity described in criterion (a.); and
   c. equal volumes of non-conditioned medium lack the activity described in criterion (a.), or demonstrate lesser degrees of the activity described in criterion (a.).

The induction by neuregulin of a secreted product, Product A, such that Product A affects a third cell type, can also be tested as in Method I. Establish cultures of cells from the same tissue of interest as in step 1. These cultures are enriched for the third cell type, such that preferably greater than 90% of the cells can be demonstrated to be the same cell type through the use of immunocytochemical and/or enzymatic markers. Substitute the third cell type cultures for the second cell type cultures in steps 4–6.

If Product A is not secreted, but is bound to the surface of the first cell type, or is bound to insoluble extracellular matrix associated with the first cell type, an alternative procedure is to be used:

Method II

The use of separate cultures of the first and second cell types, to demonstrate that neuregulin induces the first cell type to produce a substance on its surface that is trophic for the second cell type.

1. Establish cultures of cells from the tissue of interest (e.g. spinal cord, pancreas, gut, etc.). These cultures are enriched for the first cell type such that preferably greater than 90% of the cells can be demonstrated to be the same cell type through the use of immunocytochemical and/or enzymatic markers (e.g. tubulin b3 for neurons, Islet-1 for pancreatic islet cells).

2. Expose the first cell type cultures to varying doses of neuregulin for varying periods of time, preferably greater than 1 hour and less than 7 days. At the end of the culture period, remove the culture medium and establish a co-culture of the first and second cell types as follows. Rinse the first cell type cultures 3 times with fresh culture medium lacking neuregulin so as to rinse away residual neuregulin. Add back a suspension of the second cell type, from the same tissue of interest as in step 1 in fresh medium lacking neuregulin. The suspension is enriched for the second cell type, such that preferably greater than 90% of the cells can be demonstrated to be the same cell type through the use of immunocytochemical and/or enzymatic markers.

3. In parallel to step 2, plate the same suspension of cells of the second cell type on the first cell type cultures that have not been treated with neuregulin (control co-cultures).

4. Maintain the first cell type/second cell type co-cultures for varying periods of time preferably greater than 1 day and less than 7 days. Assess various aspects of cellular phenotype of the second cell type such as, but not limited to, cell survival, morphology, production of enzymes and secreted products, etc.

5. Assess the effects of neuregulin. Neuregulin is trophic for the first cell type in a manner that promotes the production of products trophic for the second cell type if:
   a. The first cell type cultures pre-treated with neuregulin maintain or increase desired aspects of cellular phenotype of the second cell type such as, but not limited to cell survival, morphology, production of enzymes and secreted products, etc.; and
   b. The first cell type cultures that have not been pre-treated with Product A lack the activity described in criterion (a.), or demonstrate lesser degrees of the activity described in criterion (a.).

The induction by neuregulin of a cell surface-bound or extracellular matrix-bound product, Product A, such that Product A affects a third cell type, can also be tested as in Method II. In steps 2–4, use a suspension of the third cell type rather than the second cell type such that preferably greater than 90% of the cells can be demonstrated to be the third cell type through the use of immunocytochemical and/or enzymatic markers.

Described below are methods for detecting the activities of a neuregulin that induces neuronally-associated tissues to produce a neurotrophic product or product(s) (Product A):

Method III

The use of separate cultures of neurons and neuronally associated tissues, to demonstrate that neuregulin induces a neuronally associated tissue (the first cell type) to produce a secreted product that is trophic for neurons (the second cell type).

1. Establish neuron-free cultures of neuronally-associated cell types (e.g. glia, fibroblasts). These cultures are enriched for a single cell type (the first cell type) such that preferably greater than 90% of the cells can be demonstrated to be the same cell type through the use of immunocytochemical and/or enzymatic markers (e.g. S-100 for peripheral glia (K. R. Jessen and R. Mirsky Schwann cell: early lineage, regulation of proliferation and control of myelin formation. *Curr. Op. Neurobiol.* (1992) 2:575–581), fibronectin for fibroblasts (K. M. Yamada Cell surface interactions with extracellular materials. *Ann. Rev. Biochem.* (1983) 52:761–799)).

2. Establish cultures of neurons from the neuronal tissue of interest (e.g. superior cervical ganglion, spinal motor column). These cultures are enriched for neurons (the second cell type) such that preferably greater than 90% of the cells can be demonstrated to be the same cell type through the use of immunocytochemical and/or enzymatic markers (e.g. tubulin b3 for all neurons, choline acetyltransferase for cholinergic neurons (J.C. Martinou, A. L. V. Thai, G. Cassar, F. Roubinet, and M. J. Weber Characterization of two factors enhancing choline acetyltransferase in cultures of purified rat motoneurons. *J. Neurosci.* (1989) 9:3645–3656)).

3. Expose the first cell type cultures to varying doses of neuregulin for varying periods of time, preferably greater than 1 hour and less than 7 days. At the end of the culture period, collect the conditioned culture medium, remove debris by centrifugation (200 g, 10 minutes) and filtration (nylon filter, 0.22 mm pore size).

4. Replace or supplement the medium of the second cell type cultures with media prepared as in step 3. Include among these medium samples, medium that has been conditioned by the first cell type cultures in the absence of neuregulin (control conditioned medium). Include among the medium samples, media containing neuregulin that have not been conditioned by the first cell type cultures (non-conditioned medium).

5. Maintain the second cell type cultures as described in step 4 for varying periods of time preferably greater than 1 day and less than 7 days. Assess various aspects of neuronal phenotype such as, but not limited to cell survival, neurite (axon or dendrite) outgrowth, neurotransmitter phenotype, etc.

6. Assess the effects of neuregulin. Neuregulin is trophic for neuronally-associated tissues in a manner that promotes the production of neurotrophic products if:
   a. Medium conditioned by the first cell type cultures in the presence of neuregulin maintains or increases desired aspects of neuronal phenotype such as, but not limited to cell survival, increased neurite (axon or dendrite) outgrowth, neurotransmitter synthesis, etc.;
   b. equal volumes of control conditioned medium lack the activity described in criterion (a.), or demonstrate lesser degrees of the activity described in criterion (a.); and
   c. equal volumes of non-conditioned medium lack the activity described in criterion (a.), or demonstrate lesser degrees of the activity described in criterion (a.).

If Product A is not secreted, but is bound to the surface of the first cell type, or is bound to insoluble extracellular matrix associated with the first cell type, an alternative procedure is to be used:

Method IV

The use of separate cultures of neurons and neuronally associated tissues, to demonstrate that neuregulin induces a neuronally associated tissue (the first cell type) to produce a substance on its surface that is trophic for neurons.

1. Establish neuron-free cultures of neuronally-associated cell types (e.g. glia, fibroblasts). These cultures are enriched for a single cell type (the first cell type) such that preferably greater than 90% of the cells can be demonstrated to be the same cell type through the use of immunocytochemical and/or enzymatic markers (e.g. S-100 for peripheral glia, fibronectin for fibroblasts).

2. Expose the first cell type cultures to varying doses of neuregulin for varying periods of time, preferably greater than 1 hour and less than 7 days. At the end of the culture period, remove the culture medium and establish a co-culture of the first cell type and neurons (the second cell type) as follows. Rinse the first cell type cultures 3 times with fresh culture medium lacking neuregulin so as to rinse away residual neuregulin. Add back a suspension of neurons from the neuronal tissue of interest (e.g. superior cervical ganglion, spinal motor column) in fresh medium lacking neuregulin. The suspension is enriched for the second cell type such that preferably greater than 90% of the cells can be demonstrated to be the same cell type through the use of immunocytochemical and/or enzymatic markers (e.g. tubulin b3 for all neurons, choline acetyltransferase for cholinergic neurons).

3. In parallel to step 2, plate the same suspension of the second cell type cells on the first cell type cultures that have not been treated with Product A (control co-cultures).

4. Maintain the first cell type/second cell type co-cultures for varying periods of time preferably greater than I day and less than 7 days. Assess various aspects of neuronal phenotype such as, but not limited to cell survival, neurite (axon or dendrite) outgrowth, neurotransmitter phenotype, etc.

5. Assess the effects of neuregulin. Neuregulin is trophic for the first cell type in a manner that promotes the production of products trophic for the second cell type if:
   a. The first cell type cultures pre-treated with neuregulin maintain or increase desired aspects of neuronal phenotype such as, but not limited to cell survival, neurite (axon or dendrite) outgrowth, neurotransmitter phenotype, etc.; and
   b. The first cell type cultures that have not been pre-treated with Product A lack the activity described in criterion (a.), or demonstrate lesser degrees of the activity described in criterion (a.).

If cultures of non-neuronal cells of interest greater than 90% pure have not been established, the following method can be used:

Method V

The use of a mixed culture, to demonstrate that neuregulins induce the first cell type (neuronally associated cell types) to produce a product (Product A) that affects the second cell type.

1. Establish undissociated, explant cultures of the neuronal tissue of interest (e.g. superior cervical ganglion, spinal motor column). These cultures are not enriched for various cell types and are constituted of both neurons (the second cell type) and neuronally-associated cell types (the first cell type) as demonstrated through the use of immunocytochemical and/or enzymatic markers (e.g. tubulin b3 for all neurons, acetylcholinesterase for cholinergic neurons, S-100 for peripheral glia, fibronectin for fibroblasts).

2. Expose explant cultures to varying doses of neuregulin for varying periods of time, preferably greater than 1 hour and less than 7 days. At the end of the culture period, assess various aspects of neuronal phenotype such as, but not limited to neuron survival, neurite (axon or dendrite) outgrowth, neurotransmitter phenotype, etc.

3. Establish cultures of neurons from the neuronal tissue of interest (e.g. superior cervical ganglion, spinal motor column). These cultures are enriched for neurons (the second cell type) such that preferably greater than 90% of the cells can be demonstrated to be the same cell type through the use of immunocytochemical and/or enzymatic markers (e.g. tubulin b3 for all neurons, choline acetyltransferase for cholinergic neurons).

4. Expose the second cell type cultures to varying doses of neuregulin for varying periods of time, preferably greater than 1 hour and less than 7 days. At the end of the culture period, assess various aspects of neuronal phenotype such as, but not limited to neuron survival, neurite (axon or dendrite) outgrowth, neurotransmitter phenotype, etc.

5. Assess the effects of neuregulin. Neuregulin is trophic for neuronally-associated tissues in a manner that promotes the production of neurotrophic products if:
   a. in explant cultures the presence of neuregulin maintains or increases desired aspects of neuronal phenotype such as, but not limited to neuron survival, neurite (axon or dendrite) outgrowth, neurotransmitter synthesis, etc.; and b. in the second cell type cultures, neuregulin lacks the activity described in criterion (a.), or demonstrates lesser degrees of the activity described in criterion (a.)

EXAMPLES

Example 1

The Effect of Recombinant Human Glial Growth Factor 2 on Sympathetic Ganglion Outgrowth in an In Vitro Model of Peripheral Nerve Gap Entubulation Purpose One approach to the repair of injuries in which a peripheral nerve has been severed is to suture the nerve endings together via a biocompatible tube, a procedure referred to as entubulation. The tube may be filled with various agents thought to improve the growth and regeneration of the nerve. Peripheral nerves contain a variety of cell types: neurons (or more appropriately, the axons emanating from neuron cell bodies located in the spinal cord and associated ganglia), Schwann cells (peripheral glia), fibroblasts, and resident macrophages. Axons regenerate from the side of the nerve gap proximal to the spinal cord and associated ganglia; other cell types contribute to regeneration by migrating in from both sides of the gap and proliferating.

In an effort to devise an in vitro model of entubulation, a technique was developed in which fragments of the rat superior cervical ganglion (SCG) are cultured in segments of surgical tubing used in whole animal models of peripheral nerve entubulation. SCG neurons are homogenous in their trophic requirements and project axons exclusively through peripheral nerves; SCG fragments also contain Schwann cells, fibroblasts, and macrophages. In this model the SCG fragments serve as surrogate proximal nerve endings, and the outgrowth of axons and supporting cell types can be observed in a simplified environment. The focus of this example was to examine the effects of rhGGF2 on Schwann cell and axon behavior in this in vitro model of peripheral nerve entubulation.

Methods and Materials

Tube Preparation

Tubing used for this study was polyethylene tubing with an internal diameter of 1.19 mm and outer diameter of 1.70 mm (Intramedic®; Becton Dickinson and Company; Parsippany, N.J.). A length of tubing somewhat longer than actually needed was cut in a sterile tissue culture hood, immersed in 70% ethanol, and flushed repeatedly with 70% ethanol using a syringe with a 19-gauge needle. After soaking the tubing for approximately 30 minutes, it was flushed again with air, and allowed to dry in the hood. After drying, the tubing was cut into 10 mm segments with a sterile scalpel, and stored in a sterile Petri dish.

Culture Medium

Culture medium was made freshly on the day of culture assembly. All components were kept cold (either 4° C. or on ice), as was the final solution until culture assembly was completed.

| Sterile Water | 2.60 |
| Sodium bicarbonate (2% w/v) | 1.50 |
| Penicillin/Streptomycin stock* | 0.15 |
| L-Glutamine (200 mM) | 0.15 |
| Fetal Bovine Serum** | 0.75 |
| Sodium hydroxide (0.1 M) | 0.90 |
| 10x Medium*** | 1.50 |
| Collagen solution**** | 7.40 |
| TOTAL | 15.00 ml |

*5000 units/ml penicillin, 5 mg/ml streptomycin
**heat inactivated (Hyclone; Logan, UT)
***one packet of low glucose Dulbecco's Modified Essential Medium (DMEM: Gibco/BRL; Grand Island, NY) meant to make 1 liter of medium dissolved in 100 ml of sterile water
****3 mg/ml Vitrogen-100 ® (Celtrix Pharmaceuticals; Santa Clara, CA)

Medium was used as is, or was supplemented with rhGGF2 as indicated.

Tube Culture Assembly

A schematic diagram of culture assembly is shown in FIG. 1. SCGs were dissected from postnatal day 0–2 rats on the day of assembly, cleaned of connective tissues and proximal nerve stumps, bisected, and stored in physiological saline at 4° till needed. Since the collagen-containing medium gels at room temperature or higher, it is necessary to assemble the cultures in 4° cold room. Working with watchman's forceps under a dissection microscope at total magnification of 8x, individual segments of cleaned tubing were picked up and filled with culture medium using a syringe with a 27-gauge needle. A single piece of bisected SCG was then placed at the very end of each tube, and each tube placed in an individual well of a 24-well tissue culture plate. Only the central eight wells of a 24-well plate were used for tube placement, and the remaining wells were filled with sterile water to maintain plate humidity. The plate was then placed in a 37°, 10% carbon dioxide incubator. After allowing the cultures to gel and equilibrate with the incubator atmosphere, the plates were sealed with paraffin film to further protect the culture assemblies from dehydration, and returned to the incubator until preparation for immunocytochemistry and analysis.

Immunocytochemistry

After 2, 5, and 10 days in vitro, the contents of individual tube cultures were extruded into phosphate buffered saline (PBS) using a PBS-filled syringe with a blunt-ended 18-gauge needle. The collagen gels retained structural integrity and were fixed in 4% paraformaldehyde in PBS for 30 minutes at room temperature. After 3 washes with PBS, the cultures were blocked in 1% goat serum/0.1% Triton X-100 in PBS for 30 minutes. After blocking, the solution was changed to 1% goat serum in PBS (GPBS) containing 1:4 rabbit anti-S-100 (a Schwann cell marker; Incstar; Stillwater, Minn.) and 1:400 mouse anti-tubulin b3 (an axon marker; Sigma; St. Louis, Mo.). After incubating the samples in primary antibody for 1 hour at room temperature, they were washed 3 times with PBS, and incubated for an additional hour in GPBS containing 1:200 peroxidase-conjugated goat anti-mouse immunoglobulin, and 1:200 alkaline phosphatase-conjugated goat anti-rabbit immunoglobulin (Pierce Chemical; Rockford, Ill.). The samples were then washed 3 times with PBS, and the stains developed. The S-100 was first developed using stable pre-mixed NBT/BCIP (Gibco/BRL) to yield a blue stain, and after rinsing with PBS, the tubulin b3 was developed using 3-amino-9-ethylcarbazole (AEC; Sigma) per manufacturer's directions. After final rinsing with PBS, the samples were mounted on microscope slides using aqueous mounting medium. After the mounting medium dried, the cellular outgrowth could be analyzed.

Scoring and Analysis

Figure 2:
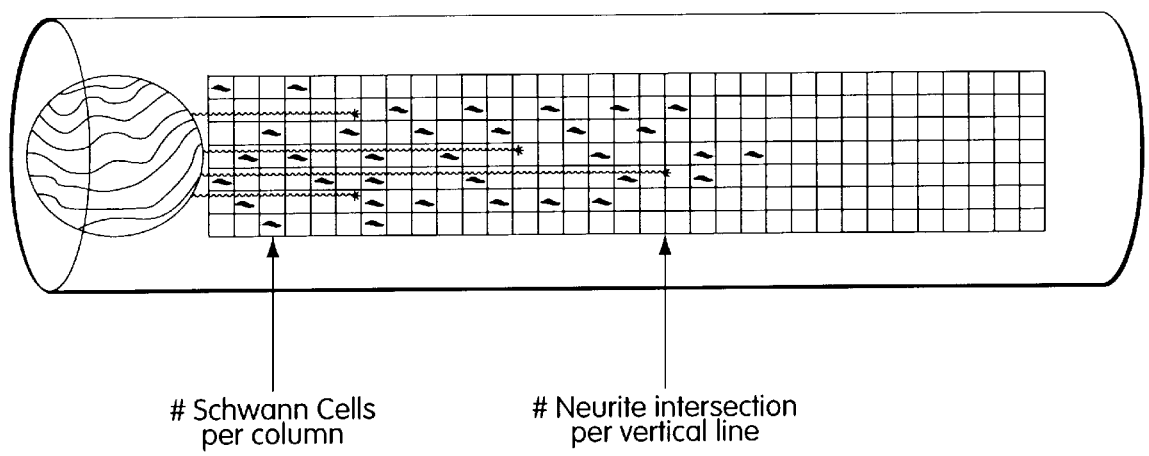
FIG. 2 is a schematic diagram of the grid reticule inserted in the microscope ocular, which at a total magnification of 160×, allowed quantification of Schwann cell outgrowth and neurite outgrowth for the SCG/culture tube experiments.
Figure 3A:
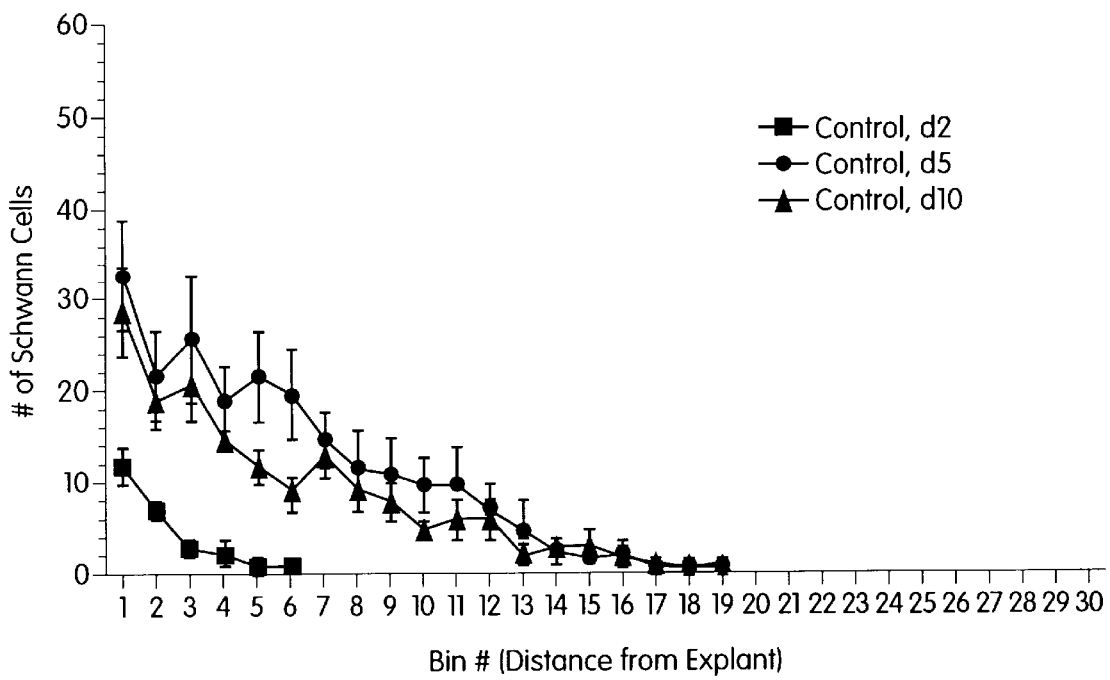
FIG. 3A shows the control data, that is, Schwann cell number as a function of distance from the SCG explant, for the SCG /culture tube experiments.
Figure 3B:
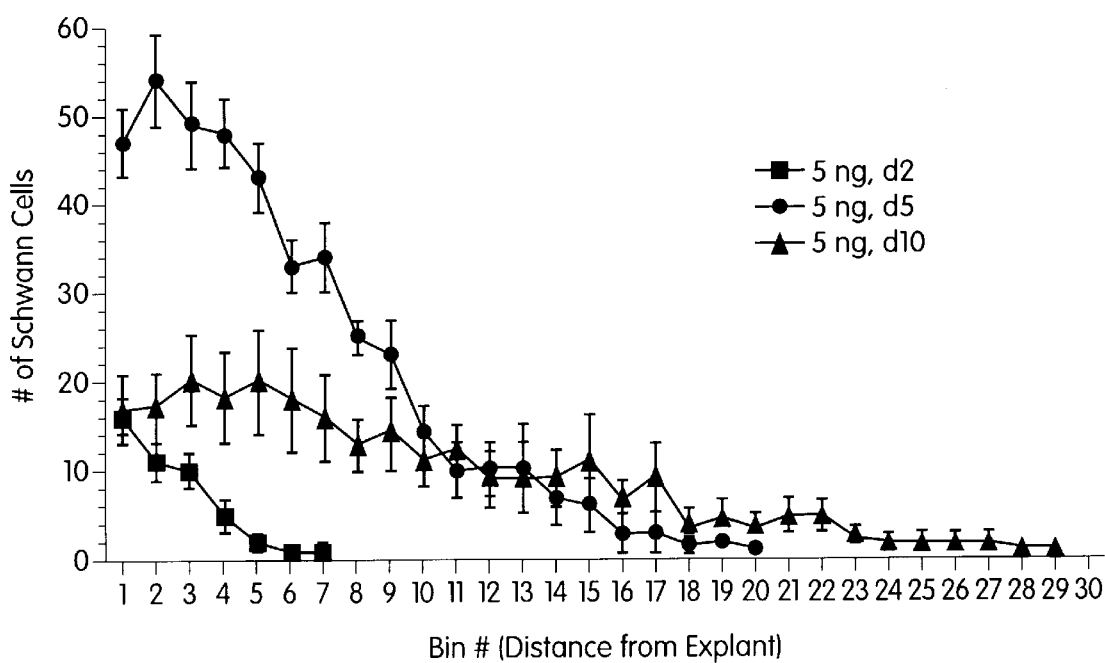
FIG. 3B shows experimental data, of Schwann cell outgrowth for the SCG/culture tube experiments, at a dosage of 5 ng/ml rhGGF2.
Figure 3C:
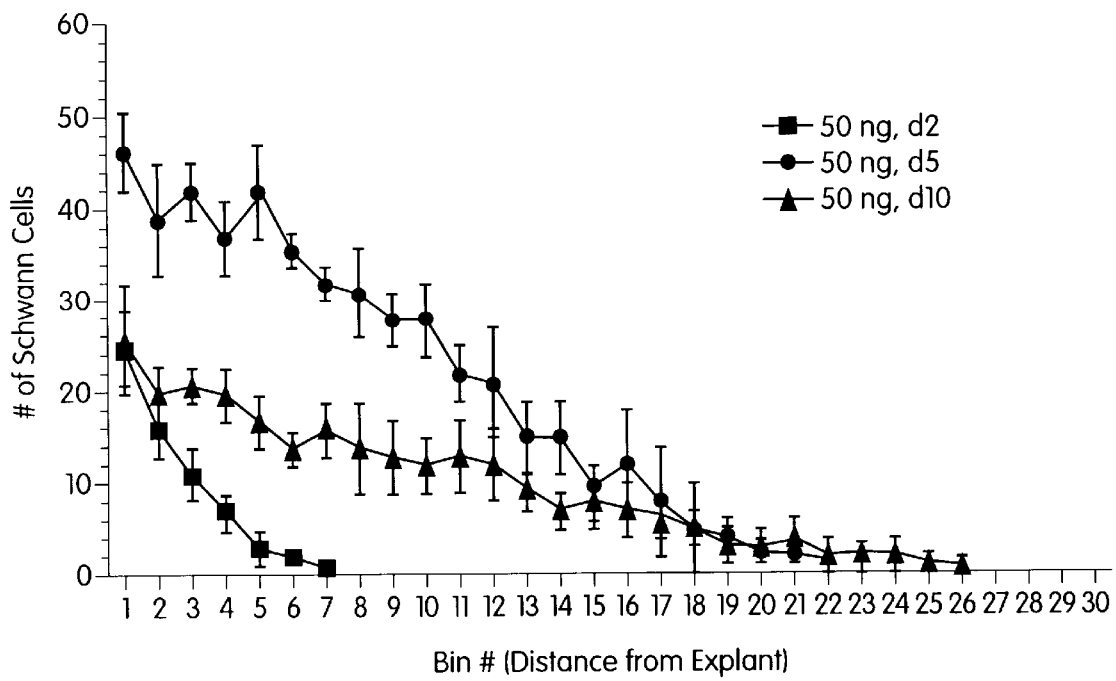
FIG. 3C shows experimental data, of Schwann cell outgrowth for the SCG/culture tube experiments, at a dosage of 50 ng/ml rhGGF2.
Figure 3D:
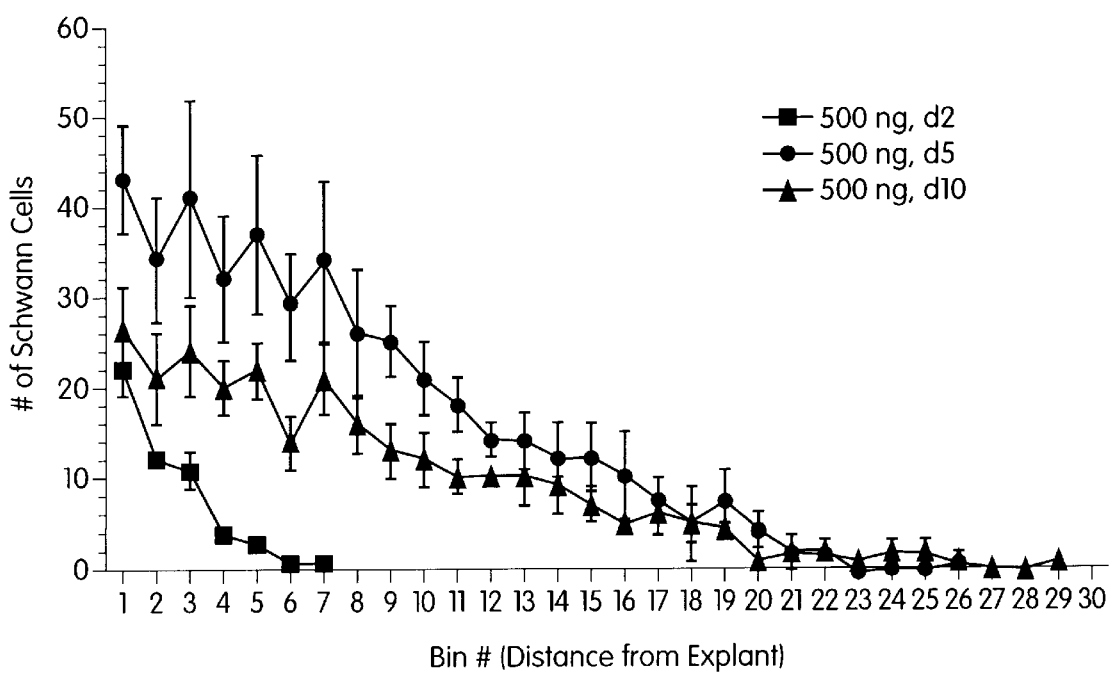
FIG. 3D shows experimental data, of Schwann cell outgrowth for the SCG/culture tube experiments, at a dosage of 500 ng/ml rhGGF2.

As schematized in FIG. 2, a grid reticule was placed in the microscope ocular, and at a total magnification of 160×, the total number of S-100+ Schwann cells in each column (referred to as "bins") was counted. Each bin has width of 50 mm as determined using a stage micrometer. And as noted, the number tubulin-b3+ neurites intersecting every vertical line was also counted. The actual grid was not large enough to cover the entire length of cellular outgrowth and was shifted along as needed by translational movement of the microscope stage. All data points represent the average±the standard error of the mean (n=6 to 7 for every data point).

Results

Figure 4:
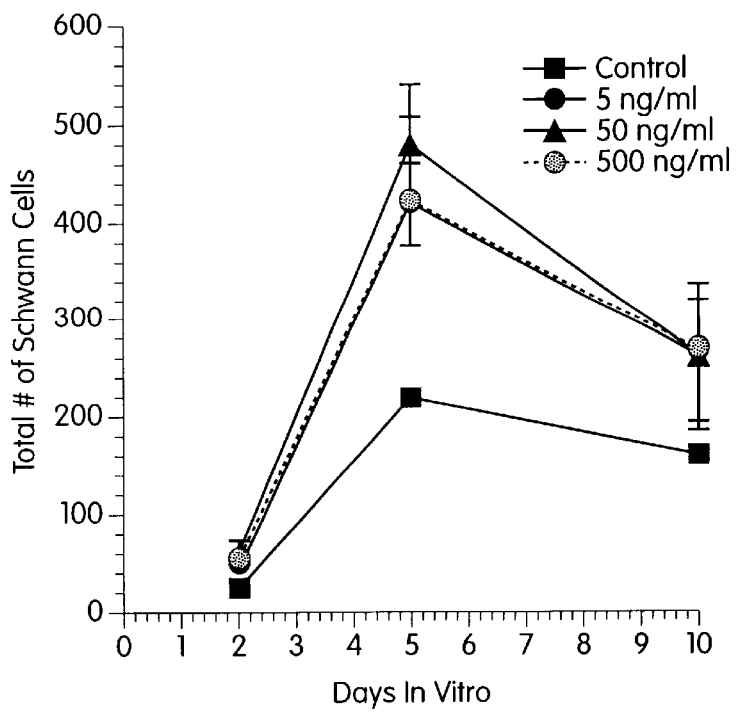
FIG. 4 shows the total number of Schwann cells as a function of days in vitro for the SCG/culture tube experiments.

First shown is the analysis of Schwann cell number as a function of distance from the SCG explant (FIG. 3A–D). It is clear that the presence of rhGGF2 affects the behavior of Schwann cells relative to the control condition. There does not appear to be any difference among the 3 doses of rhGGF2. Generally, by 5 days in rhGGF2, there is a large increase in the number of Schwann cells proximal to the explant, but the Schwann cells appear to have moved only about as far as they have in the control case (somewhat further at the highest dose). By 10 days in rhGGF2 the overall number of Schwann cells has decreased, but the cells still present have definitely migrated farther than in the absence of rhGGF2. In the absence of rhGGF2, the controls look no different between days 5 and 10. The total number of Schwann cells in the various conditions is shown in FIG. 4. Again, there is a decrease in cell number at day 10, but there is no obvious difference between the different doses of rhGGF2. The day 10 tubes contain more debris, and this is probably due to cell death. This is due to the culture situation since 10 days appears to be the longest that one can maintain these tube cultures without overt signs of dehydration and nutrient depletion in the limited volume of culture medium (approximately 10 µl per tube).

Figure 5:
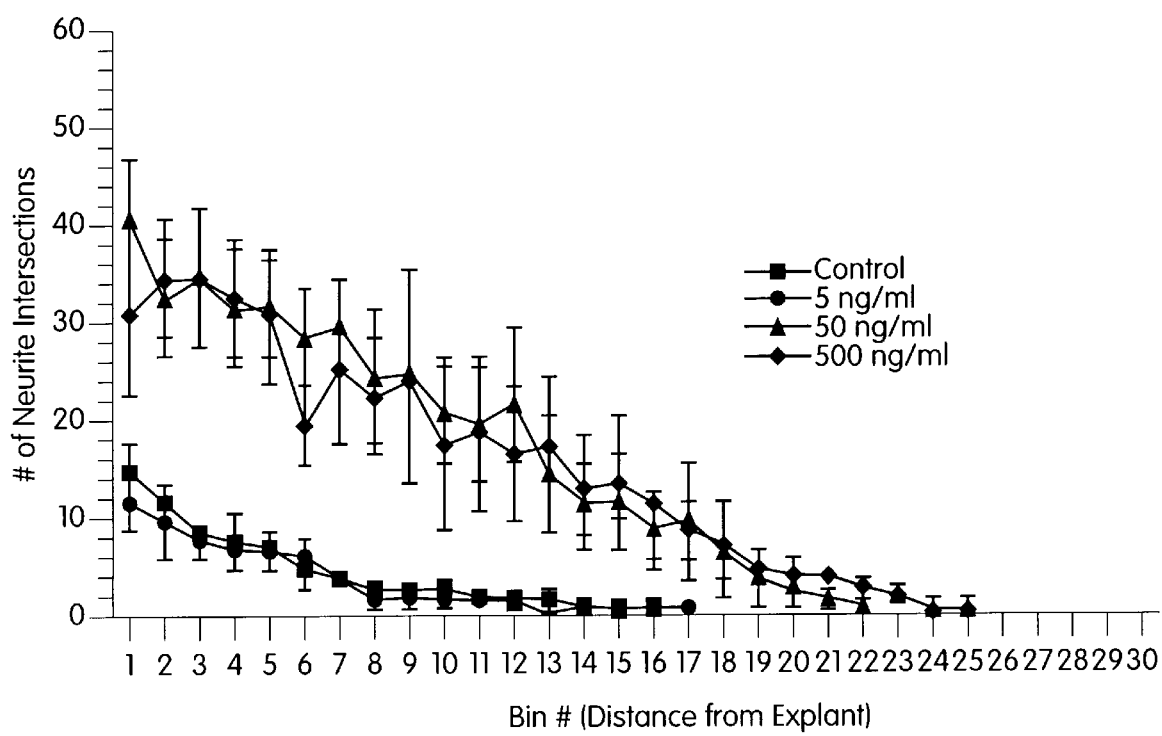
FIG. 5 shows experimental data, of neurite outgrowth, as a function of distance from the SCG explant, for the SCG/ culture tube experiments performed at dosage levels of 5,50 and 500 ng/ml rhGGF2.

A difference is apparent when neurites are scored in the various doses of rhGGF2 (FIG. 5). At doses of rhGGF2 greater than or equal to 50 ng/ml, a profound increase takes place in the number of neurites and the extent to which they have grown away from the explant.

Discussion and Conclusions

This study demonstrates that the dose range in which there are observable effects on Schwann cell proliferation and emigration from the explant is different from that which causes a major increase in neurite outgrowth. In the case of the former, it appears that the effect has plateaued at the lowest dose tested, 5 ng/ml. As for the requirement of ≧50 ng/ml rhGGF2 to boost neurite regeneration, there are two possible mechanisms to account for this. One is that rhGGF2 is acting directly upon the neurons, and the other is that rhGGF2 induces a non-neuronal cell type to produce a neurite promoting factor (e.g. NGF, secreted extracellular matrix proteins, proteases, and/or protease inhibitors). As is demonstrated in Example 2, the first hypothesis is not likely since rhGGF2 has no effect upon neuronal survival or outgrowth in low density cultures of dissociated SCG neurons. This lack of a direct effect on neurons implies that the rhGGF2 promotion of neurite outgrowth is due to rhGGF2 induced production of neurite promoting factors by non-neuronal cells.

Example 2

The Promotion of Axon Outgrowth by Recombinant Human Glial Growth Factor 2 is Not Due to a Direct Effect on Neurons Purpose As demonstrated in Example 1, rhGGF2 not only promotes Schwann cell proliferation and migration in an in vitro model of peripheral nerve entubulation, but also promotes robust axonal outgrowth. To test whether this may be due to direct effects of rhGGF2 on SCG neurons, low density cultures of dissociated SCG neurons were established in which the effects of rhGGF2 could be examined. SCG neurons are normally dependent upon nerve growth factor (NGF) for survival, so rhGGF2 was tested for direct neuronal effects in the simultaneous presence of a wide range of NGF concentrations.

Methods and Materials

Cell Culture

Figure 6A:
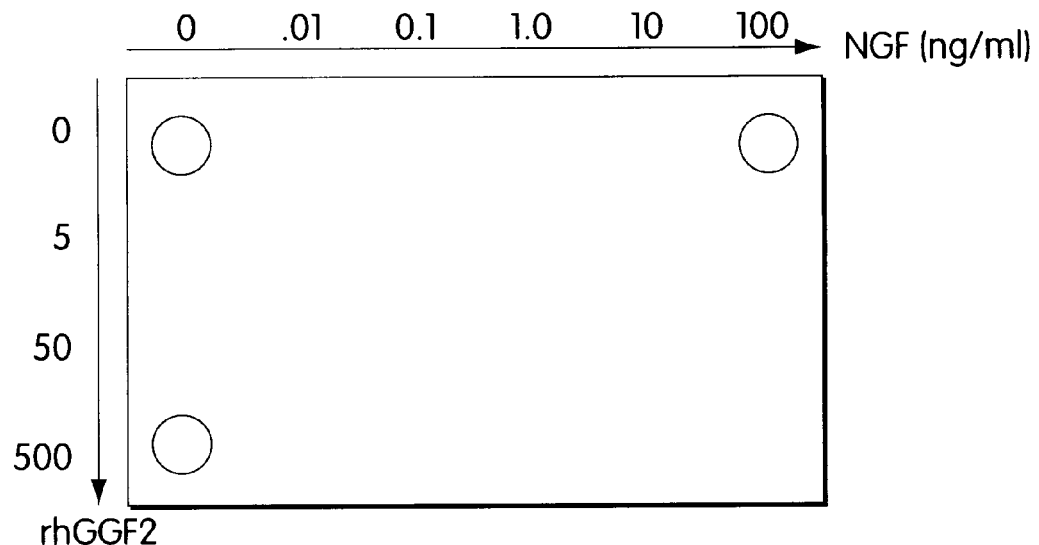
FIG. 6A shows a 2-dimensional dose-response matrix, used to examine the effects of rhGGF2 on neuronal survival and outgrowth.

SCGs were dissected from postnatal day 0–2 rats, cleaned of connective tissue and proximal nerve stumps, and dissociated by enzymatic digestion and trituration. Enzymatic digestion was performed using 1 mg/ml trypsin (Sigma; St. Louis, Mo.) and 1 mg/ml collagenase (Boehringer-Mannheim; Indianapolis, IN) in calcium- and magnesium-free Hanks's Balanced Salt Solution (HBSS; Gibco/BRL; Grand Island, N.Y.), for 1 hour at 37° C. Trituration was performed using a flame-polished Pasteur pipet. Dissociated neurons were taken up in plating medium and pre-plated in tissue culture dishes for 1 hour to remove the majority of the rapidly adherent, non-neuronal cells. Plating medium consisted of low glucose DMEM (Gibco/BRL) supplemented with glutamine, penicillin/streptomycin, and fetal bovine serum to the same concentrations as described in Example 1. Non-adherent cells (primarily neurons), were pelleted by centrifugation and resuspended in plating medium. These cells were finally plated at a density of 5000 cells per well in collagen-coated, 24-well plates such that the cells were exposed to a 2-dimensional dose-response matrix of NGF and rhGGF2 (FIG. 6A). Plates were set up in duplicate on 2 different dates; at the completion of both experiments N=4 for each of the 24 conditions. The cultures were only allowed to progress for 2 days since this is a time frame in which any contaminating Schwann cells could have only undergone a single doubling, and sufficient for ascertaining whether the factors have promoted neuronal survival.

Staining and Scoring of the Cultures

Figure 6B:
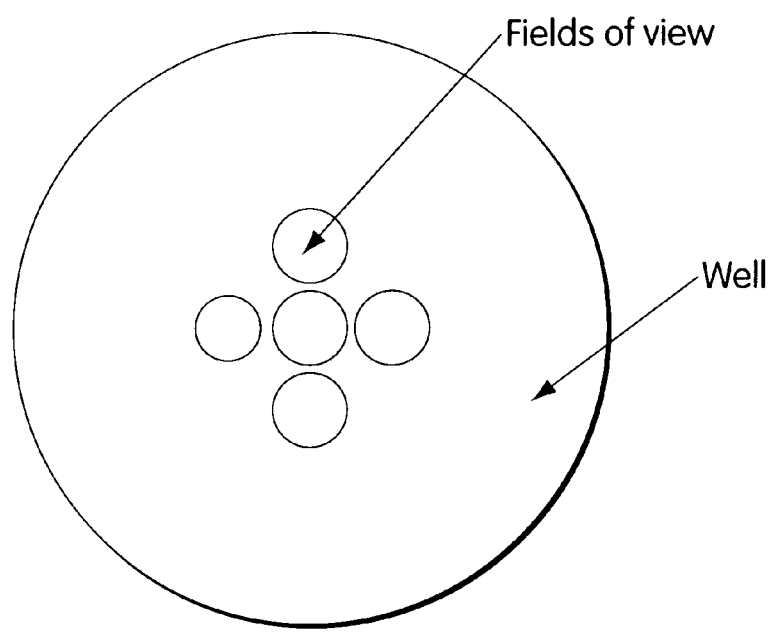
FIG. 6B illustrates the manner of counting, used in the afore-mentioned 2-dimensional dose-response experiment, by showing a representative sample well with fields of view.

After 2 days, the cultures were fixed and stained for tubulin b3 as described in Example 1. The tubulin b3-positive, neurite-bearing cells were counted in each well at a total magnification of 100×. Due to meniscus effects, and incubator vibration during the initial plating period, cells tend to preferentially concentrate in the center of the well. Thus in order to get a reasonably representative count of cell number 5 fields per well were counted: the center most field and four flanking fields (FIG. 6B). This manner of counting was used on all wells and is sufficiently consistent for the purpose of comparing the effects of different growth factor concentrations and combinations. The number of cells counted in every well was normalized such that the average number counted in the wells that eceived 0 ng/ml rhGGF2, and 100 ng/ml NGF equals a value of 100.

Results

Figure 7:
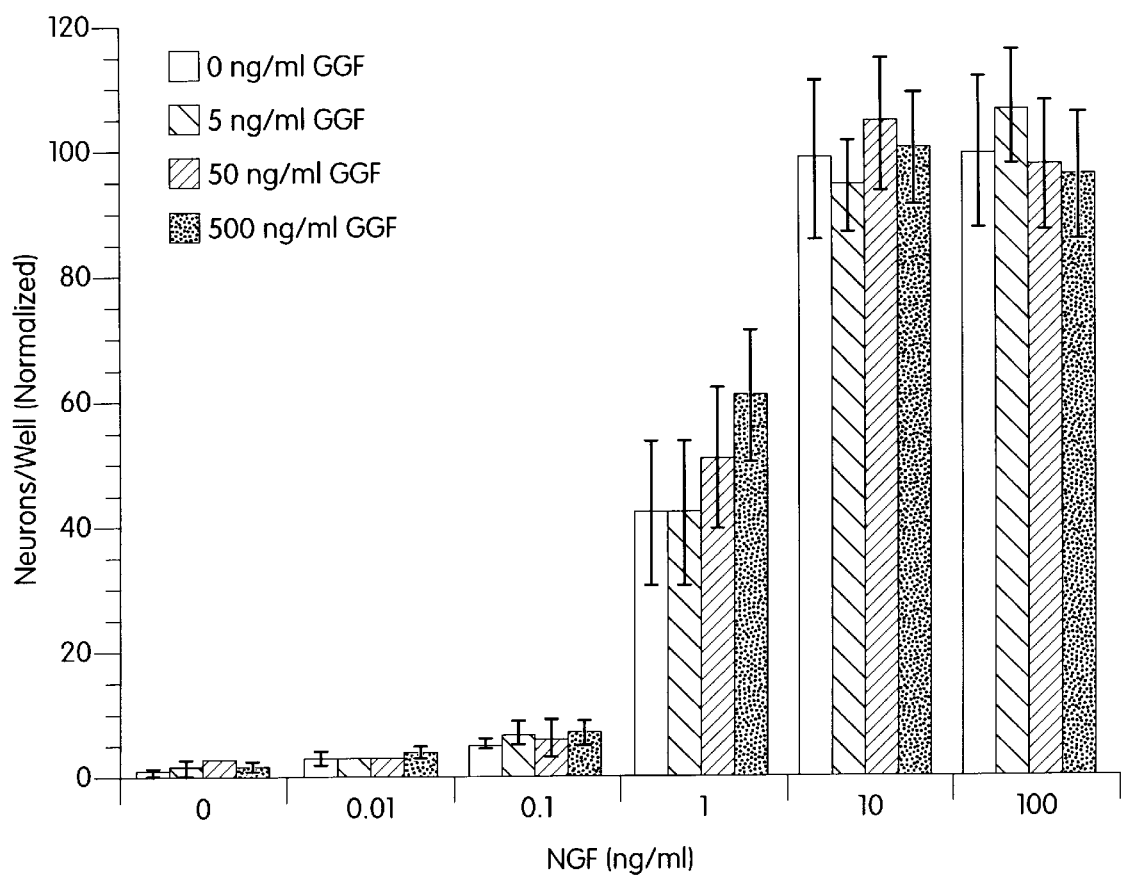
FIG. 7 shows experimental data of the effects of rhGGF2 on neuronal survival and outgrowth.

It is clear from the results presented in FIG. 7, that rhGGF2 has no direct effect on the survival of SCG neurons. All surviving neurons exhibited robust axon outgrowth, and there was no noticeable effect on the extent of axon outgrowth. As expected in the absence of rhGGF2, the number of neurons reaches a plateau at 10 ng/ml. The presence or absence of rhGGF2 appears to make no difference at the 3 doses tested.

Discussion and Conclusions

In light of the results presented in Example 1, it was necessary to examine whether the effect of rhGGF2 on axon outgrowth could be attributed to a direct effect of rhGGF2 on the neurons in question. The results of Example 2 make it clear that this is not the case. Thus one must conclude that the effect of rhGGF2 on axon outgrowth observed in the tube paradigm is due to a "bystander effect" rather than a direct action on the neurons. Thus rhGGF2 can promote the healing response of injured neurons by inducing the production of neurite promoting factors by non-neuronal support cells.

Example 3

Increase in Myelinated Axon Growth in an Animal Model of Peripheral Nerve Injury Mediated by a Neuregulin An animal model of peripheral nerve repair was used to test the ability of a neuregulin (rhGGF2) to increase the number of regenerating axons. The rationale is that added rhGGF2 will induce increases in Schwann cell (the first cell type) numbers as well as increases in the levels of trophic factors (Product A) produced by Schwann cells that, in turn, will affect a second cell type, the regenerating axons (the second cell type) as measured by increases in the number of myelinated axons (response).

Fisher 344 rats (male, 195–250 g) were surgically prepared and one sciatic nerve was transected resulting in a 10mm gap. Polyethylene guide tubes (13mm in length, 1.1 mm internal diameter) were prepared. These tubes contained a flat sliver of a collagen coated Immobilon filter (1.0×10 mm) containing immobilized rhGGF2 and were prepared as described in U.S. patent application Ser. No. 08/293,465, filed on Aug. 19, 1994, hereby incorporated by reference.

The strips were inserted into the lumen of the guide tubes. RhGGF2 was used at a concentration of 162 ug/uL (in phosphate buffered saline), 2.5 uL of this solution was added per strip. Control tubes were prepared containing collagen coated Immobilon strips treated with phosphate buffered saline alone. Tubes were secured with a single suture at the proximal and distal ends after filling the lumen with physiological saline and sealing the ends with vaseline.

Animals (10 rhGGF2 treated, 10 controls) were sacrificed at 28 days and the section of sciatic nerve containing the tube was excised, the nerve was removed from the tube and a cross section was taken from the mid point of the tube and prepared for histological analysis. The material was fixed in 4% paraformaldehyde and 2% glutaraldehyde for 24 h and then post fixed in 2% osmium tetroxide and embedded in glycomethacrylate One micron cross sections were taken and stained with 1 uM toluidine blue.

Figures 8A, 8B:
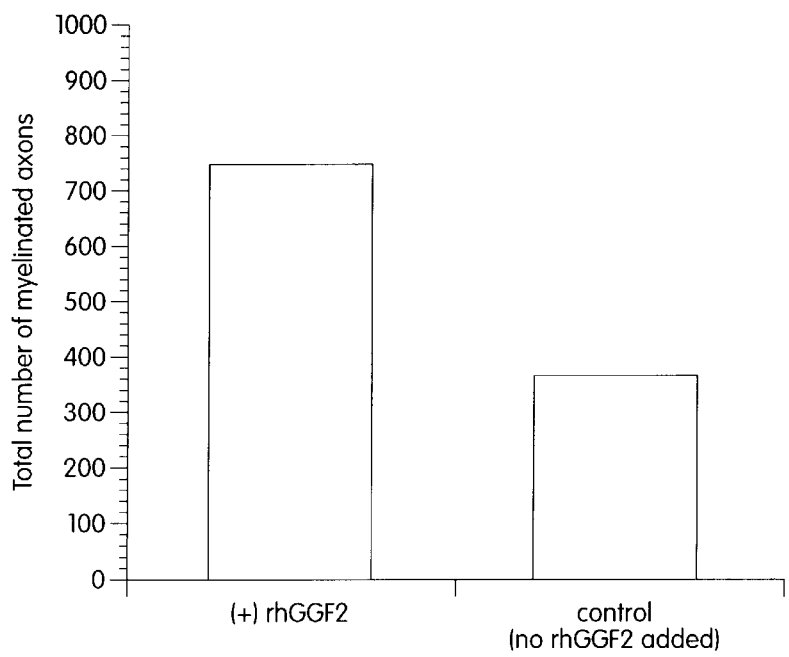
FIG. 8A shows data on the effects of exogenous GGF on the number of myelinated axons at 28 days post-injury.
FIG. 8B shows the above-referenced data in bar graph form.
Figure 9A:
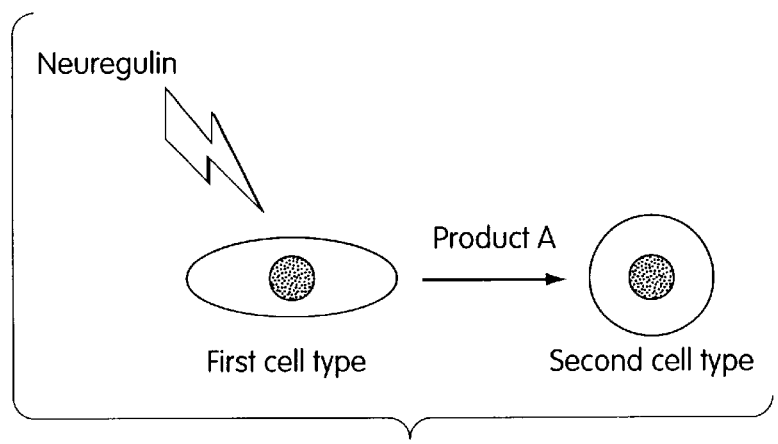
FIG. 9 represents a schematic illustration of the effect neuregulins can have on cellular communication.
Figure 9B:
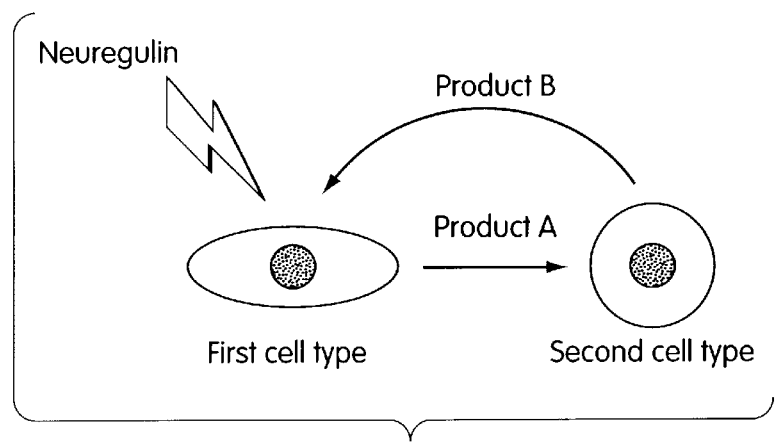
Figure 9C:
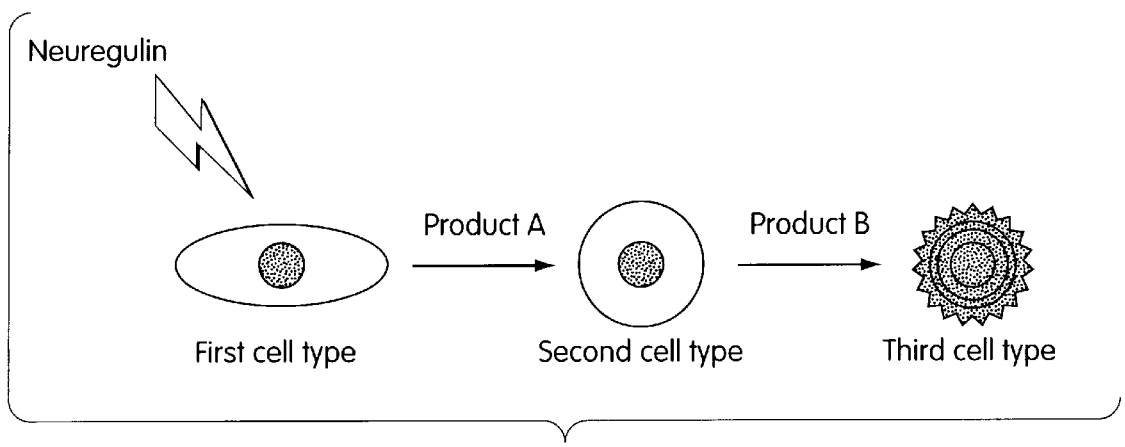
Figure 10:
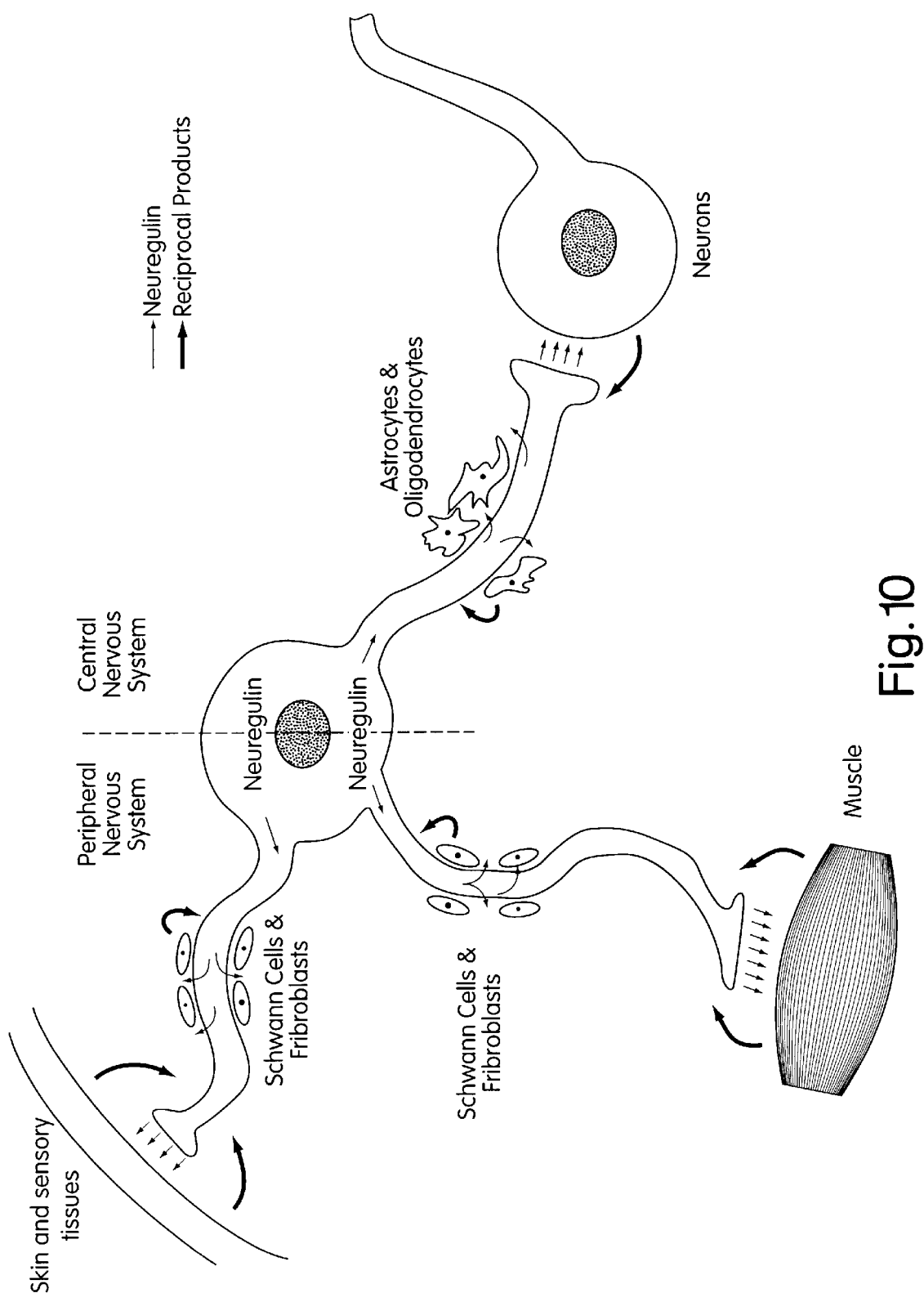
FIG. 10 represents a schematic illustration of specific effects of neuregulins on cellular communication.

A histological analysis of a section from the mid point of the tube was performed and measurements were made of the total number of myelinated axons in a section and the total endoneurial area in each section. The data are shown in FIGS. 8A and 8B.

The rhGGF2 treated animals showed a 2.1 fold increase in the number of myelinated axons over the control animals.

The results of this study demonstrate a positive effect of exogenously added rhGGF2 on the growth of myelinated axons. In consideration of the data discussed in example 1 where rhGGF2 acts on Schwann cells to induce the synthesis of products that are trophic for regenerating axons in an in vitro paradigm it is concluded that a similar mechanism is responsible for the rhGGF2 mediated enhancement of the growth of axons in vivo.

What is claimed is:

1. A method of affecting cellular communication between neuronal-associated cells and neuronal cells in a vertebrate, comprising administration of a neuregulin with $p185^{erbB2}$, $p185^{erbB3}$ or $p185^{erbB4}$ binding activity to said vertebrate wherein said neuregulin interacts with said neuronal-associated cells, resulting in production of at least one neurotrophic agent by said neuronal-associated cells and said neurotrophic agent or agents affect the mitotic activity, survival, differentiation or neurite outgrowth of said neuronal cells.

2. A method of claim 1 wherein said vertebrate is a human.

3. A method of claim 1 wherein said neuronal-associated cells are nervous system support cells.

4. A method of claim 3 wherein said nervous system support cells are glial cells.

5. A method of claim 1 wherein said neuronal-associated cells are sensory organ cells.

6. A method of claim 1 wherein said neuronal-associated cells are muscle cells.

7. A method of claim 1 wherein said neuronal cells are cholinergic neurons.

8. A method of claim 1 wherein said neuronal cells are non-cholinergic neurons.

9. A method of claim 1 wherein said neuregulin is rhGGF2.

10. A method of affecting cellular communication between neuronal-associated cells and neuronal cells in the peripheral nervous system of a vertebrate, comprising administration of a neuregulin with $p185^{erbB2}$, $p185^{erbB3}$ or $p185^{erbB4}$ binding activity to said vertebrate wherein said neuregulin interacts with said neuronal-associated cells, resulting in production of at least one neurotrophic agent by said neuronal-associated cells and said neurotrophic agent or agents affect the mitotic activity, survival, differentiation or neurite outgrowth of said neuronal cells.

11. A method of claim 10 wherein said neuronal associated cells are Schwann cells.

12. A method of claim 10 wherein said neuronal-associated cells are muscle cells.

13. A method of claim 10 wherein said neuronal-associated cells are skeletal muscle cells.

14. A method of claim 10 wherein said neuronal-associated cells are cardiac muscle cells.

15. A method of claim 10 wherein said neuronal-associated cells are smooth muscle cells.

16. A method of claim 10 wherein said neuronal-associated cells are sensory organ cells.

17. A method of claim 10 wherein said neuronal cells are cholinergic neurons.

18. A method of claim 10 wherein said neuronal cells are non-cholinergic neurons.

19. A method of treating a neurological disorder involving neuronal degeneration in the peripheral nervous system of a mammal, comprising administration of a therapeutically effective amount of a neuregulin with $p185^{erbB2}$, $p185^{erbB3}$ or $p185^{erbB4}$ binding activity to said mammal wherein said neuregulin interacts with neuronal-associated cells, resulting in the production of at least one neurotrophic agent which affects the mitotic activity, survival, differentiation or neurite outgrowth of neuronal cells.

20. A method of treating peripheral neuropathy and peripheral nerve injury comprising administration of a therapeutically effective amount of a neuregulin with $p185^{erbB2}$, $p185^{erbB3}$ or $p185^{erbB4}$ binding activity wherein said neuregulin interacts with a neuronal-associated cells, resulting in production of at least one neurotrophic agent by said neuronal-associated cells and said neurotrophic agent or agents affect the mitotic activity, survival, differentiation or neurite outgrowth of neuronal cells.

* * * * *